(12) United States Patent
Treace et al.

(10) Patent No.: US 12,279,794 B2
(45) Date of Patent: *Apr. 22, 2025

(54) TARSAL-METATARSAL JOINT PROCEDURE UTILIZING COMPRESSOR-DISTRACTOR AND INSTRUMENT PROVIDING SLIDING SURFACE

(71) Applicant: Treace Medical Concepts, Inc., Ponte Vedra, FL (US)

(72) Inventors: John T. Treace, Ponte Vedra Beach, FL (US); Joe W. Ferguson, Ponte Vedra Beach, FL (US); Carlos Eduardo Gil, Memphis, TN (US); Sean F. Scanlan, Jacksonville, FL (US)

(73) Assignee: Treace Medical Concepts, Inc., Ponte Vedra, FL (US)

( * ) Notice: Subject to any disclaimer, the term of this patent is extended or adjusted under 35 U.S.C. 154(b) by 25 days.

This patent is subject to a terminal disclaimer.

(21) Appl. No.: 18/186,711

(22) Filed: Mar. 20, 2023

(65) Prior Publication Data

US 2023/0218318 A1 Jul. 13, 2023

Related U.S. Application Data

(63) Continuation of application No. 16/784,742, filed on Feb. 7, 2020, now Pat. No. 11,607,250.

(Continued)

(51) Int. Cl.
*A61B 17/56* (2006.01)
*A61B 17/02* (2006.01)
(Continued)

(52) U.S. Cl.
CPC ............ *A61B 17/56* (2013.01); *A61B 17/025* (2013.01); *A61B 17/1775* (2016.11);
(Continued)

(58) Field of Classification Search
CPC ..... A61B 17/025; A61B 17/151; A61B 17/56; A61B 2017/565; A61B 17/60;
(Continued)

(56) References Cited

U.S. PATENT DOCUMENTS

| 2,251,209 A | 7/1941 | Stader |
| 2,432,695 A | 12/1947 | Speas |

(Continued)

FOREIGN PATENT DOCUMENTS

| AU | 2009227957 B2 | 7/2014 |
| CA | 2491824 A1 | 9/2005 |

(Continued)

OTHER PUBLICATIONS

Nagy et al., "The AO Ulnar Shortening Osteotomy System Indications and Surgical Technique," Journal of Wrist Surgery, vol. 3, No. 2, 2014, pp. 91-97.

(Continued)

*Primary Examiner* — Larry E Waggle, Jr.
(74) *Attorney, Agent, or Firm* — Fredrikson & Byron, P.A.

(57) ABSTRACT

A surgical technique can involve inserting an instrument defining a sliding surface between a metatarsal and a laterally-adjacent metatarsal. The technique can include moving the metatarsal across the sliding surface of the instrument toward the cuneiform to close a space between the metatarsal and the opposed cuneiform.

25 Claims, 25 Drawing Sheets

Related U.S. Application Data

(60) Provisional application No. 62/805,208, filed on Feb. 13, 2019.

(51) Int. Cl.
*A61B 17/17* (2006.01)
*A61B 17/66* (2006.01)
*A61B 17/88* (2006.01)

(52) U.S. Cl.
CPC .......... *A61B 17/66* (2013.01); *A61B 17/8866* (2013.01); *A61B 2017/565* (2013.01)

(58) Field of Classification Search
CPC . A61B 17/64; A61B 17/6466; A61B 17/6475; A61B 17/66
See application file for complete search history.

(56) References Cited

U.S. PATENT DOCUMENTS

| | | |
|---|---|---|
| 3,664,022 A | 5/1972 | Small |
| 4,069,824 A | 1/1978 | Weinstock |
| 4,159,716 A | 7/1979 | Borchers |
| 4,187,840 A | 2/1980 | Watanabe |
| 4,187,841 A | 2/1980 | Knutson |
| 4,335,715 A | 6/1982 | Kirkley |
| 4,338,927 A | 7/1982 | Volkov et al. |
| 4,349,018 A | 9/1982 | Chambers |
| 4,409,973 A | 10/1983 | Neufeld |
| 4,440,168 A | 4/1984 | Warren |
| 4,501,268 A | 2/1985 | Comparetto |
| 4,502,474 A | 3/1985 | Comparetto |
| 4,509,511 A | 4/1985 | Neufeld |
| 4,565,191 A | 1/1986 | Slocum |
| 4,570,624 A | 2/1986 | Wu |
| 4,627,425 A | 12/1986 | Reese |
| 4,628,919 A | 12/1986 | Clyburn |
| 4,632,102 A | 12/1986 | Comparetto |
| 4,664,102 A | 5/1987 | Comparetto |
| 4,708,133 A | 11/1987 | Comparetto |
| 4,730,608 A | 3/1988 | Schlein |
| 4,736,737 A | 4/1988 | Fargie et al. |
| 4,750,481 A | 6/1988 | Reese |
| 4,754,746 A | 7/1988 | Cox |
| 4,757,810 A | 7/1988 | Reese |
| 4,895,141 A | 1/1990 | Koeneman et al. |
| 4,952,214 A | 8/1990 | Comparetto |
| 4,959,066 A | 9/1990 | Dunn et al. |
| 4,978,347 A | 12/1990 | Ilizarov |
| 4,988,349 A | 1/1991 | Pennig |
| 4,995,875 A | 2/1991 | Coes |
| 5,021,056 A | 6/1991 | Hofmann et al. |
| 5,035,698 A | 7/1991 | Comparetto |
| 5,042,983 A | 8/1991 | Rayhack |
| 5,049,149 A | 9/1991 | Schmidt |
| 5,053,039 A | 10/1991 | Hofmann et al. |
| 5,078,719 A | 1/1992 | Schreiber |
| 5,112,334 A | 5/1992 | Alchermes et al. |
| 5,147,364 A | 9/1992 | Comparetto |
| 5,176,685 A | 1/1993 | Rayhack |
| 5,207,676 A | 5/1993 | Canadell et al. |
| 5,246,444 A | 9/1993 | Schreiber |
| 5,254,119 A | 10/1993 | Schreiber |
| 5,304,177 A | 4/1994 | Pennig |
| 5,312,412 A | 5/1994 | Whipple |
| 5,358,504 A | 10/1994 | Paley et al. |
| 5,364,402 A | 11/1994 | Mumme et al. |
| 5,374,271 A | 12/1994 | Hwang |
| 5,413,579 A | 5/1995 | Du Toit |
| 5,417,694 A | 5/1995 | Marik et al. |
| 5,449,360 A | 9/1995 | Schreiber |
| 5,470,335 A | 11/1995 | Du Toit |
| 5,490,854 A | 2/1996 | Fisher et al. |
| 5,529,075 A | 6/1996 | Clark |
| 5,540,695 A | 7/1996 | Levy |
| 5,578,038 A | 11/1996 | Slocum |
| 5,586,564 A | 12/1996 | Barrett et al. |
| 5,601,565 A | 2/1997 | Huebner |
| 5,613,969 A | 3/1997 | Jenkins, Jr. |
| 5,620,442 A | 4/1997 | Bailey et al. |
| 5,620,448 A | 4/1997 | Puddu |
| 5,643,270 A | 7/1997 | Combs |
| 5,667,510 A | 9/1997 | Combs |
| H1706 H | 1/1998 | Mason |
| 5,722,978 A | 3/1998 | Jenkins |
| 5,749,875 A | 5/1998 | Puddu |
| 5,779,709 A | 7/1998 | Harris et al. |
| 5,788,695 A | 8/1998 | Richardson |
| 5,803,924 A | 9/1998 | Oni et al. |
| 5,810,822 A | 9/1998 | Mortier |
| 5,843,085 A | 12/1998 | Graser |
| 5,893,553 A | 4/1999 | Pinkous |
| 5,911,724 A | 6/1999 | Wehrli |
| 5,935,128 A | 8/1999 | Carter et al. |
| 5,941,877 A | 8/1999 | Viegas et al. |
| 5,951,556 A | 9/1999 | Faccioli et al. |
| 5,980,526 A | 11/1999 | Johnson et al. |
| 5,984,931 A | 11/1999 | Greenfield |
| 6,007,535 A | 12/1999 | Rayhack et al. |
| 6,027,504 A | 2/2000 | McGuire |
| 6,030,391 A | 2/2000 | Brainard et al. |
| 6,162,223 A | 12/2000 | Orsak et al. |
| 6,171,309 B1 | 1/2001 | Huebner |
| 6,203,545 B1 | 3/2001 | Stoffella |
| 6,248,109 B1 | 6/2001 | Stoffella |
| 6,391,031 B1 | 5/2002 | Toomey |
| 6,416,465 B2 | 7/2002 | Brau |
| 6,478,799 B1 | 11/2002 | Williamson |
| 6,511,481 B2 | 1/2003 | von Hoffmann et al. |
| 6,547,793 B1 | 4/2003 | McGuire |
| 6,676,662 B1 | 1/2004 | Bagga et al. |
| 6,719,773 B1 | 4/2004 | Boucher et al. |
| 6,743,233 B1 | 6/2004 | Baldwin et al. |
| 6,755,838 B2 | 6/2004 | Trnka |
| 6,796,986 B2 | 9/2004 | Duffner |
| 6,859,661 B2 | 2/2005 | Tuke |
| 7,018,383 B2 | 3/2006 | McGuire |
| 7,033,361 B2 | 4/2006 | Collazo |
| 7,097,647 B2 | 8/2006 | Segler et al. |
| 7,112,204 B2 | 9/2006 | Justin et al. |
| 7,153,310 B2 | 12/2006 | Ralph et al. |
| 7,182,766 B1 | 2/2007 | Mogul |
| 7,241,298 B2 | 7/2007 | Nemec et al. |
| 7,282,054 B2 | 10/2007 | Steffensmeier et al. |
| 7,377,924 B2 | 5/2008 | Raistrick et al. |
| 7,465,303 B2 | 12/2008 | Riccione et al. |
| 7,540,874 B2 | 6/2009 | Trumble et al. |
| 7,572,258 B2 | 8/2009 | Stiernborg |
| 7,578,822 B2 | 8/2009 | Rezach et al. |
| 7,618,424 B2 | 11/2009 | Wilcox et al. |
| 7,641,660 B2 | 1/2010 | Lakin et al. |
| D610,257 S | 2/2010 | Horton |
| 7,686,811 B2 | 3/2010 | Byrd et al. |
| 7,691,108 B2 | 4/2010 | Lavallee |
| 7,763,026 B2 | 7/2010 | Egger et al. |
| D629,900 S | 12/2010 | Fisher |
| 7,967,823 B2 | 6/2011 | Ammann et al. |
| 7,972,338 B2 | 7/2011 | O'Brien |
| D646,389 S | 10/2011 | Claypool et al. |
| 8,057,478 B2 | 11/2011 | Kuczynski et al. |
| 8,062,301 B2 | 11/2011 | Ammann et al. |
| D651,315 S | 12/2011 | Bertoni et al. |
| D651,316 S | 12/2011 | May et al. |
| 8,080,010 B2 | 12/2011 | Schulz et al. |
| 8,080,045 B2 | 12/2011 | Wotton, III |
| 8,083,746 B2 | 12/2011 | Novak |
| 8,123,753 B2 | 2/2012 | Poncet |
| 8,137,406 B2 | 3/2012 | Novak et al. |
| 8,147,530 B2 | 4/2012 | Strnad et al. |
| 8,167,918 B2 | 5/2012 | Strnad et al. |
| 8,172,848 B2 | 5/2012 | Tomko et al. |
| 8,192,441 B2 | 6/2012 | Collazo |
| 8,197,487 B2 | 6/2012 | Poncet et al. |
| 8,231,623 B1 | 7/2012 | Jordan |

(56) References Cited

U.S. PATENT DOCUMENTS

| | | |
|---|---|---|
| 8,231,663 B2 | 7/2012 | Kay et al. |
| 8,236,000 B2 | 8/2012 | Ammann et al. |
| 8,246,561 B1 | 8/2012 | Agee et al. |
| D666,721 S | 9/2012 | Wright et al. |
| 8,262,664 B2 | 9/2012 | Justin et al. |
| 8,277,459 B2 | 10/2012 | Sand et al. |
| 8,282,644 B2 | 10/2012 | Edwards |
| 8,282,645 B2 | 10/2012 | Lawrence et al. |
| 8,292,966 B2 | 10/2012 | Morton |
| 8,303,596 B2 | 11/2012 | Plassky et al. |
| 8,313,492 B2 | 11/2012 | Wong et al. |
| 8,323,289 B2 | 12/2012 | Re |
| 8,337,503 B2 | 12/2012 | Lian |
| 8,343,159 B2 | 1/2013 | Bennett |
| 8,377,105 B2 | 2/2013 | Buescher |
| D679,395 S | 4/2013 | Wright et al. |
| 8,409,209 B2 | 4/2013 | Ammann et al. |
| 8,435,246 B2 | 5/2013 | Fisher et al. |
| 8,475,462 B2 | 7/2013 | Thomas et al. |
| 8,496,662 B2 | 7/2013 | Novak et al. |
| 8,518,045 B2 | 8/2013 | Szanto |
| 8,523,870 B2 | 9/2013 | Green, II et al. |
| 8,529,571 B2 | 9/2013 | Horan et al. |
| 8,540,777 B2 | 9/2013 | Ammann et al. |
| 8,545,508 B2 | 10/2013 | Collazo |
| D694,884 S | 12/2013 | Mooradian et al. |
| D695,402 S | 12/2013 | Dacosta et al. |
| 8,652,142 B2 | 2/2014 | Geissler |
| 8,657,820 B2 | 2/2014 | Kubiak et al. |
| D701,303 S | 3/2014 | Cook |
| 8,672,945 B2 | 3/2014 | Lavallee et al. |
| 8,696,716 B2 | 4/2014 | Kartalian et al. |
| 8,702,715 B2 | 4/2014 | Ammann et al. |
| D705,929 S | 5/2014 | Frey |
| 8,715,363 B2 | 5/2014 | Ratron et al. |
| 8,728,084 B2 | 5/2014 | Berelsman et al. |
| 8,758,354 B2 | 6/2014 | Habegger et al. |
| 8,764,760 B2 | 7/2014 | Metzger et al. |
| 8,764,763 B2 | 7/2014 | Wong et al. |
| 8,771,279 B2 | 7/2014 | Philippon et al. |
| 8,777,948 B2 | 7/2014 | Bernsteiner |
| 8,784,427 B2 | 7/2014 | Fallin et al. |
| 8,784,457 B2 | 7/2014 | Graham |
| 8,795,286 B2 | 8/2014 | Sand et al. |
| 8,801,727 B2 | 8/2014 | Chan et al. |
| 8,808,303 B2 | 8/2014 | Stemniski et al. |
| 8,828,012 B2 | 9/2014 | May et al. |
| 8,858,602 B2 | 10/2014 | Weiner et al. |
| 8,882,778 B2 | 11/2014 | Ranft |
| 8,882,816 B2 | 11/2014 | Kartalian et al. |
| 8,888,785 B2 | 11/2014 | Ammann et al. |
| D720,456 S | 12/2014 | Dacosta et al. |
| 8,900,247 B2 | 12/2014 | Tseng et al. |
| 8,906,026 B2 | 12/2014 | Ammann et al. |
| 8,945,132 B2 | 2/2015 | Plassy et al. |
| 8,998,903 B2 | 4/2015 | Price et al. |
| 8,998,904 B2 | 4/2015 | Zeetser et al. |
| 9,023,052 B2 | 5/2015 | Lietz et al. |
| 9,044,250 B2 | 6/2015 | Olsen et al. |
| 9,060,822 B2 | 6/2015 | Lewis et al. |
| 9,078,710 B2 | 7/2015 | Thoren et al. |
| 9,089,376 B2 | 7/2015 | Medoff et al. |
| 9,101,421 B2 | 8/2015 | Blacklidge |
| 9,107,715 B2 | 8/2015 | Blitz et al. |
| 9,113,920 B2 | 8/2015 | Ammann et al. |
| D740,424 S | 10/2015 | Dacosta et al. |
| D765,844 S | 9/2016 | DaCosta |
| D766,434 S | 9/2016 | DaCosta |
| D766,437 S | 9/2016 | DaCosta |
| D766,438 S | 9/2016 | DaCosta |
| D766,439 S | 9/2016 | DaCosta |
| 9,452,057 B2 | 9/2016 | Dacosta et al. |
| 9,522,023 B2 | 11/2016 | Haddad et al. |
| 9,592,084 B2 | 3/2017 | Grant |
| 9,622,805 B2 | 4/2017 | Santrock et al. |
| 9,750,538 B2 | 9/2017 | Soffiatti et al. |
| 9,770,272 B2 | 9/2017 | Thoren et al. |
| 9,785,747 B2 | 10/2017 | Geebelen |
| 9,924,969 B2 | 3/2018 | Triplett et al. |
| 9,936,994 B2 | 4/2018 | Smith et al. |
| 9,980,760 B2 | 5/2018 | Dacosta et al. |
| 10,028,750 B2 | 7/2018 | Rose |
| 10,064,631 B2 | 9/2018 | Dacosta et al. |
| 10,159,499 B2 | 12/2018 | Dacosta et al. |
| 10,292,713 B2 | 5/2019 | Fallin et al. |
| 10,327,829 B2 | 6/2019 | Dacosta et al. |
| 10,376,268 B2 | 8/2019 | Fallin et al. |
| 10,470,779 B2 | 11/2019 | Fallin et al. |
| 10,524,808 B1 | 1/2020 | Hissong et al. |
| 10,779,867 B2 | 9/2020 | Penzimer et al. |
| 10,939,939 B1 | 3/2021 | Gil et al. |
| 11,304,705 B2 | 4/2022 | Fallin et al. |
| 11,607,250 B2 * | 3/2023 | Treace ............... A61B 17/56 |
| 2002/0099381 A1 | 7/2002 | Maroney |
| 2002/0107519 A1 | 8/2002 | Dixon et al. |
| 2002/0165552 A1 | 11/2002 | Duffner |
| 2002/0198531 A1 | 12/2002 | Millard et al. |
| 2004/0010259 A1 | 1/2004 | Keller et al. |
| 2004/0039394 A1 | 2/2004 | Conti et al. |
| 2004/0097946 A1 | 5/2004 | Dietzel et al. |
| 2004/0138669 A1 | 7/2004 | Horn |
| 2005/0004676 A1 | 1/2005 | Schon et al. |
| 2005/0021040 A1 | 1/2005 | Bertagnoli |
| 2005/0059978 A1 | 3/2005 | Sherry et al. |
| 2005/0070909 A1 | 3/2005 | Egger et al. |
| 2005/0075641 A1 | 4/2005 | Singhatat et al. |
| 2005/0101961 A1 | 5/2005 | Huebner et al. |
| 2005/0149042 A1 | 7/2005 | Metzger |
| 2005/0203509 A1 | 9/2005 | Chinnaian et al. |
| 2005/0228389 A1 | 10/2005 | Stiernborg |
| 2005/0251147 A1 | 11/2005 | Novak |
| 2005/0267482 A1 | 12/2005 | Hyde, Jr. |
| 2005/0273112 A1 | 12/2005 | McNamara |
| 2006/0129163 A1 | 6/2006 | McGuire |
| 2006/0206044 A1 | 9/2006 | Simon |
| 2006/0217733 A1 | 9/2006 | Plassky et al. |
| 2006/0229604 A1 | 10/2006 | Olsen et al. |
| 2006/0229621 A1 | 10/2006 | Cadmus |
| 2006/0235383 A1 | 10/2006 | Hollawell |
| 2006/0241607 A1 | 10/2006 | Myerson et al. |
| 2006/0241608 A1 | 10/2006 | Myerson et al. |
| 2006/0264961 A1 | 11/2006 | Murray-Brown |
| 2007/0010818 A1 | 1/2007 | Stone et al. |
| 2007/0055233 A1 | 3/2007 | Brinker |
| 2007/0123857 A1 | 5/2007 | Deffenbaugh et al. |
| 2007/0233138 A1 | 10/2007 | Figueroa et al. |
| 2007/0265634 A1 | 11/2007 | Weinstein |
| 2007/0276383 A1 | 11/2007 | Rayhack |
| 2008/0009863 A1 | 1/2008 | Bond et al. |
| 2008/0015603 A1 | 1/2008 | Collazo |
| 2008/0039850 A1 | 2/2008 | Rowley et al. |
| 2008/0091197 A1 | 4/2008 | Coughlin |
| 2008/0140081 A1 | 6/2008 | Heavener et al. |
| 2008/0147073 A1 | 6/2008 | Ammann et al. |
| 2008/0172054 A1 | 7/2008 | Claypool et al. |
| 2008/0195215 A1 | 8/2008 | Morton |
| 2008/0208252 A1 | 8/2008 | Holmes |
| 2008/0262500 A1 | 10/2008 | Collazo |
| 2008/0269908 A1 | 10/2008 | Warburton |
| 2008/0288004 A1 | 11/2008 | Schendel |
| 2009/0036893 A1 | 2/2009 | Kartalian et al. |
| 2009/0036931 A1 | 2/2009 | Pech et al. |
| 2009/0054899 A1 | 2/2009 | Ammann et al. |
| 2009/0093849 A1 | 4/2009 | Grabowski |
| 2009/0105767 A1 | 4/2009 | Reiley |
| 2009/0118733 A1 | 5/2009 | Orsak et al. |
| 2009/0187189 A1 | 7/2009 | Mirza et al. |
| 2009/0198244 A1 | 8/2009 | Leibel |
| 2009/0198279 A1 | 8/2009 | Zhang et al. |
| 2009/0216089 A1 | 8/2009 | Davidson |
| 2009/0222047 A1 | 9/2009 | Graham |
| 2009/0254092 A1 | 10/2009 | Albiol Llorach |
| 2009/0254126 A1 | 10/2009 | Orbay et al. |
| 2009/0287309 A1 | 11/2009 | Walch et al. |

(56) References Cited

U.S. PATENT DOCUMENTS

| | | |
|---|---|---|
| 2010/0069910 A1 | 3/2010 | Hasselman |
| 2010/0121334 A1 | 5/2010 | Couture et al. |
| 2010/0125300 A1 | 5/2010 | Blitz et al. |
| 2010/0130981 A1 | 5/2010 | Richards |
| 2010/0152782 A1 | 6/2010 | Stone et al. |
| 2010/0168799 A1 | 7/2010 | Schumer |
| 2010/0185245 A1 | 7/2010 | Paul et al. |
| 2010/0249779 A1 | 9/2010 | Hotchkiss et al. |
| 2010/0256687 A1 | 10/2010 | Neufeld et al. |
| 2010/0318088 A1 | 12/2010 | Warne et al. |
| 2010/0324556 A1 | 12/2010 | Tyber et al. |
| 2011/0009865 A1 | 1/2011 | Orfaly |
| 2011/0093084 A1 | 4/2011 | Morton |
| 2011/0118739 A1 | 5/2011 | Tyber et al. |
| 2011/0172662 A1 | 7/2011 | Keilen |
| 2011/0178524 A1 | 7/2011 | Lawrence et al. |
| 2011/0245835 A1 | 10/2011 | Dodds et al. |
| 2011/0288550 A1 | 11/2011 | Orbay et al. |
| 2011/0301648 A1 | 12/2011 | Lofthouse et al. |
| 2012/0016426 A1 | 1/2012 | Robinson |
| 2012/0065689 A1 | 3/2012 | Prasad et al. |
| 2012/0078258 A1 | 3/2012 | Lo et al. |
| 2012/0123420 A1 | 5/2012 | Honiball |
| 2012/0123484 A1 | 5/2012 | Lietz et al. |
| 2012/0130376 A1 | 5/2012 | Loring et al. |
| 2012/0130382 A1 | 5/2012 | Iannotti et al. |
| 2012/0130383 A1 | 5/2012 | Budoff |
| 2012/0184961 A1 | 7/2012 | Johannaber |
| 2012/0185056 A1 | 7/2012 | Warburton |
| 2012/0191199 A1 | 7/2012 | Raemisch |
| 2012/0239045 A1 | 9/2012 | Li |
| 2012/0253350 A1 | 10/2012 | Anthony et al. |
| 2012/0265301 A1 | 10/2012 | Demers et al. |
| 2012/0277745 A1 | 11/2012 | Lizee |
| 2012/0303033 A1 | 11/2012 | Weiner et al. |
| 2012/0330135 A1 | 12/2012 | Millahn et al. |
| 2013/0012949 A1 | 1/2013 | Fallin et al. |
| 2013/0035694 A1 | 2/2013 | Grimm et al. |
| 2013/0085499 A1 | 4/2013 | Lian |
| 2013/0085502 A1 | 4/2013 | Harrold |
| 2013/0096563 A1 | 4/2013 | Meade et al. |
| 2013/0131821 A1 | 5/2013 | Cachia |
| 2013/0150900 A1 | 6/2013 | Haddad et al. |
| 2013/0150903 A1 | 6/2013 | Vincent |
| 2013/0158556 A1 | 6/2013 | Jones et al. |
| 2013/0165936 A1 | 6/2013 | Myers |
| 2013/0165938 A1 | 6/2013 | Chow et al. |
| 2013/0172942 A1 | 7/2013 | Lewis et al. |
| 2013/0184714 A1 | 7/2013 | Kaneyama et al. |
| 2013/0190765 A1 | 7/2013 | Harris et al. |
| 2013/0190766 A1 | 7/2013 | Harris et al. |
| 2013/0204259 A1 | 8/2013 | Zajac |
| 2013/0226248 A1 | 8/2013 | Hatch et al. |
| 2013/0226252 A1 | 8/2013 | Mayer |
| 2013/0231668 A1 | 9/2013 | Olsen et al. |
| 2013/0237987 A1 | 9/2013 | Graham |
| 2013/0237989 A1 | 9/2013 | Bonutti |
| 2013/0267956 A1 | 10/2013 | Terrill et al. |
| 2013/0310836 A1 | 11/2013 | Raub et al. |
| 2013/0325019 A1 | 12/2013 | Thomas et al. |
| 2013/0325076 A1 | 12/2013 | Palmer et al. |
| 2013/0331845 A1 | 12/2013 | Horan et al. |
| 2013/0338785 A1 | 12/2013 | Wong |
| 2014/0005672 A1 | 1/2014 | Edwards et al. |
| 2014/0025127 A1 | 1/2014 | Richter |
| 2014/0039501 A1 | 2/2014 | Schickendantz et al. |
| 2014/0039561 A1 | 2/2014 | Weiner et al. |
| 2014/0046387 A1 | 2/2014 | Waizenegger |
| 2014/0074099 A1 | 3/2014 | Vigneron et al. |
| 2014/0074101 A1 | 3/2014 | Collazo |
| 2014/0094861 A1 | 4/2014 | Fallin |
| 2014/0094924 A1 | 4/2014 | Hacking et al. |
| 2014/0135775 A1 | 5/2014 | Maxson et al. |
| 2014/0163563 A1 | 6/2014 | Reynolds et al. |
| 2014/0171953 A1 | 6/2014 | Gonzalvez et al. |
| 2014/0180342 A1 | 6/2014 | Lowery et al. |
| 2014/0188139 A1 | 7/2014 | Fallin et al. |
| 2014/0194884 A1 | 7/2014 | Martin et al. |
| 2014/0194999 A1 | 7/2014 | Orbay et al. |
| 2014/0207144 A1 | 7/2014 | Lee et al. |
| 2014/0228899 A1 | 8/2014 | Thoren et al. |
| 2014/0243825 A1 | 8/2014 | Yapp et al. |
| 2014/0249537 A1 | 9/2014 | Wong et al. |
| 2014/0257308 A1 | 9/2014 | Johannaber |
| 2014/0257509 A1 | 9/2014 | Dacosta et al. |
| 2014/0276815 A1 | 9/2014 | Riccione |
| 2014/0276853 A1 | 9/2014 | Long et al. |
| 2014/0277176 A1 | 9/2014 | Buchanan et al. |
| 2014/0277214 A1 | 9/2014 | Helenbolt et al. |
| 2014/0288562 A1 | 9/2014 | Von Zabern et al. |
| 2014/0296995 A1 | 10/2014 | Reiley et al. |
| 2014/0303621 A1 | 10/2014 | Gerold et al. |
| 2014/0336658 A1 | 11/2014 | Luna et al. |
| 2014/0343555 A1 | 11/2014 | Russi et al. |
| 2014/0350561 A1 | 11/2014 | Dacosta et al. |
| 2015/0032168 A1 | 1/2015 | Orsak et al. |
| 2015/0045801 A1 | 2/2015 | Axelson, Jr. et al. |
| 2015/0045839 A1 | 2/2015 | Dacosta et al. |
| 2015/0051650 A1 | 2/2015 | Verstreken et al. |
| 2015/0057667 A1 | 2/2015 | Ammann et al. |
| 2015/0066094 A1 | 3/2015 | Prandi et al. |
| 2015/0112446 A1 | 4/2015 | Melamed et al. |
| 2015/0119944 A1 | 4/2015 | Geldwert |
| 2015/0142064 A1 | 5/2015 | Perez et al. |
| 2015/0150608 A1 | 6/2015 | Sammarco |
| 2015/0182273 A1 | 7/2015 | Stemniski et al. |
| 2015/0223851 A1 | 8/2015 | Hill et al. |
| 2015/0245858 A1 | 9/2015 | Weiner et al. |
| 2016/0015426 A1 | 1/2016 | Dayton |
| 2016/0022315 A1 | 1/2016 | Soffiatti et al. |
| 2016/0135858 A1 | 5/2016 | Dacosta et al. |
| 2016/0151165 A1 | 6/2016 | Fallin et al. |
| 2016/0175089 A1 | 6/2016 | Fallin et al. |
| 2016/0192950 A1 | 7/2016 | Dayton et al. |
| 2016/0192970 A1 | 7/2016 | Dayton et al. |
| 2016/0199076 A1 | 7/2016 | Fallin et al. |
| 2016/0213384 A1 | 7/2016 | Fallin et al. |
| 2016/0235414 A1 | 8/2016 | Hatch et al. |
| 2016/0242791 A1 | 8/2016 | Fallin et al. |
| 2016/0256204 A1 | 9/2016 | Patel et al. |
| 2016/0270800 A1 | 9/2016 | Sanders |
| 2016/0324532 A1 | 11/2016 | Montoya et al. |
| 2016/0354127 A1 | 12/2016 | Lundquist et al. |
| 2017/0014143 A1 | 1/2017 | Dayton et al. |
| 2017/0014173 A1 | 1/2017 | Smith et al. |
| 2017/0042598 A1 | 2/2017 | Santrock et al. |
| 2017/0042599 A1 | 2/2017 | Bays et al. |
| 2017/0079669 A1* | 3/2017 | Bays ................. A61B 17/8866 |
| 2017/0143511 A1 | 5/2017 | Cachia |
| 2017/0164989 A1 | 6/2017 | Weiner et al. |
| 2018/0132868 A1 | 5/2018 | Dacosta et al. |
| 2018/0344334 A1 | 12/2018 | Kim et al. |
| 2019/0350598 A1 | 11/2019 | Jacobson |
| 2020/0015856 A1 | 1/2020 | Treace et al. |
| 2021/0244443 A1 | 8/2021 | Coyne et al. |

FOREIGN PATENT DOCUMENTS

| | | |
|---|---|---|
| CA | 2854997 A1 | 5/2013 |
| CH | 695846 A5 | 9/2006 |
| CN | 2930668 Y | 8/2007 |
| CN | 201558162 U | 8/2010 |
| CN | 201572172 U | 9/2010 |
| CN | 201586060 U | 9/2010 |
| CN | 201912210 U | 8/2011 |
| CN | 101237835 B | 11/2012 |
| CN | 202801773 U | 3/2013 |
| CN | 103462675 A | 12/2013 |
| CN | 103505276 A | 1/2014 |
| CN | 203458450 U | 3/2014 |
| CN | 102860860 B | 5/2014 |
| CN | 203576647 U | 5/2014 |
| CN | 104490460 A | 4/2015 |
| CN | 104510523 A | 4/2015 |

(56) References Cited

FOREIGN PATENT DOCUMENTS

| | | |
|---|---|---|
| CN | 104523327 A | 4/2015 |
| CN | 104546102 A | 4/2015 |
| CN | 204379413 U | 6/2015 |
| CN | 204410951 U | 6/2015 |
| CN | 204428143 U | 7/2015 |
| CN | 204428144 U | 7/2015 |
| CN | 204428145 U | 7/2015 |
| CN | 204446081 U | 7/2015 |
| DE | 202006010241 U1 | 3/2007 |
| DE | 102007053058 B3 | 4/2009 |
| EP | 685206 B1 | 9/2000 |
| EP | 1508316 B1 | 5/2007 |
| EP | 1897509 B1 | 7/2009 |
| EP | 2124772 A1 | 12/2009 |
| EP | 2124832 B1 | 8/2012 |
| EP | 2632349 A1 | 9/2013 |
| EP | 2665428 A1 | 11/2013 |
| EP | 2742878 A1 | 6/2014 |
| EP | 2750617 A1 | 7/2014 |
| EP | 2849684 A1 | 3/2015 |
| EP | 2932925 A1 | 10/2015 |
| EP | 2624764 B1 | 12/2015 |
| EP | 3023068 A2 | 5/2016 |
| FR | 2362616 A1 | 3/1978 |
| FR | 2764183 B1 | 11/1999 |
| FR | 2953120 B1 | 1/2012 |
| FR | 3030221 A1 | 6/2016 |
| GB | 2154143 A | 9/1985 |
| GB | 2154144 A | 9/1985 |
| GB | 2334214 B | 1/2003 |
| IN | 200903719 P1 | 6/2009 |
| IN | 200904479 P2 | 5/2010 |
| IN | 140/DELNP/2012 P1 | 2/2013 |
| IN | 2004/KOLNP/2013 P2 | 11/2013 |
| JP | 8635739 A | 1/1988 |
| JP | 2004174265 A | 6/2004 |
| JP | 2006158972 A | 6/2006 |
| JP | 4134243 B2 | 8/2008 |
| JP | 4162380 B2 | 10/2008 |
| JP | 2011092405 A | 5/2011 |
| JP | 2011523889 A | 8/2011 |
| JP | 4796943 B2 | 10/2011 |
| JP | 5466647 B2 | 4/2014 |
| JP | 2014511207 A | 5/2014 |
| JP | 2014521384 A | 8/2014 |
| JP | 5628875 B2 | 11/2014 |
| KR | 100904142 B1 | 6/2009 |
| MD | 756 Z | 11/2014 |
| RU | 2098036 C1 | 12/1997 |
| RU | 2195892 C2 | 1/2003 |
| RU | 2320287 C1 | 3/2008 |
| RU | 2321366 C2 | 4/2008 |
| RU | 2321369 C1 | 4/2008 |
| RU | 2346663 C2 | 2/2009 |
| RU | 2412662 C1 | 2/2011 |
| SU | 1333328 A2 | 8/1987 |
| WO | 0166022 A1 | 9/2001 |
| WO | 03075775 A1 | 9/2003 |
| WO | 2004089227 A2 | 10/2004 |
| WO | 2005122923 A1 | 12/2005 |
| WO | 2008051064 A1 | 5/2008 |
| WO | 2009029798 A1 | 3/2009 |
| WO | 2009032101 A2 | 3/2009 |
| WO | 2011037885 A1 | 3/2011 |
| WO | 2012029008 A1 | 3/2012 |
| WO | 2013090392 A1 | 6/2013 |
| WO | 2013134387 A1 | 9/2013 |
| WO | 2013169475 A1 | 11/2013 |
| WO | 2014020561 A1 | 2/2014 |
| WO | 2014022055 A1 | 2/2014 |
| WO | 2014035991 A1 | 3/2014 |
| WO | 2014085882 A1 | 6/2014 |
| WO | 2014147099 A1 | 9/2014 |
| WO | 2014152219 A2 | 9/2014 |
| WO | 2014152535 A1 | 9/2014 |
| WO | 2014177783 A1 | 11/2014 |
| WO | 2014200017 A1 | 12/2014 |
| WO | 2015094409 A1 | 6/2015 |
| WO | 2015105880 A1 | 7/2015 |
| WO | 2015127515 A2 | 9/2015 |
| WO | 2016134160 A1 | 8/2016 |
| WO | 2017134486 A1 | 8/2017 |

OTHER PUBLICATIONS

NexFix from Nexa Orthopedics, MetaFix I from Merete Medical, Inc. and The BioPro Lower Extremities from BioPro, found in Foot & Ankle International Journal, vol. 28, No. 1, Jan. 2007, 4 pages.

Odenbring et al., "A guide instrument for high tibial osteotomy," Acta Orthopaedica Scandinavica, vol. 60, No. 4, 1989, pp. 449-451.

Okuda et al., "Postoperative Incomplete Reduction of the Sesamoids as a Risk Factor for Recurrence of Hallux Valgus," The Journal of Bone and Joint Surgery, vol. 91-A, No. 1, Jul. 2009, pp. 1637-1645.

Osher et al., "Accurate Determination of Relative Metatarsal Protrusion with a Small Intermetatarsal Angle: A Novel Simplified Method," The Journal of Foot & Ankle Surgery, vol. 53, No. 5, Sep./Oct. 2014, published online: Jun. 3, 2014, pp. 548-556.

Otsuki et al., "Developing a novel custom cutting guide for curved per-acetabular osteotomy," International Orthopaedics (SICOT), vol. 37, 2013, pp. 1033-1038.

Patel et al., "Modified Lapidus Arthrodesis: Rate of Nonunion in 227 Cases," The Journal of Foot & Ankle Surgery, vol. 43, No. 1, Jan./Feb. 2004, pp. 37-42.

"Patient to Patient Precision, Accu-Cut, Osteotomy Guide System," BioPro, Foot & Ankle International Journal, vol. 23, No. 8, Aug. 2002, 2 pages.

Peters et al., "Flexor Hallucis Longus Tendon Laceration as a Complication of Total Ankle Arthroplasty," Foot & Ankle International, vol. 34, No. 1, 2013, pp. 148-149.

"Prophecy Inbone Preoperative Navigation Guides," Wright Medical Technology, Inc., Nov. 2013, 6 pages.

"Rayhack Ulnar Shortening Generation II Low-Profile Locking System Surgical Technique," Wright Medical Technology, Inc., Dec. 2013, 20 pages.

Rx-Fix Mini Rail External Fixator, Wright Medical Technology, Brochure, Aug. 15, 2014, 2 pages.

Saltzman et al., "Prospective Controlled Trial of STAR Total Ankle Replacement Versus Ankle Fusion: Initial Results," Foot & Ankle International, vol. 30, No. 7, Jul. 2009, pp. 579-596.

Scanlan et al. "Technique Tip: Subtalar Joint Fusion Using a Parallel Guide and Double Screw Fixation," The Journal of Foot and Ankle Surgery, vol. 49, Issue 3, May-Jun. 2010, pp. 305-309, (Abstract Only).

Scranton Jr. et al., "Anatomic Variations in the First Ray: Part I. Anatomic Aspects Related to Bunion Surgery," Clinical Orthopaedics and Related Research, vol. 151, Sep. 1980, pp. 244-255.

Siddiqui et al. "Fixation Of Metatarsal Fracture With Bone Plate In A Dromedary Heifer," Open Veterinary Journal, vol. 3, No. 1, 2013, pp. 17-20.

Sidekick Stealth Rearfoot Fixator, Wright Medical Technology, Surgical Technique, Dec. 2, 2013, 20 pages.

Simpson et al., "Computer-Assisted Distraction Ostegogenesis By Ilizarov's Method," International Journal of Medical Robots and Computer Assisted Surgery, vol. 4, No. 4, Dec. 2008, pp. 310-320, (Abstract Only).

Small Bone External Fixation System, Acumed, Surgical Technique, Effective date Sep. 2014, 8 pages.

"Smith & Nephew scores a Hat-Trick with its entry into the high-growth hammer toe repair market," Smith & Nephew, Jul. 31, 2014, 2 pages.

Stableloc External Fixation System, Acumed, Product Overview, Effective date Sep. 2015, 4 pages.

Stahl et al., "Derotation Of Post-Traumatic Femoral Deformities By Closed Intramedullary Sawing," Injury, vol. 37, No. 2, Feb. 2006, pp. 145-151, (Abstract Only).

Talbot et al.,"Assessing Sesamoid Subluxation: How Good is the AP Radiograph?," Foot and Ankle International, vol. 19, No. 8, Aug. 1998, pp. 547-554.

(56) References Cited

OTHER PUBLICATIONS

TempFix Spanning the Ankle Joint Half Pin and Transfixing Pin Techniques, Biomet Orthopedics, Surgical Technique, 2012, 16 pages.
Toth et al., "The Effect of First Ray Shortening in the Development of Metatarsalgia in the Second Through Fourth Rays After Metatarsal Osteotomy," Foot & Ankle International, vol. 28, No. 1, Jan. 2007, pp. 61-63.
Tricot et al., "3D-corrective osteotomy using surgical guides for posttraumatic distal humeral deformity," Acta Orthopaedica Belgica, vol. 78, No. 4, 2012, pp. 538-542.
Vitek et al., "Die Behandlung des Hallux rigidus mit Cheilektomie und Akin-Moberg-Osteotomie unter Verwendung einer neuen Schnittlehre und eines neuen Schraubensystems," Orthopadische Praxis, vol. 44, Nov. 2008, pp. 563-566, including English Abstract on p. 564.
Vitek, "Neue Techniken in der Fußchirurgie Das V-tek-System," ABW Wissenschaftsverlag GmbH, 2009, 11 pages, including English Abstract.
Weber et al., "A Simple System For Navigation Of Bone Alignment Osteotomies Of The Tibia," International Congress Series, vol. 1268, Jan. 2004, pp. 608-613, (Abstract Only).
Weil et al., "Anatomic Plantar Plate Repair Using the Weil Metatarsal Osteotomy Approach," Foot & Ankle Specialist, vol. 4, No. 3, 2011, pp. 145-150.
Wendl et al., "Navigation in der Knieendoprothetik," OP-Journal, vol. 17, 2002, pp. 22-27, including English Abstract.
Whipple et al., "Zimmer Herbert Whipple Bone Screw System: Surgical Techniques for Fixation of Scaphoid and Other Small Bone Fractures," Zimmer, 2003, 59 pages.
Yakacki et al. "Compression Forces of Internal and External Ankle Fixation Devices with Simulated Bone Resorption," Foot and Ankle International, vol. 31, No. 1, Jan. 2010, pp. 76-85, (Abstract Only).
Yasuda et al., "Proximal Supination Osteotomy of the First Metatarsal for Hallux Valgus," Foot and Ankle International, vol. 36, No. 6, Jun. 2015, pp. 696-704.
Boffeli et al., "Can We Abandon Saw Wedge Resection in Lapidus Fusion? A Comparative Study of Joint Preparation Techniques Regarding Correction of Deformity, Union Rate, and Preservation of First Ray Length," The Journal of Foot and Ankle Surgery, vol. 58, No. 6, Nov. 2019, published online: Sep. 25, 2019, pp. 1118-1124.
Conti et al., "Effect of the Modified Lapidus Procedure on Pronation of the First Ray in Hallux Valgus," Foot & Ankle International, Feb. 1, 2020, published online: Oct. 16, 2019, 8 pages.
Conti et al., "Effect of the Modified Lapidus Procedure for Hallux Valgus on Foot Width," Foot & Ankle International, Feb. 1, 2020, published online: Oct. 30, 2019, 6 pages.
Cruz et al., "Does Hallux Valgus Exhibit a Deformity Inherent to the First Metatarsal Bone?" The Journal of Foot & Ankle Surgery, vol. 58, No. 6, Nov. 2019, pp. 1210-1214.
Dahlgren et al., "First Tarsometatarsal Fusion Using Saw Preparation vs. Standard Preparation of the Joint: A Cadaver Study," Foot & Ankle Orthopaedics, vol. 4, No. 4, Oct. 2019, 2 pages.
Hatch et al., "Triplane Hallux Abducto Valgus Classification," The Journal of Foot & Ankle Surgery, vol. 57, No. 5, Sep./Oct. 2018, published online: May 18, 2018, pp. 972-981.
Langan et al., "Maintenance of Correction of the Modified Lapidus Procedure With a First Metatarsal to Intermediate Cuneiform Cross-Screw Technique," Foot & Ankle International, vol. 41, No. 4, Apr. 1, 2020, published online: Dec. 26, 2019, pp. 426-436.
Li et al., "Evolution of Thinking of the Lapidus Procedure and Fixation," Foot and Ankle Clinics, vol. 25, No. 1, Mar. 2020, published online: Dec. 16, 2019, pp. 18 pages.
Lopez et al., "Metatarsalgia: Assessment Algorithm and Decision Making," Foot and Ankle Clinics, vol. 24, No. 4, Dec. 2019, published online: Sep. 25, 2019, pp. 561-569.
Ray et al., "Multicenter Early Radiographic Outcomes of Triplanar Tarsometatarsal Arthrodesis With Early Weightbearing," Foot & Ankle International, vol. 40, No. 8, Aug. 1, 2019, published online: May 5, 2019, 7 pages.
Walker et al., "The Role of First Ray Insufficiency in the Development of Metatarsalgia," Foot and Ankle Clinics, vol. 24, No. 4, Dec. 2019, published online: Sep. 5, 2019, pp. 641-648.
Defendant Fusion Orthopedics LLC's Invalidity Contentions, No. CV-22-00490-PHX-SRB, US District Court for the District of Arizona, Aug. 27, 2022, 41 pages.
Prior Art Publications, Exhibit A of Defendant Fusion Orthopedics LLC's Invalidity Contentions, No. CV-22-00490-PHX-SRB, US District Court for the District of Arizona, Aug. 27, 2022, 3 pages.
Claim Chart for Fishco, "Making the Lapidus Easy," The Podiatry Institute (Apr. 2014), Exhibit B1 of Defendant Fusion Orthopedics LLC's Invalidity Contentions, No. CV-22-00490-PHX-SRB, US District Court for the District of Arizona, Aug. 27, 2022, 97 pages.
Claim Chart for Fishco, "A Straightforward Guide to the Lapidus Bunionectomy," HMP Global (Sep. 6, 2013), Exhibit B2 of Defendant Fusion Orthopedics LLC's Invalidity Contentions, No. CV-22-00490-PHX-SRB, US District Court for the District of Arizona, Aug. 27, 2022, 67 pages.
Claim Chart for Groves, "Functional Position Joint Sectioning: Pre-Load Method for Lapidus Arthrodesis," Update 2015: Proceedings of the Annual Meeting of the Podiatry Institute, Chpt. 6, pp. 23-29 (Apr. 2015), Exhibit B3 of Defendant Fusion Orthopedics LLC's Invalidity Contentions, No. CV-22-00490-PHX-SRB, US District Court for the District of Arizona, Aug. 27, 2022, 151 pages.
Claim Chart for Mote, "First Metatarsal-Cuneiform Arthrodesis for the Treatment of First Ray Pathology: A Technical Guide," The Journal Foot & Ankle Surgery (Sep. 1, 2009), Exhibit B5 of Defendant Fusion Orthopedics LLC's Invalidity Contentions, No. CV-22-00490-PHX-SRB, US District Court for the District of Arizona, Aug. 27, 2022, 21 pages.
Claim Chart for U.S. Pat. No. 10,376,268 to Fallin et al., entitled "Indexed Tri-Planar Osteotomy Guide and Method," Issued Aug. 13, 2019, Exhibit B6 of Defendant Fusion Orthopedics LLC's Invalidity Contentions, No. CV-22-00490-PHX-SRB, US District Court for the District of Arizona, Aug. 27, 2022, 155 pages.
Claim Chart for U.S. Pat. No. 8,282,645 to Lawrence et al., entitled "Metatarsal Bone Implant Cutting Guide," issued Jan. 18, 2010, Exhibit B7 of Defendant Fusion Orthopedics LLC's Invalidity Contentions, No. CV-22-00490-PHX-SRB, US District Court for the District of Arizona, Aug. 27, 2022, 76 pages.
Claim Chart for U.S. Pat. No. 9,452,057 to Dacosta et al., entitled "Bone Implants and Cutting Apparatuses and Methods," issued Apr. 8, 2011, Exhibit B8 of Defendant Fusion Orthopedics LLC's Invalidity Contentions, No. CV-22-00490-PHX-SRB, US District Court for the District of Arizona, Aug. 27, 2022, 110 pages.
Obviousness Chart, Exhibit C of Defendant Fusion Orthopedics LLC's Invalidity Contentions, No. CV-22-00490-PHX-SRB, US District Court for the District of Arizona, Aug. 27, 2022, 153 pages.
"Foot and Ankle Instrument Set," Smith & Nephew, 2013, 2 pages.
"Lapidus Pearls: Gaining Joint Exposure to Decrease Non-Union," Youtube, Retrieved online from <https://www.youtube.com/watch?v=-jqJyE7pj-Y>, dated Nov. 2, 2009, 3 pages.
"Reconstructive Surgery of the Foot & Ankle," The Podiatry Institute, Update 2015, Conference Program, May 2015, 28 pages.
"Speed Continuous Active Compression Implant," BioMedical Enterprises, Inc., A120-029 Rev. 3, 2013, 4 pages.
"Visionaire: Patient Matched Cutting Blocks Surgical Procedure," Smith & Nephew, Inc., 2009, 2 pages.
Arthrex, "Comprehensive Foot System," Retrieved online from <https://www.arthrex.com/resources/animation/8U3iaPvY6kO8bwFAwZF50Q/comprehensive-foot-system?referringTeam=foot_and_ankle>, dated Aug. 27, 2013, 3 pages.
Baravarian, "Why the Lapidus Procedure is Ideal for Bunions," Podiatry Today, Retrieved online from <https://www.hmpglobal-learhmpgloballe.com/site/podipodi/article/5542>, dated May 2006, 8 pages.

(56) References Cited

OTHER PUBLICATIONS

Bauer et al., "Offset-V Osteotomy of the First Metatarsal Shaft in Hallux Abducto Valgus," McGlamry's Comprehensive Textbook of Foot and Ankle Surgery, Fourth Edition, vol. 1, Chapter 29, 2013, 26 pages.

Cottom, "Fixation of the Lapidus Arthrodesis with a Plantar Interfragmentary Screw and Medial Low Profile Locking Plate," The Journal of Foot & Ankle Surgery, vol. 51, 2012, pp. 517-522.

Coughlin, "Fixation of the Lapidus Arthrodesis with a Plantar Interfragmentary Screw and Medial Low Profile Locking Plate," Orthopaedics and Traumatology, vol. 7, 1999, pp. 133-143.

Dayton et al., "Observed Changes in Radiographic Measurements of the First Ray after Frontal Plane Rotation of the First Metatarsal in a Cadaveric Foot Model," The Journal of Foot & Ankle Surgery, vol. 53, 2014, pp. 274-278.

Dayton et al., "Relationship of Frontal Plane Rotation of First Metatarsal to Proximal Articular Set Angle and Hallux Alignment in Patients Undergoing Tarsometatarsal Arthrodesis for Hallux Abducto Valgus: A Case Series and Critical Review of the Literature," The Journal of Foot & Ankle Surgery, 2013, Article in Press, Mar. 1, 2013, 7 pages.

DiDomenico et al., "Lapidus Bunionectomy: First Metatarsal-Cuneiform Arthrodesis," McGlamry's Comprehensive Textbook of Foot and Ankle Surgery, Fourth Edition, vol. 1, Chapter 31, 2013, 24 pages.

Fallin et al., US Provisional Application Entitled Indexed Tri-Planar Osteotomy Guide and Method, U.S. Appl. No. 62/118,378, filed Feb. 19, 2015, 62 pages.

Fishco, "A Straightforward Guide To The Lapidus Bunionectomy," Podiatry Today, Retrieved online from <https://www.hmpgloballearningnetwork.com/site/podiatry/blogged/straightforward-guide-lapidus-bunionectomy>, dated Sep. 6, 2013, 5 pages.

Fishco, "Making the Lapidus Easy," The Podiatry Institute, Update 2014, Chapter 14, 2014, pp. 91-93.

Fleming et al., "Results of Modified Lapidus Arthrodesis Procedure Using Medial Eminence as an Interpositional Autograft," The Journal of Foot & Ankle Surgery, vol. 50, 2011, pp. 272-275.

Fuhrmann, "Arthrodesis of the First Tarsometatarsal Joint for Correction of the Advanced Splayfoot Accompanied by a Hallux Valgus," Operative Orthopadie und Traumatologie, No. 2, 2005, pp. 195-210.

Gerard et al., "The Modified Lapidus Procedure," Orthopedics, vol. 31, No. 3, Mar. 2008, 7 pages.

Giannoudis et al., "Hallux Valgus Correction," Practical Procedures in Elective Orthopaedic Surgery, Pelvis and Lower Extremity, Chapter 38, 2012, 22 pages.

Greiner, "The Jargon of Pedal Movements," Foot & Ankle International, vol. 28, No. 1, Jan. 2007, pp. 109-125.

Groves, "Functional Position Joint Sectioning: Pre-Load Method for Lapidus Arthrodesis," The Podiatry Institute, Update 2015, Chapter 6, 2015, pp. 23-29.

Hardy et al., "Observations on Hallux Valgus," The Journal of Bone and Joint Surgery, vol. 33B, No. 3, Aug. 1951, pp. 376-391.

Holmes, Jr., "Correction of the Intermetatarsal Angle Component of Hallux Valgus Using Fiberwire-Attached Endo-buttons," Revista Internacional de Ciencias Podologicas, vol. 6, No. 2, 2012, pp. 73-79.

Integra, "Integra Large Qwix Positioning and Fixation Screw, Surgical Technique," 2012, 16 pages.

Kilmartin et al., "Combined rotation scarf and Akin osteotomies for hallux valgus: a patient focused 9 year follow up pf 50 patients," Journal of Foot and Ankle Research, vol. 3, No. 2, 2010, 12 pages.

Lee et al., "Technique Tip: Lateral Soft-Tissue Release for Correction of Hallux Valgus Through a Medial Incision Using A Dorsal Flap Over the First Metatarsal," Foot & Ankle International, vol. 28, No. 8, Aug. 2007, pp. 949-951.

Mote et al., "First Metatarsal-Cuneiform Arthrodesis for the Treatment of First Ray Pathology: A Technical Guide," JFAS Techniques Guide, vol. 48, No. 5, Sep./Oct. 2009, pp. 593-601.

Myerson, "Cuneiform-Metatarsal Arthrodesis," The Foot and Ankle, Chapter 9, 1997, pp. 107-117.

Sammarco, "Surgical Strategies: Mau Osteotomy for Correction of Moderate and Severe Hallux Valgus Deformity," Foot & Ankle International, vol. 28, No. 7, Jul. 2007, pp. 857-864.

Schon et al., "Cuneiform-Metatarsal Arthrodesis for Hallux Valgus, "The Foot and Ankle, Second Edition, Chapter 8, 2002, pp. 99-117.

Sokoloff, "Lapidus Procedure," Textbook of Bunion Surgery, Chapter 15, 1981, pp. 277-287.

Stamatis et al., "Mini Locking Plate as "Medial Buttress" for Oblique Osteotomy for Hallux Valgus," Foot & Ankle International, vol. 31, No. 10, Oct. 2010, pp. 920-922.

Wukich et al., "Hypermobility of the First Tarsometatarsal Joint," Foot and Ankle Clinics, vol. 10, No. 1, Mar. 2005, pp. 157-166.

Dayton et al., "Biwinged Excision for Round Pedal Lesions," The Journal of Foot and Ankle Surgery, vol. 35, No. 3, 1996, pp. 244-249.

Dayton et al., "Medial Incision Approach to the First Metatarsophalangeal Joint," The Journal of Foot and Ankle Surgery, vol. 40, No. 6, Nov./Dec. 2001, pp. 414-417.

Dayton et al., "Reduction of the Intermetatarsal Angle after First Metatarsophalangeal Joint Arthrodesis in Patients with Moderate and Severe Metatarsus Primus Adductus," The Journal of Foot and Ankle Surgery, vol. 41, No. 5, Sep./Oct. 2002, pp. 316-319.

Dayton et al., "Use of the Z Osteotomy for Tailor Bunionectomy," The Journal of Foot and Ankle Surgery, vol. 42, No. 3, May/Jun. 2003, pp. 167-169.

Dayton et al., "Early Weightbearing After First Metatarsophalangeal Joint Arthrodesis: A Retrospective Observational Case Analysis," The Journal of Foot and Ankle Surgery, vol. 43, No. 3, May/Jun. 2004, pp. 156-159.

Dayton et al., "Dorsal Suspension Stitch: An Alternative Stabilization After Flexor Tenotomy for Flexible Hammer Digit Syndrome," The Journal of Foot and Ankle Surgery, vol. 48, No. 5, Sep./Oct. 2009, pp. 602-605.

Dayton et al., "The Extended Knee Hemilithotomy Position for Gastrocnemius Recession," The Journal of Foot and Ankle Surgery, vol. 49, 2010, pp. 214-216.

Wienke et al., "Bone Stimulation For Nonunions: What the Evidence Reveals," Podiatry Today, vol. 24, No. 9, Sep. 2011, pp. 52-57.

Dayton et al., "Hallux Varus as Complication of Foot Compartment Syndrome," The Journal of Foot and Ankle Surgery, vol. 50, 2011, pp. 504-506.

Dayton et al., "Measurement of Mid-Calcaneal Length on Plain Radiographs: Reliability of a New Method," Foot and Ankle Specialist, vol. 4, No. 5, Oct. 2011, pp. 280-283.

Dayton et al., "A User-Friendly Method of Pin Site Management for External Fixators," Foot and Ankle Specialist, Sep. 16, 2011, 4 pages.

Dayton et al., "Effectiveness of a Locking Plate in Preserving Midcalcaneal Length and Positional Outcome after Evans Calcaneal Osteotomy: A Retrospective Pilot Study," The Journal of Foot and Ankle Surgery, vol. 52, 2013, pp. 710-713.

Dayton et al., "Does Postoperative Showering or Bathing of a Surgical Site Increase the Incidence of Infection? A Systematic Review of the Literature," The Journal of Foot and Ankle Surgery, vol. 52, 2013, pp. 612-614.

Dayton et al., "Technique for Minimally Invasive Reduction of Calcaneal Fractures Using Small Bilateral External Fixation," The Journal of Foot and Ankle Surgery, Article in Press, 2014, 7 pages.

Dayton et al., "Clarification of the Anatomic Definition of the Bunion Deformity," The Journal of Foot and Ankle Surgery, vol. 53, 2014, pp. 160-163.

Dayton et al., "Observed Changes in Radiographic Measurements of the First Ray after Frontal Plane Rotation of the First Metatarsal in a Cadaveric Foot Model," The Journal of Foot and Ankle Surgery, Article in Press, 2014, 5 pages.

Dayton et al., "Observed Changes in First Metatarsal and Medial Cuneiform Positions after First Metatarsophalangeal Joint Arthrodesis," The Journal of Foot and Ankle Surgery, vol. 53, 2014, pp. 32-35.

(56) References Cited

OTHER PUBLICATIONS

Dayton et al., "Reduction of the Intermetatarsal Angle after First Metatarsal Phalangeal Joint Arthrodesis: A Systematic Review," The Journal of Foot and Ankle Surgery, Article in Press, 2014, 4 pages.

Feilmeier et al., "Reduction of Intermetatarsal Angle after First Metatarsophalangeal Joint Arthrodesis in Patients with Hallux Valgus," The Journal of Foot and Ankle Surgery, vol. 53, 2014, pp. 29-31.

Dayton et al., "Principles of Management of Growth Plate Fractures in the Foot and Ankle," Clinics in Podiatric Medicine and Surgery, Pediatric Foot Deformities, Oct. 2013, 17 pages.

Dayton et al., "Observed Changes in Radiographic Measurements of the First Ray after Frontal and Transverse Plane Rotation of the Hallux: Does the Hallux Drive the Metatarsal in a Bunion Deformity?," The Journal of Foot and Ankle Surgery, Article in Press, 2014, 4 pages.

Rodriguez et al., "Ilizarov method of fixation for the management of pilon and distal tibial fractures in the compromised diabetic patient: A technique guide," The Foot and Ankle Journal Online, vol. 7, No. 2, 2014, 9 pages.

Feilmeier et al., "Incidence of Surgical Site Infection in the Foot and Ankle with Early Exposure and Showering of Surgical Sites: A Prospective Observation," The Journal of Foot and Ankle Surgery, vol. 53, 2014, pp. 173-175.

Catanese et al., "Measuring Sesamoid Position in Hallux Valgus: When Is the Sesamoid Axial View Necessary," Foot and Ankle Specialist, 2014, 3 pages.

Dayton et al., "Comparison of Complications for Internal and External Fixation for Charcot Reconstruction: A Systematic Review," The Journal of Foot and Ankle Surgery, Article in Press, 2015, 4 pages.

Dayton et al., "A new triplanar paradigm for bunion management," Lower Extremity Review, Apr. 2015, 9 pages.

Dayton et al., "American College of Foot and Ankle Surgeons' Clinical Consensus Statement: Perioperative Prophylactic Antibiotic Use in Clean Elective Foot Surgery," The Journal of Foot and Ankle Surgery, Article in Press, 2015, 7 pages.

Dayton et al., "Complications of Metatarsal Suture Techniques for Bunion Correction: A Systematic Review of the Literature," The Journal of Foot and Ankle Surgery, Article in Press, 2015, 3 pages.

DeCarbo et al., "The Weil Osteotomy: A Refresher," Techniques in Foot and Ankle Surgery, vol. 13, No. 4, Dec. 2014, pp. 191-198.

DeCarbo et al., "Resurfacing Interpositional Arthroplasty for Degenerative Joint Diseas of the First Metatarsalphalangeal Joint," Podiatry Management, Jan. 2013, pp. 137-142.

DeCarbo et al., "Locking Plates: Do They Prevent Complications?," Podiatry Today, Apr. 2014, 7 pages.

Easley et al., "Current Concepts Review: Hallux Valgus Part II: Operative Treatment," Foot and Ankle International, vol. 28, No. 6, Jun. 2007, pp. 748-758.

Kim et lal., "A Multicenter Retrospective Review of Outcomes for Arthrodesis, Hemi-Metallic Joint Implant, and Resectional Arthroplasty in the Surgical Treatment of End-Stage Hallux Rigidus," The Journal of Foot and Ankle Surgery, vol. 51, 2012, pp. 50-56.

Easley et al., "Current Concepts Review: Hallux Valgus Part I: Pathomechanics, Clinical Assessment, and Nonoperative Management," Foot and Ankle International, vol. 28, No. 5, May 2007, pp. 654-659.

Sandhu et al., "Digital Arthrodesis With a One-Piece Memory Nitinol Intramedullary Fixation Device: A Retrospective Review," Foot and Ankle Specialist, vol. 6, No. 5, Oct. 2013, pp. 364-366.

Weber et al., "Use of the First Ray Splay Test to Assess Transverse Plane Instability Before First Metatarsocuneiform Fusion," The Journal of Foot and Ankle Surgery, vol. 45, No. 4, Jul./Aug. 2006, pp. 278-282.

Smith et al., "Opening Wedge Osteotomies for Correction of Hallux Valgus: A Review of Wedge Plate Fixation," Foot and Ankle Specialist, vol. 2, No. 6, Dec. 2009, pp. 277-282.

Easley et al., "What is the Best Treatment for Hallux Valgus?," Evidence-Based Orthopaedics—The Best Answers to Clinical Questions, Chapter 73, 2009, pp. 479-491.

Shurnas et al., "Proximal Metatarsal Opening Wedge Osteotomy," Operative Techniques in Foot and Ankle Surgery, Section I, Chapter 13, 2011, pp. 73-78.

Coetzee et al., "Revision Hallux Valgus Correction," Operative Techniques in Foot and Ankle Surgery, Section I, Chapter 15, 2011, pp. 84-96.

Le et al., "Tarsometatarsal Arthrodesis," Operative Techniques in Foot and Ankle Surgery, Section II, Chapter 40, 2011, pp. 281-285.

Collan et al., "The biomechanics of the first metatarsal bone in hallux valgus: A preliminary study utilizing a weight bearing extremity CT," Foot and Ankle Surgery, vol. 19, 2013, pp. 155-161.

Eustace et al., "Hallux valgus, first metatarsal pronation and collapse of the medial longitudinal arch—a radiological correlation," Skeletal Radiology, vol. 23, 1994, pp. 191-194.

Mizuno et al., "Detorsion Osteotomy of the First Metatarsal Bone in Hallux Valgus," Japanese Orthopaedic Association, Tokyo, 1956; 30:813-819.

Okuda et al., "The Shape of the Lateral Edge of the First Metatarsal Head as a Risk Factor for Recurrence of Hallux Valgus," The Journal of Bone and Joint Surgery, vol. 89, 2007, pp. 2163-2172.

Okuda et al., "Proximal Metatarsal Osteotomy for Hallux Valgus: Comparison of Outcome for Moderate and Severe Deformities," Foot and Ankle International, vol. 29, No. 7, Jul. 2008, pp. 664-670.

D'Amico et al., "Motion of the First Ray: Clarification Through Investigation," Journal of the American Podiatry Association, vol. 69, No. 1, Jan. 1979, pp. 17-23.

Groves, "Operative Report," St. Tammany Parish Hospital, Date of Procedure, Mar. 26, 2014, 2 pages.

Claim Chart for Groves Public Use (Mar. 26, 2014), Exhibit B4 of Defendant Fusion Orthopedics LLC's Invalidity Contentions, No. CV-22-00490-PHX-SRB, US District Court for the District of Arizona, Aug. 27, 2022, 161 pages.

"Accu-Cut Osteotomy Guide System," BioPro, Brochure, Oct. 2018, 2 pages.

"Acumed Osteotomiesystem Operationstechnik," Acumed, 2014, 19 pages (including 3 pages English translation).

Albano et al., "Biomechanical Study of Transcortical or Transtrabecular Bone Fixation of Patellar Tendon Graft wih Bioabsorbable Pins in ACL Reconstruction in Sheep," Revista Brasileira de Ortopedia (Rev Bras Ortop.) vol. 47, No. 1. 2012, pp. 43-49.

Alvine et al., "Peg and Dowel Fusion of the Proximal Interphalangeal Joint," Foot & Ankle, vol. 1, No. 2, 1980, pp. 90-94.

Anderson et al., "Uncemented Star Total Ankle Prostheses," The Journal of Bone and Joint Surgery, vol. 86(1, Suppl 2), Sep. 2004, pp. 103-111, (Abstract Only).

Bednarz et al., "Modified Lapidus Procedure for the Treatment of Hypermobile Hallux Valgus," Foot & Ankle International, vol. 21, No. 10, Oct. 2000, pp. 816-821.

Blomer, "Knieendoprothetik—Herstellerische Probleme und technologische Entwicklungen," Orthopade, vol. 29, 2000, pp. 688-696, including English Abstract on p. 689.

Bouaicha et al., "Fixation of Maximal Shift Scarf Osteotomy with Inside-Out Plating: Technique Tip," Foot & Ankle International, vol. 32, No. 5, May 2011, pp. 567-569.

Carr et al., "Correctional Osteotomy for Metatarsus Primus Varus and Hallux Valgus," The Journal of Bone and Joint Surgery, vol. 50-A, No. 7, Oct. 1968, pp. 1353-1367.

Coetzee et al., "The Lapidus Procedure: A Prospective Cohort Outcome Study," Foot & Ankle International, vol. 25, No. 8, Aug. 2004, pp. 526-531.

Dayton et al., "Is Our Current Paradigm for Evaluation and Management of the Bunion Deformity Flawed? A Discussion of Procedure Philosophy Relative to Anatomy," The Journal of Foot and Ankle Surgery, vol. 54, 2015, pp. 102-111.

Dayton et al., "Observed Changes in Radiographic Measurements of the First Ray after Frontal and Transverse Plane Rotation of the Hallux: Does the Hallux Drive the Metatarsal in a Bunion Deformity?," The Journal of Foot and Ankle Surgery, vol. 53, 2014, pp. 584-587.

(56) References Cited

OTHER PUBLICATIONS

Dayton et al., "Relationship Of Frontal Plane Rotation Of First Metatarsal To Proximal Articular Set Angle And Hallux Alignment In Patients Undergoing Tarsometatarsal Arthrodesis For Hallux Abducto Valgus: A Case Series And Critical Review Of The Literature," The Journal of Foot and Ankle Surgery, vol. 52, No. 3, May/Jun. 2013, pp. 348-354.
Dayton et al., "Quantitative Analysis of the Degree of Frontal Rotation Required to Anatomically Align the First Metatarsal Phalangeal Joint During Modified Tarsal-Metatarsal Arthrodesis Without Capsular Balancing," The Journal of Foot and Ankle Surgery, 2015, pp. 1-6.
De Geer et al., "A New Measure of Tibial Sesamoid Position in Hallux Valgus in Relation to the Coronal Rotation of the First Metatarsal in CT Scans," Foot and Ankle International, Mar. 26, 2015, 9 pages.
DiDomenico et al., "Correction of Frontal Plane Rotation of Sesamoid Apparatus during the Lapidus Procedure: A Novel Approach," The Journal of Foot and Ankle Surgery, vol. 53, 2014, pp. 248-251.
Dobbe et al. "Patient-Tailored Plate For Bone Fixation And Accurate 3D Positioning In Corrective Osteotomy," Medical and Biological Engineering and Computing, vol. 51, No. 1-2, Feb. 2013, pp. 19-27, (Abstract Only).
Doty et al., "Hallux valgus and hypermobility of the first ray: facts and fiction," International Orthopaedics, vol. 37, 2013, pp. 1655-1660.
EBI Extra Small Rail Fixator, Biomet Trauma, retrieved Dec. 19, 2014, from the Internet: < http://footandanklefixation.com/product/biomet-trauma-ebi-extra-small-rail-fixator>, 7 pages.
Dayton et al., "Comparison of the Mechanical Characteristics of a Universal Small Biplane Plating Technique Without Compression Screw and Single Anatomic Plate With Compression Screw," The Journal of Foot & Ankle Surgery, vol. 55, No. 3, May/Jun. 2016, published online: Feb. 9, 2016, pp. 567-571.
"Futura Forefoot Implant Arthroplasty Products," Tornier, Inc., 2008, 14 pages.
Galli et al., "Enhanced Lapidus Arthrodesis: Crossed Screw Technique With Middle Cuneiform Fixation Further Reduces Sagittal Mobility," The Journal of Foot & Ankle Surgery, vol. 54, vol. 3, May/Jun. 2015, published online: Nov. 21, 2014, pp. 437-440.
Garthwait, "Accu-Cut System Facilitates Enhanced Precision," Podiatry Today, vol. 18, No. 6, Jun. 2005, 6 pages.
Gonzalez Del Pino et al., "Variable Angle Locking Intercarpal Fusion System for Four-Corner Arthrodesis: Indications and Surgical Technique," Journal of Wrist Surgery, vol. 1, No. 1, Aug. 2012, pp. 73-78.
Gotte, "Entwicklung eines Assistenzrobotersystems für die Knieendoprothetik," Forschungsberichte, Technische Universitat Munchen, 165, 2002, 11 pages, including partial English Translation.
Gregg et al., "Plantar plate repair and Weil osteotomy for metatarsophalangeal joint instability," Foot and Ankle Surgery, vol. 13, 2007, pp. 116-121.
Grondal et al., "A Guide Plate for Accurate Positioning of First Metatarsophalangeal Joint during Fusion," Operative Orthopädie Und Traumatologie, vol. 16, No. 2, 2004, pp. 167-178 (Abstract Only).
"Hat-Trick Lesser Toe Repair System," Smith & Nephew, Brochure, Aug. 2014, 12 pages.
"Hat-Trick Lesser Toe Repair System, Foot and Ankle Technique Guide, Metatarsal Shortening Osteotomy Surgical Technique," Smith & Nephew, 2014, 16 pages.

Etherington et al., "Evaluation of surgical experience and the use of an osteotomy guide on the apical angle of an Austin osteotomy," The Foot, vol. 18, 2008, pp. 159-164.
Hirao et al., "Computer assisted planning and custom-made surgical guide for malunited pronation deformity after first metatarsophalangeal joint arthrodesis in rheumatoid arthritis: A case report," Computer Aided Surgery, vol. 19, Nos. 1-3, 2014, pp. 13-19.
"Hoffmann II Compact External Fixation System," Stryker, Brochure, Literature No. 5075-1-500, 2006, 12 pages.
"Hoffmann II Micro Lengthener," Stryker, Operative Technique, Literature No. 5075-2-002, 2008, 12 pages.
"Hoffmann Small System External Fixator Orthopedic Instruments," Stryker, retrieved Dec. 19, 2014, from the Internet: <http://www.alibaba.com/product-detail/Stryker-Hoffmann-Small-System-External-Fixator_1438850129.html>, 3 pages.
Mortier et al., "Axial Rotation of the First Metatarsal Head in a Normal Population and Hallux Valgus Patients," Orthopaedics and Traumatology: Surgery and Research, vol. 98, 2012, pp. 677-683.
Kim et al., "A New Measure of Tibial Sesamoid Position in Hallux Valgus in Relation to the Coronal Rotation of the First Metatarsal in CT Scans," Foot and Ankle International, vol. 36, No. 8, 2015, pp. 944-952.
"Lag Screw Target Bow," Stryker Leibinger GmbH & Co. KG, Germany 2004, 8 pages.
Lapidus, "The Author's Bunion Operation From 1931 to 1959," Clinical Orthopaedics, vol. 16, 1960, pp. 119-135.
Lieske et al., "Implantation einer Sprunggelenktotalendo-prothese vom Typ Salto 2," Operative Orthopädie und Traumatologie, vol. 26, No. 4, 2014, pp. 401-413, including English Abstract on p. 403.
MAC (Multi Axial Correction) Fixation System, Biomet Trauma, retrieved Dec. 19, 2014, from the Internet: <http://footandanklefixation.com/product/biomet-trauma-mac-multi-axial-correction-fixation-system>, 7 pages.
Magin, "Computernavigierter Gelenkersatz am Knie mit dem Orthopilot," Operative Orthopädie und Traumatologie, vol. 22, No. 1, 2010, pp. 63-80, including English Abstract on p. 64.
Magin, "Die belastungsstabile Lapidus-Arthrodese bei Hallux-valgus-Deformität mittels IVP-Plattenfixateur (V-TEK-System)," Operative Orthopädie und Traumatologie, vol. 26, No. 2, 2014, pp. 184-195, including English Abstract on p. 186.
Mini Joint Distractor, Arthrex, retrieved Dec. 19, 2014, from the Internet: <http://www.arthrex.com/foot-ankle/mini-joint-distractor/products>, 2 pages.
MiniRail System, Small Bone Innovations, Surgical Technique, 2010, 24 pages.
Miyake et al., "Three-Dimensional Corrective Osteotomy for Malunited Diaphyseal Forearm Fractures Using Custom-Made Surgical Guides Based on Computer Simulation," JBJS Essential Surgical Techniques, vol. 2, No. 4, 2012, 11 pages.
Modular Rail System: External Fixator, Smith & Nephew, Surgical Technique, 2013, 44 pages.
Monnich et al., "A Hand Guided Robotic Planning System for Laser Osteotomy in Surgery," World Congress on Medical Physics and Biomedical Engineering vol. 25/6: Surgery, Nimimal Invasive Interventions, Endoscopy and Image Guided Therapy, Sep. 7-12, 2009, pp. 59-62, (Abstract Only).
Moore et al., "Effect Of Ankle Flexion Angle On Axial Alignment Of Total Ankle Replacement," Foot and Ankle International, vol. 31, No. 12, Dec. 2010, pp. 1093-1098, (Abstract Only).
Dayton et al., "Evidence-Based Bunion Surgery: A Critical Examination of Current and Emerging Concepts and Techniques," Springer International Publishing, 2017, 254 pages.

\* cited by examiner

TARSAL-METATARSAL JOINT PROCEDURE UTILIZING COMPRESSOR-DISTRACTOR AND INSTRUMENT PROVIDING SLIDING SURFACE

RELATED APPLICATIONS

This application is a continuation of U.S. application Ser. No. 16/784,742, filed Feb. 7, 2020, which claims the benefit of U.S. Provisional Application No. 62/805,208 filed Feb. 13, 2019. The entire contents of each of these applications are incorporated herein by reference.

TECHNICAL FIELD

This disclosure relates generally to devices and techniques for repositioning bones and, more particularly, to devices and techniques for repositioning bones in the foot.

BACKGROUND

Bones within the human body, such as bones in the foot, may be anatomically misaligned. For example, one common type of bone deformity is hallux valgus, which is a progressive foot deformity in which the first metatarsophalangeal joint is affected and is often accompanied by significant functional disability and foot pain. The metatarsophalangeal joint is laterally deviated, resulting in an abduction of the first metatarsal while the phalanges adduct. This often leads to development of soft tissue and a bony prominence on the medial side of the foot, which is called a bunion.

Surgical intervention may be used to correct a bunion deformity. A variety of different surgical procedures exist to correct bunion deformities and may involve removing the abnormal bony enlargement on the first metatarsal and/or attempting to realign the first metatarsal relative to the adjacent metatarsal. Surgical instruments that can facilitate efficient, accurate, and reproducible clinical results are useful for practitioners performing bone realignment techniques.

SUMMARY

In general, this disclosure is directed to devices and techniques that can be used during a surgical bone realignment procedure. In some examples, a system is described that includes a compressor-distractor device and an instrument defining a sliding surface. The compressor-distractor device and the instrument defining the sliding surface can be utilized together during a bone repositioning procedure. For example, during a bone repositioning procedure, a bone such as a metatarsal on a foot may be moved from an anatomically misaligned position to an anatomically aligned position with respect to another bone, such as an adjacent metatarsal. One end of the metatarsal and a facing end of adjacent cuneiform may be prepared, such as by cutting the ends of the metatarsal and adjacent cuneiform.

To facilitate clean-up and compression between the two bone ends, the compressor-distractor device may be attached to both the metatarsal and cuneiform. The compressor-distractor device can then be actuated to move the metatarsal away from the cuneiform. This can open up the space between the two bone faces, for example, to allow the clinician to preform further cleanup and/or preparation on a bone face and/or to remove debris from the space between the two bone faces. In either case, the compressor-distractor device can be actuated to move the metatarsal toward the cuneiform, for example, to compress the two bone faces together for fixation. As the metatarsal is moved toward the cuneiform, the prepared end face and/or a side of the metatarsal may have a tendency to catch or frictionally interfere with adjacent bone and/or tissue. For this and other reasons, an instrument defining a sliding surface according to the disclosure may be utilized with the compressor-distractor device. The instrument may be positioned between the prepared metatarsal and an adjacent metatarsal. For example, the instrument may be positioned between the prepared end face and/or a lateral side of the metatarsal and an adjacent metatarsal. The sliding surface defined by the instrument may provide a comparatively low friction surface (e.g., compared to otherwise interfering tissue and/or bone) against which the metatarsal can slide as it is moving toward the cuneiform. For example, the sliding surface defined by the instrument can be a laterally-positioned bearing surface against which the metatarsal can slide as the metatarsal is moved generally axially (e.g., in the proximal direction).

In some implementations, the instrument defining the sliding surface may be positioned substantially stationary (non-moving) as the metatarsal is moved generally axially toward an opposing cuneiform. In other implementations, the instrument defining the sliding surface may be moved as the metatarsal is moved generally axially toward an opposing cuneiform. For example, the clinician may grasp or otherwise hold the instrument defining the sliding surface and manipulate the position of the instrument as the metatarsal is compressed toward and/or against the opposing cuneiform. The clinician may move the instrument toward the opposing cuneiform (e.g., parallel to the metatarsal being moved) at the same rate as the metatarsal is being moved or at a different rate than the rate at which the metatarsal is being moved. Accordingly, the metatarsal being moved may or may not move relative to the instrument defining the sliding surface as both the instrument and the metatarsal are moved (e.g., proximally). In some applications, the clinician may bias (e.g., push) the instrument defining the sliding surface medially while moving the metatarsal generally axially toward the opposing cuneiform. This medial biasing force can help deflect and redirect the metatarsal being moved into alignment with the opposing cuneiform, as the metatarsal being moved may have a tendency to shift laterally during movement.

A compressor-distractor used according to the present disclosure can have a variety of different configurations. In some examples, the compressor-distractor includes first and second engagement arms that define first and second pin-receiving holes, respectively. The first and second pin-receiving holes can receive pins that are inserted into adjacent bones being compressed and/or distracted. In this way, the pins inserted through the pin-receiving holes can function to attach to the compressor-distractor to the bones. The first and second pin-receiving holes can be parallel to each other, e.g., to facilitate sliding the compressor-distractor on and/or off the pins without adjusting the relative positioning of the pins. Alternatively, the first and second pin-receiving holes can be angled relative to each other. This may cause the pins and, correspondingly bones to which the pins are attached, to rotate as the compressor-distractor is placed over the pins.

The instrument defining the sliding surface according to the disclosure can likewise have a variety of different configurations. In general, any mechanical instrument that provides separation between adjacent bones and a surface against which one bone can slide can function as an instrument defining a sliding surface according to the disclosure.

In some examples, the instruction providing the sliding surface is also used as a fulcrum providing pivot surface about which a bone is rotated during the procedure. For example, during realignment of one metatarsal relative to an adjacent metatarsal, a distal portion of the one metatarsal may be moved toward the second metatarsal in a transverse plane. By positioning the instrument between the two metatarsals, the proximal portion of the one metatarsal may be pivoted about the fulcrum, reducing the intermetatarsal angle between the metatarsals. In this regard, the instrument defining the sliding surface may also function as a fulcrum.

In some implementations, the instrument defining the sliding surface includes a body and a handle. The body is configured to be inserted in an intermetatarsal space between adjacent metatarsals. The handle is operatively connected to the body. The handle may project at a non-zero degree angle from the body to define a tissue retraction space between the handle and the body. Other instrument and/or handle configurations can be used though, and it should be appreciated that the disclosure is not limited in this respect.

The system that includes the compressor-distractor and instrument defining the sliding surface may be used during a surgical procedure in which one or more other surgical instruments are also used. For example, the compressor-distractor and sliding surface instrument may be used during a procedure in which a bone preparation guide is also deployed for preparing the bones that are to be subsequent distracted and/or compressed together using the compressor-distractor and sliding surface instrument. The bone preparation guide may be pinned to two different bone portions, which may be two different bones separated by a joint or two portions of the same bone (e.g., separated by a fracture or break). In either case, one end of the bone preparation guide may be pinned to one bone portion while another end of the bone preparation guide may be pinned to the other bone portion. The bone preparation guide may be pinned to the two bone portions using a pair of pins that extend parallel to each other through a pair of fixation apertures on the bone preparation guide, optionally along with one or more additional pins that may extend through one or more additional fixation apertures on the bone preparation guide that may be skewed or angled at a non-zero degree angle relative to the parallel pins. In some configurations, the bone preparation guide defines one or more slots through which a bone preparation instrument (e.g., cutting instrument) is inserted to prepare opposed end faces of the two bones.

After utilizing the bone preparation guide to prepare the two bone portions, the clinician may remove any angled pins (e.g., non-parallel pins) inserted through the bone preparation guide into the bone portions, leaving the parallel-aligned pins (e.g., a pair of parallel pins) in the bone portions. The bone preparation guide can be slide or translated along the parallel-aligned pins until the fixation apertures of the bone preparation guide come off the distal ends of the pins. At this point, the bone preparation guide may be separated from the pins, leaving the pins in the bone portions. The compressor-distractor can then be installed over the pins by threading the parallel-aligned pins through the first and second pin-receiving holes of the compressor-distractor.

After installing the compressor-distractor on the pins, the clinician may actuate the actuator to move the first and second engagement arms away from each other and, as a result, move the bone portions away from each other. This can provide an enlarged separation gap between the bone portions for cleaning the inter-bone space in anticipation of fixation. For example, the clinician may remove bone chips and/or tissue debris from the inter-bone space between the two bone portions, further cut or prepare an end face of one or both bone portions, or otherwise prepare for fixation.

Before or after distracting the two bone portions, the clinician may insert the instrument defining the sliding surface between a bone portion that is or will be distracted and an adjacent bone to the bone portion that is or will be distracted. For example, the clinician may insert the instrument defining the sliding surface between a metatarsal that is or will be distracted from a cuneiform and an adjacent metatarsal (e.g., laterally-adjacent metatarsal). The opposite side of the instrument from the side defining the sliding surface may or may not contact the adjacent metatarsal. When subsequently actuating the compressor-distractor, the distracted metatarsal may move proximally toward the cuneiform to close the space between the metatarsal and the cuneiform. As the distracted metatarsal is moved proximally, the metatarsal can contact and/or slide along the sliding surface positioned between the metatarsal and adjacent metatarsal. This provision of the sliding surface can help facilitate smooth compression of the metatarsal to the cuneiform and/or help prevent movement of the metatarsal being compressed in the frontal and/or transverse planes during compression.

In some applications, the clinician can insert the instrument defining the sliding surface between a metatarsal that is or will be distracted from a cuneiform and an adjacent metatarsal and leave the instrument in a substantially fixed position as the metatarsal is moved toward an opposed cuneiform. In other applications, the clinician may move the instrument defining the sliding surface with the metatarsal as the metatarsal is moved toward the opposed cuneiform. Accordingly, the instrument defining the sliding surface may slide proximally with the metatarsal being moved to contact and/or compress against the opposed cuneiform.

In practice, the clinician may move the first and second engagement arms of the compressor-distractor toward each other until the end faces of the bone portions are pressing against each other, resulting in a compressive force being applied to the bone portions. In some example, the clinician then fixates the bone portions by applying one or more fixation members to the bone portions.

In one example, a method is described that includes attaching a compressor-distractor to a first metatarsal and attaching the compressor-distractor to a medial cuneiform. The method includes actuating the compressor-distractor to move the first metatarsal away from the medial cuneiform and inserting an instrument defining a sliding surface between the first metatarsal and a second metatarsal. The method further involves actuating the compressor-distractor to move the first metatarsal toward the medial cuneiform, thereby causing the first metatarsal to slide across the sliding surface of the instrument as the first metatarsal is moved toward the medial cuneiform.

The details of one or more examples are set forth in the accompanying drawings and the description below. Other features, objects, and advantages will be apparent from the description and drawings, and from the claims.

The details of one or more examples are set forth in the accompanying drawings and the description below. Other features, objects, and advantages will be apparent from the description and drawings, and from the claims.

DETAILED DESCRIPTION

In general, the present disclosure is directed to devices and techniques for correcting a misalignment of one or more bones. The disclosed devices and techniques can be implemented in a surgical procedure in which one bone portion is realigned relative to another bone portion. In some examples, the technique is performed on one or more bones in the foot or hand, where bones are relatively small compared to bones in other parts of the human anatomy. For example, the foregoing description generally refers to example techniques performed on the foot and, more particularly a metatarsal and cuneiform of the foot. However, the disclosed techniques may be performed on other bones, such as the tibia, fibula, ulna, humerus, femur, or yet other bone, and the disclosure is not limited in this respect unless otherwise specifically indicated. In some applications, however, the disclosed techniques are used to correct a misalignment between a metatarsal (e.g., a first metatarsal) and a second metatarsal and/or a cuneiform (e.g., a medial, or first, cuneiform), such as in a bunion correction surgery.

Figure 1B:
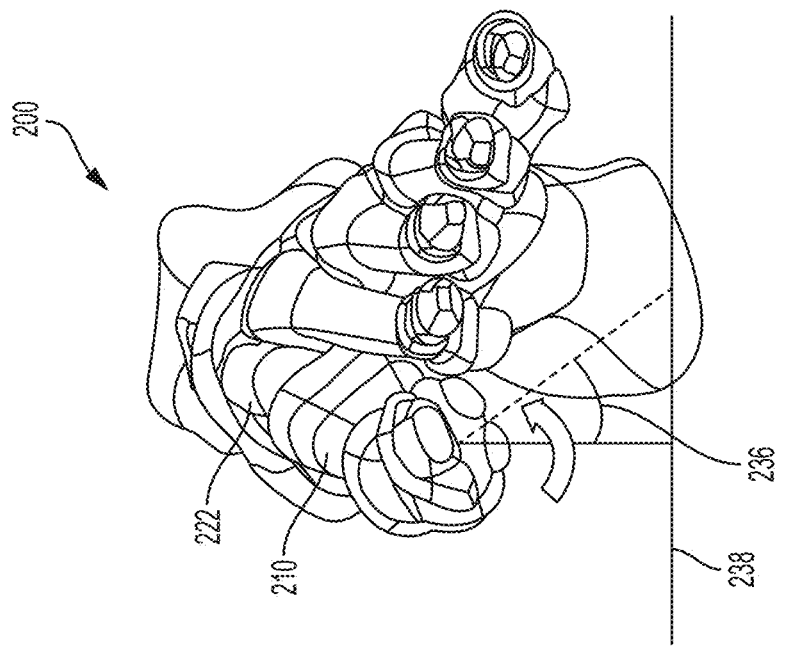
FIGS. 1A and 1B are front views of a foot showing a normal first metatarsal position and an example frontal plane rotational misalignment position, respectively.
Figure 1A:
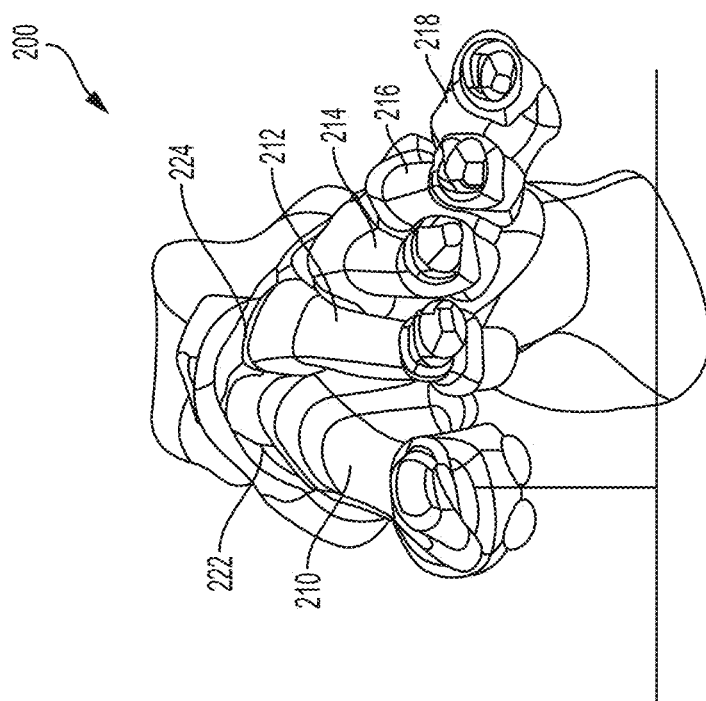
Figure 2B:
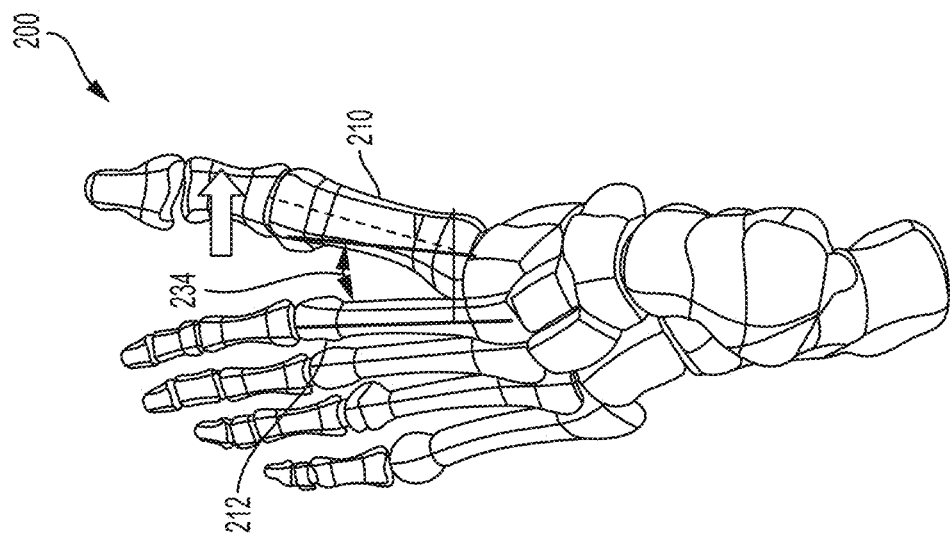
FIGS. 2A and 2B are top views of a foot showing a normal first metatarsal position and an example transverse plane misalignment position, respectively.
Figure 2A:
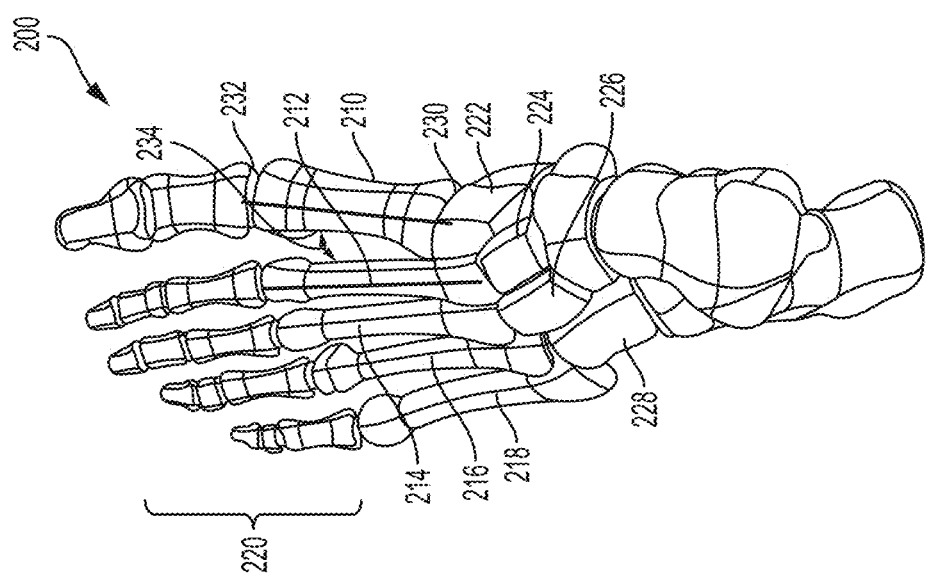
Figure 3B:
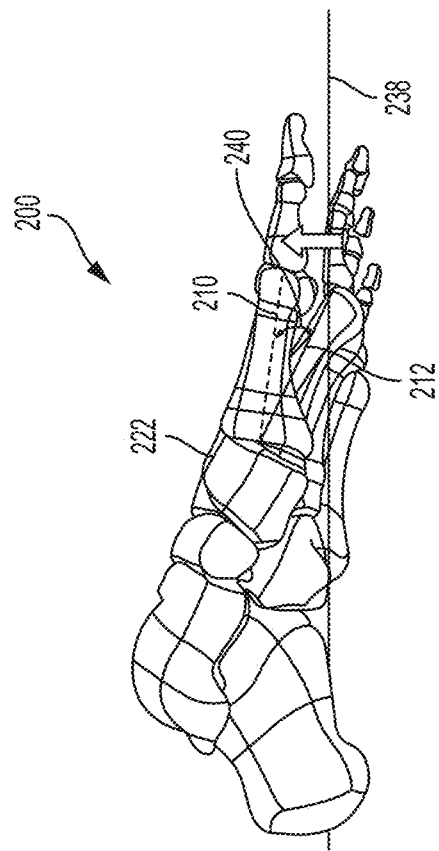
FIGS. 3A and 3B are side views of a foot showing a normal first metatarsal position and an example sagittal plane misalignment position, respectively.
Figure 3A:
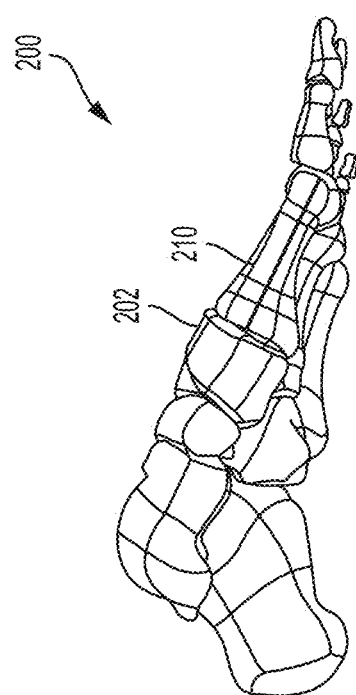

FIGS. 1-3 are different views of a foot 200 showing example anatomical misalignments that may occur and be corrected according to the present disclosure. Such misalignment may be caused by a hallux valgus (bunion), natural growth deformity, or other condition causing anatomical misalignment. FIGS. 1A and 1B are front views of foot 200 showing a normal first metatarsal position and an example frontal plane rotational misalignment position, respectively. FIGS. 2A and 2B are top views of foot 200 showing a normal first metatarsal position and an example transverse plane misalignment position, respectively. FIGS. 3A and 3B are side views of foot 200 showing a normal first metatarsal position and an example sagittal plane misalignment position, respectively. While FIGS. 1B, 2B, and 3B show each respective planar misalignment in isolation, in practice, a metatarsal may be misaligned in any two of the three planes or even all three planes. Accordingly, it should be appreciated that the depiction of a single plane misalignment in each of FIGS. 1B, 2B, and 3B is for purposes of illustration and a metatarsal may be misaligned in multiple planes that is desirably corrected.

With reference to FIGS. 1A and 2A, foot 200 is composed of multiple bones including a first metatarsal 210, a second metatarsal 212, a third metatarsal 214, a fourth metatarsal 216, and a fifth metatarsal 218. The metatarsals are connected distally to phalanges 220 and, more particularly, each to a respective proximal phalanx. The first metatarsal 210 is connected proximally to a medial cuneiform 222, while the second metatarsal 212 is connected proximally to an intermediate cuneiform 224 and the third metatarsal is connected proximally to lateral cuneiform 226. The fourth and fifth metatarsals 216, 218 are connected proximally to the cuboid bone 228. The joint 230 between a metatarsal and respective cuneiform (e.g., first metatarsal 210 and medial cuneiform 222) is referred to as the tarsometatarsal ("TMT") joint. The joint 232 between a metatarsal and respective proximal phalanx is referred to as a metatarsophalangeal joint. The angle 234 between adjacent metatarsals (e.g., first metatarsal 210 and second metatarsal 212) is referred to as the inter-metatarsal angle ("IMA").

As noted, FIG. 1A is a frontal plane view of foot 200 showing a typical position for first metatarsal 210. The frontal plane, which is also known as the coronal plane, is generally considered any vertical plane that divides the body into anterior and posterior sections. On foot 200, the frontal plane is a plane that extends vertically and is perpendicular to an axis extending proximally to distally along the length of the foot. FIG. 1A shows first metatarsal 210 in a typical rotational position in the frontal plane. FIG. 1B shows first metatarsal 210 with a frontal plane rotational deformity characterized by a rotational angle 236 relative to ground, as indicated by line 238.

FIG. 2A is a top view of foot 200 showing a typical position of first metatarsal 210 in the transverse plane. The transverse plane, which is also known as the horizontal plane, axial plane, or transaxial plane, is considered any plane that divides the body into superior and inferior parts. On foot 200, the transverse plane is a plane that extends horizontally and is perpendicular to an axis extending dorsally to plantarly (top to bottom) across the foot. FIG. 2A shows first metatarsal 210 with a typical IMA 234 in the transverse plane. FIG. 2B shows first metatarsal 210 with a transverse plane rotational deformity characterized by a greater IMA caused by the distal end of first metatarsal 210 being pivoted medially relative to the second metatarsal 212.

FIG. 3A is a side view of foot 200 showing a typical position of first metatarsal 210 in the sagittal plane. The sagittal plane is a plane parallel to the sagittal suture which divides the body into right and left halves. On foot 200, the sagittal plane is a plane that extends vertically and is perpendicular to an axis extending proximally to distally along the length of the foot. FIG. 3A shows first metatarsal 210 with a typical rotational position in the sagittal plane. FIG. 3B shows first metatarsal 210 with a sagittal plane rotational deformity characterized by a rotational angle 240 relative to ground, as indicated by line 238.

A system and technique that utilizes a compressor-distractor and instrument defining a sliding surface according to the disclosure can be useful during a bone positioning procedure, for example, to correct an anatomical misalignment of a bones or bones. In some applications, the compressor-distractor can help establish and/or maintain a realignment between a metatarsal and an adjacent cuneiform. Additionally or alternatively, the compressor-distractor can facilitate clean-up and compression between adjacent bone portions between fixation. The instrument defining the sliding surface can help facilitate compression of the bone portions after clean-up, e.g., by helping to prevent the bone portion being compressed from catching or hanging up on adjacent tissue and/or bone during compression, which move the bone portion being compressed out of a desired alignment.

The metatarsal undergoing realignment may be anatomically misaligned in the frontal plane, transverse plane, and/or sagittal plane, as illustrated and discussed with respect to FIGS. 1-3 above. Accordingly, realignment may involve releasing the misaligned metatarsal for realignment and thereafter realigning the metatarsal in one or more planes, two or more planes, or all three planes. After suitably realigning the metatarsal, the metatarsal can be fixated to hold and maintain the realigned positioned.

While a metatarsal can have a variety of anatomically aligned and misaligned positions, in some examples, the term "anatomically aligned position" means that an angle of a long axis of first metatarsal 210 relative to the long axis of second metatarsal 212 is about 10 degrees or less (e.g., 9 degrees or less) in the transverse plane and/or sagittal plane. In certain embodiments, anatomical misalignment can be corrected in both the transverse plane and the frontal plane. In the transverse plane, a normal IMA 234 between first metatarsal 210 and second metatarsal 212 is less than about 9 degrees. An IMA 234 of between about 9 degrees and about 13 degrees is considered a mild misalignment of the first metatarsal and the second metatarsal. An IMA 234 of greater than about 16 degrees is considered a severe misalignment of the first metatarsal and the second metatarsal. In some embodiments, methods and/or devices according to the disclosure are utilized to anatomically align first metatarsal 210 by reducing the IMA from over 10 degrees to about 10 degrees or less (e.g., to an IMA of 9 degrees or less, or an IMA of about 1-5 degrees), including to negative angles of about −5 degrees or until interference with the second metatarsal, by positioning the first metatarsal at a different angle with respect to the second metatarsal.

With respect to the frontal plane, a normal first metatarsal will be positioned such that its *crista* prominence is generally perpendicular to the ground and/or its sesamoid bones are generally parallel to the ground and positioned under the metatarsal. This position can be defined as a metatarsal rotation of 0 degrees. In a misaligned first metatarsal, the metatarsal may be axially rotated between about 4 degrees to about 30 degrees or more. In some embodiments, methods and/or devices according to the disclosure are utilized to anatomically align the metatarsal by reducing the metatarsal rotation from about 4 degrees or more to less than 4 degrees (e.g., to about 0 to 2 degrees) by rotating the metatarsal with respect to the adjacent cuneiform.

A compressor-distractor according to the disclosure may be useful to distract a misaligned metatarsal from an adjacent cuneiform to provide access to the end faces of the bones and/or tarsometatarsal joint. The compressor-distractor may also be useful to apply a compressive force to the metatarsal and adjacent cuneiform (e.g., after preparing the end faces of the bones) to press the bones together to facilitate fixation. Additionally or alternatively, the compressor-distractor may impart and/or maintain relative movement between the metatarsal and adjacent cuneiform, such as rotation and/or pivoting of one bone relative to the other bone. For example, the compressor-distractor may be configured with an angular offset between pin-receiving holes, which may be effective to move the metatarsal from an anatomically misaligned position to an anatomically aligned position. As the compressor-distractor is translated over pins inserted into the metatarsal and cuneiform, the angular offset of the pin-receiving holes may cause the pins to move from being generally parallel to an angular alignment dictated by the pin-receiving holes. The resulting movement of the metatarsal relative to cuneiform caused by this movement can help position the metatarsal in an aligned position.

In other configurations, however, the compressor-distractor may not move the metatarsal from an anatomically misaligned position to an anatomically aligned position. Rather, the compressor-distractor may be configured to distract and compress a metatarsal relative to an adjacent cuneiform without performing rotating and/or pivoting the metatarsal relative to an adjacent cuneiform. For example, the compressor-distractor may have pin-receiving holes that are not angular offset relative to each other. In these implementations, the compressor-distractor can be attached and/or removed from the metatarsal relative and adjacent cuneiform without intended to rotate and/or pivot the metatarsal relative to the cuneiform.

A variety of different instruments defining sliding surfaces can be used in the systems and techniques according to the present disclosure. Example instruments that may provide a sliding surface include, but are not limited to, a surgical pin or rod, a screw driver head/shaft, an osteotome, or a retractor. Depending on the instrument used, the instrument may have a variety of cross-sectional shapes, such as a generally polygonal shape (e.g., square, hexagonal), a generally arcuate shape (e.g., circular, elliptical), or combinations of polygonal and arcuate shapes. Example instruments are described in greater detail below with respect to FIGS. 8-13.

An example technique utilizing a compressor-distractor and instrument providing a sliding surface will be described in greater detail below with respect to FIGS. 16-25. However, example compressor-distractor configurations that may be used according to the disclosure will first be described with respect to FIGS. 4-7.

Figure 4:
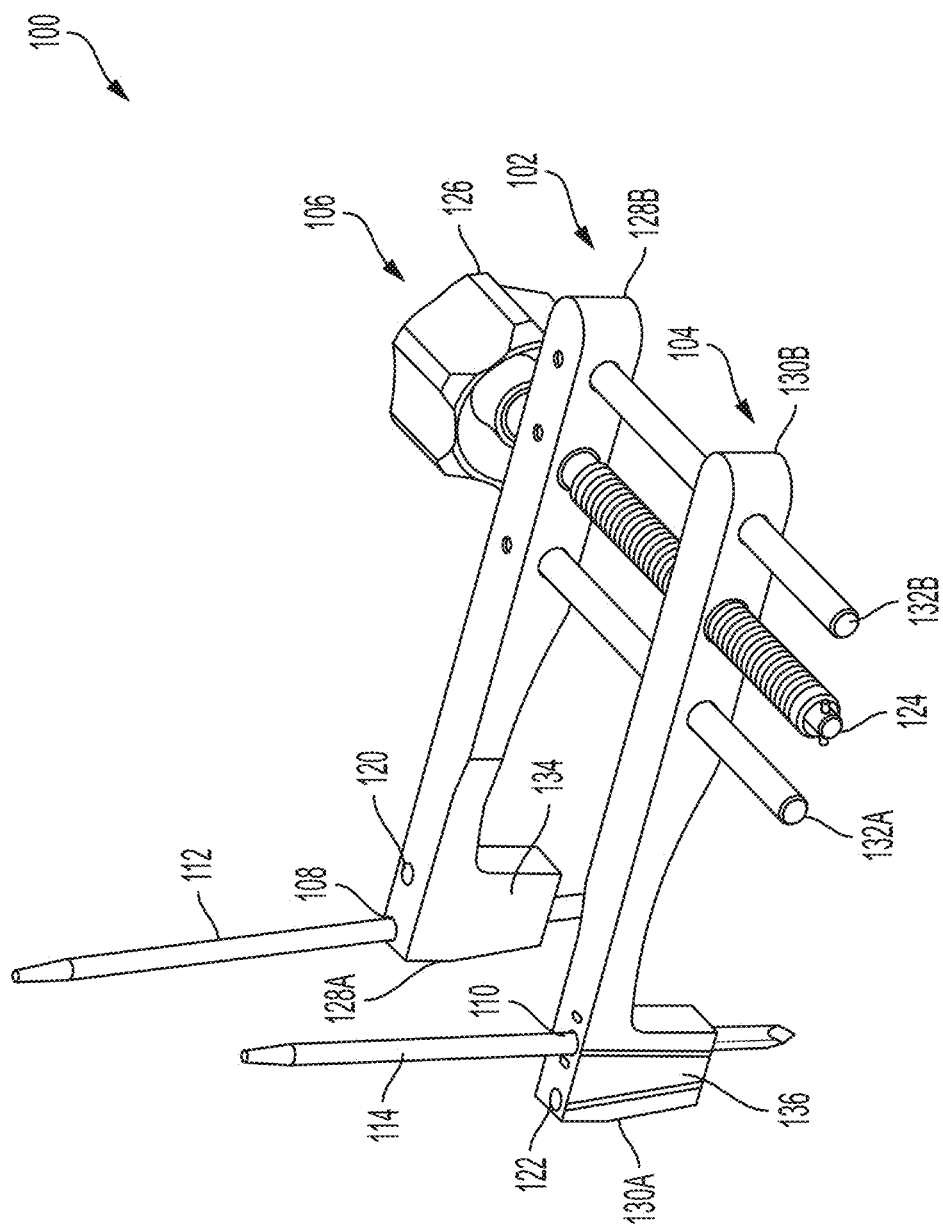
FIG. 4 is a perspective view of an example compressor-distractor according to disclosure.

FIG. 4 is a perspective view of an example compressor-distractor 100 that can be used in systems and techniques according to disclosure. Compressor-distractor 100 is illustrated as having a first engagement arm 102 and a second engagement arm 104. Compressor-distractor 100 also includes an actuator 106 that is operably coupled to the first engagement arm 102 and the second engagement arm 104. Actuator 106 can be actuated to move the two engagement arms toward each other and away from each other to adjust a separation distance between the two arms. Further, as will be discussed in greater detail, each engagement arm may include at least one pin-receiving hole that is configured to receive a pin inserted into a bone.

For example, first engagement arm 102 may include a first pin-receiving hole 108 and second engagement arm 104 may include a second pin-receiving hole 110. The first pin-receiving hole 108 can receive a first pin 112, while the second pin-receiving hole 110 can receive a second pin 114. The first pin 112 and second pin 114 can be inserted into different bones or bone portions being worked upon. In the case of a bone realignment procedure, for example, first pin 112 can be inserted into a metatarsal (e.g., first metatarsal 210) and second pin 114 can be inserted into a cuneiform (e.g., medial cuneiform 222). The pin-receiving holes can anchor compressor-distractor 100 to the bones being compressed and/or distracted via the pins inserted through the holes and into the underlying bones. In some configurations, the pin-receiving holes can be used to impart relative movement between one bone in which first pin 112 is inserted and another bone in which second pin 114 is inserted.

For example, first pin-receiving hole 108 and second pin-receiving hole 110 may be angled relative to each other at a non-zero degree angle such that, when compressor-distractor 100 is inserted over a substantially parallel set of pins, the angled receiving holes cause the pins to move relative to each other to align with the pin-receiving holes. The direction and extent of movement imposed by the angled pin-receiving holes of compressor-distractor 100 may vary depending on the desired surgical application in which the compressor-distractor is being used. In the case of a misaligned metatarsal, such as a bunion procedure for instance, the pin-receiving holes may be angled to impart a frontal plane rotation and/or a sagittal plane translation. As a result, when compressor-distractor 100 is installed over pins position in the metatarsal and adjacent cuneiform, the angled pin-receiving holes may cause the metatarsal to rotate in the frontal plane relative to the cuneiform and/or translate in the sagittal plane (e.g., downwardly or plantarly) to help correct a misalignment of the metatarsal.

Figure 5:
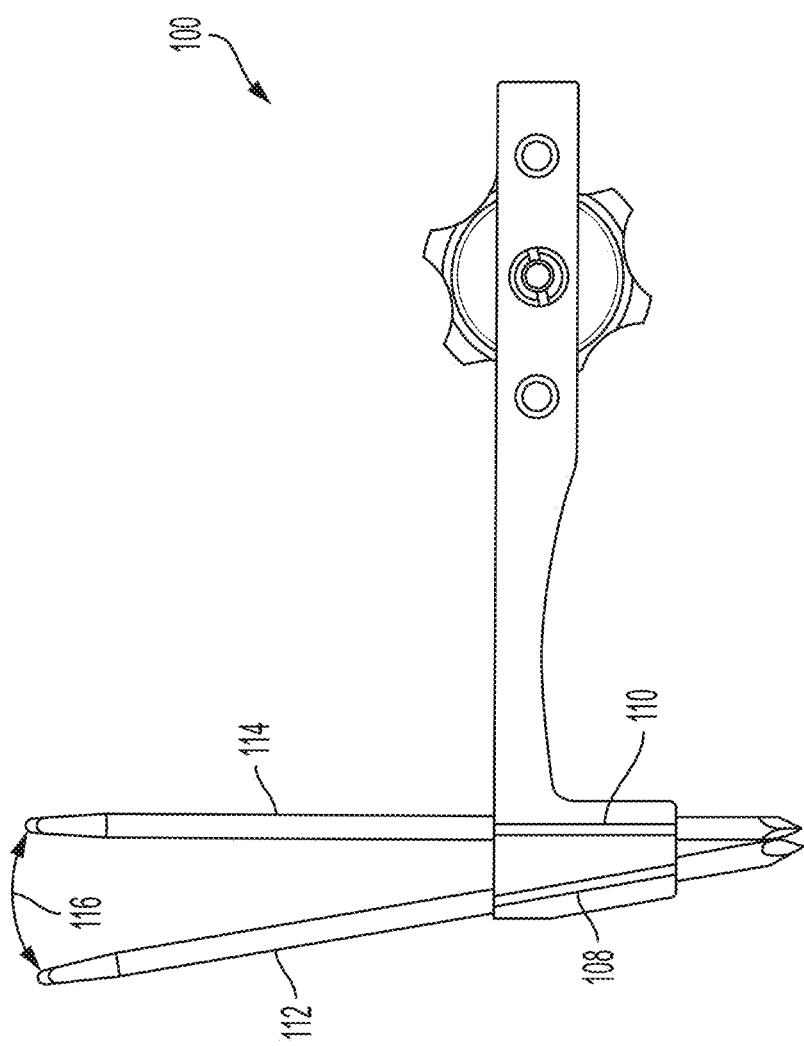
FIG. 5 is a frontal plane view of the example compressor-distractor of FIG. 4 showing an example angular offset between pin-receiving holes.

FIG. 5 is a frontal plane view of compressor-distractor 100 showing an example angular offset between first pin-receiving hole 108 and second pin-receiving hole 110. In this example, the two pin-receiving holes are angled relative to each other in the frontal plane by an angle 116. Angle 116 may be measured between two linear pins (e.g., first pin 112 and second pin 114) inserted through respective receiving holes in the perspective of the frontal plane. While the degree of angular offset between first pin-receiving hole 108 and second pin-receiving hole 110 may vary, in the case of a metatarsal realignment procedure, angle 116 may range from 2° to 20°, such as from 6° to 15°, or from 8° to 12°, or approximately 10°. The two pin-receiving holes may be offset in a direction that causes the metatarsal to rotate laterally as the compressor-distractor 100 is installed over first and second pins 112, 114. For example, when compressor-distractor 100 is positioned on the medial side of the foot, the first pin-receiving hole 108 may be angled to cause first pin 112 to rotate toward the lateral side of the foot relative to second pin 114.

In addition to or in lieu of providing a fontal plane angulation, compressor-distractor 100 may be configured to impart sagittal plane rotation, when the compressor-distractor 100 is installed over first and second pins 112, 114. For example, when installed over substantially parallel first and second pins 112, 114 positioned in the metatarsal and cuneiform, respectively, the angulation of first and second pin holes 108, 110 may cause the metatarsal to rotate or flex plantarly (e.g., such that the distal end of the metatarsal is rotated plantarly about the TMT joint).

Figure 6:
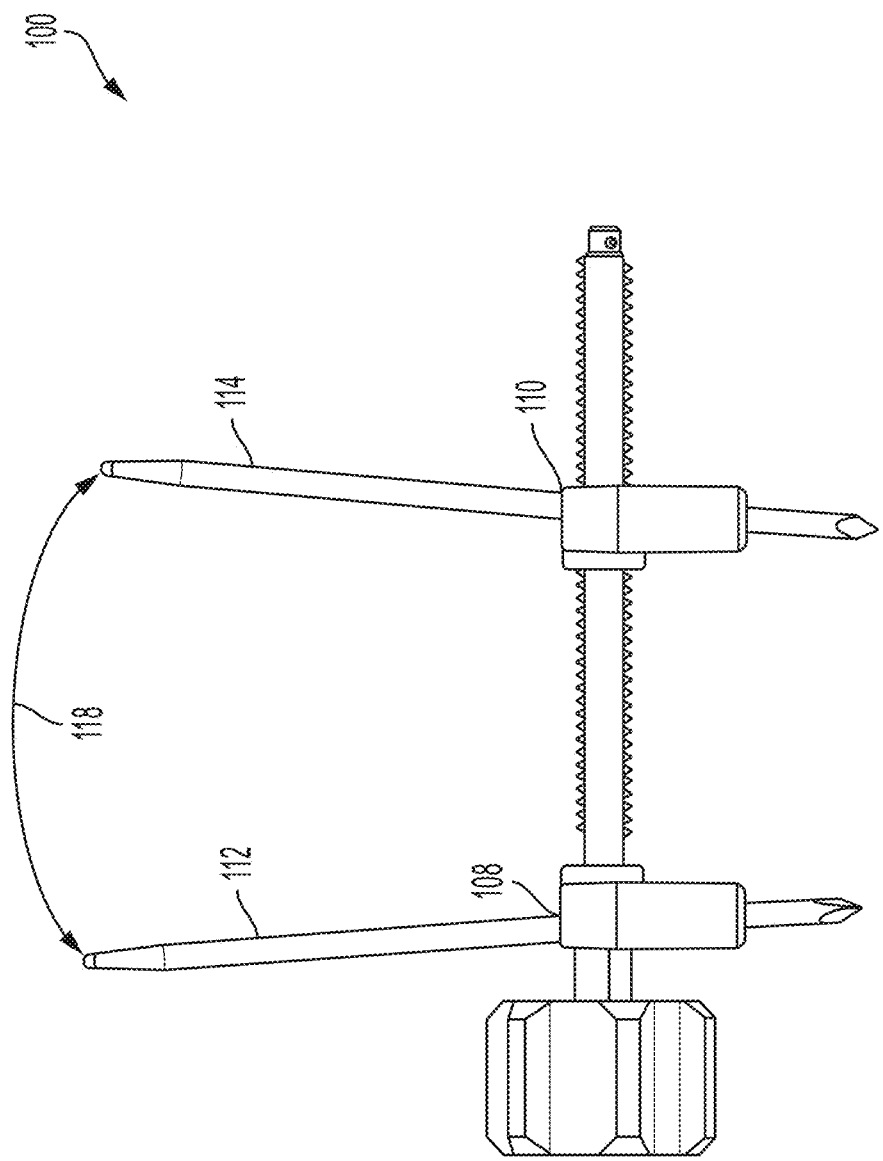
FIG. 6 is a sagittal plane view of the example compressor-distractor of FIG. 4 showing an example angular offset between pin-receiving holes.

FIG. 6 is a sagittal plane view of compressor-distractor 100 showing another example angular offset between first pin-receiving hole 108 and second pin-receiving hole 110. In this example, the two pin-receiving holes are angled relative to each other in the sagittal plane by an angle 118. Angle 118 may be measured between two linear pins (e.g., first pin 112 and second pin 114) inserted through respective receiving holes in the perspective of the sagittal plane. While the degree of angular offset between first pin-receiving hole 108 and second pin-receiving hole 110 may vary, in the case of a metatarsal realignment procedure, angle 118 may range from 5° to 12°, such as from 7° to 10°, or from 8 to 9°, or approximately 8.5°. The two pin-receiving holes may be offset in a direction that causes the metatarsal to rotate (e.g., downwardly or plantarly) in the sagittal plane as the compressor-distractor 100 is installed over first and second pins 112, 114.

In general, features described as pin-receiving holes may be void spaces extending linearly through the body of compressor-distractor 100 and configured (e.g., sized and/or shaped) to pass a pin inserted into a bone therethrough. While the pin-receiving holes may have any polygonal (e.g., square, rectangle) or arcuate (e.g., curved, elliptical) shape, the pin-receiving holes may typically have a circular cross-sectional shape. In some examples, the pin-receiving holes have a diameter ranging from 0.1 mm to 10 mm, such as from 0.5 mm to 4 mm. The pin-receiving holes may have a length (e.g., extending through the thickness of first engagement arm 102 or second engagement arm 104) ranging from 5 mm to 50 mm, such as from 10 mm to 25 mm.

Compressor-distractor 100 can have any suitable number of pin-receiving holes. In general, providing multiple pin-receiving holes on each side of the compressor-distractor 100 may be useful to provide alternative angulation or movement options for the clinician using the compressor-distractor. For example, compressor-distractor 100 may have a plurality of pin-receiving holes for use with first pin 112 and/or second pin 114. During a surgical procedure, the clinician may select a certain pin-receiving hole from the plurality of pin-receiving holes into which first pin 112 and/or second pin 114 are to be inserted. The clinician may select the pin-receiving hole combination based on the amount and direction of movement the clinician desires the first bone to move relative to the second bone upon installing the compressor-distractor over first and second pins 112, 114. After selecting the desired pin-receiving hole combination, the clinician can direct the distal end of first and second pins 112, 114 into the corresponding selected pin-receiving holes then translate compressor-distractor 100 from the distal end of the pins down towards the proximal end of the pins.

It should be appreciated that while compressor-distractor 100 may have multiple pin-receiving holes for first pin 112 and/or second pin 114, the disclosure is not limited in this respect. In other configurations, compressor-distractor 100 may only have a single pin-receiving hole into which first pin 112 and/or second pin 114 can be inserted. In still other configurations, compressor-distractor 100 may have one or more pin-receiving hole(s) that rotate and/or slide within one or more slots to provide adjustable angulation, allowing the clinician to adjust the angular alignment of first and/or second pin-receiving holes 108, 110.

In the example of FIG. 4, compressor-distractor 100 is illustrated as having two pin-receiving holes associated with first pin 112 and two pin-receiving holes associated with second pin 114. In particular, FIG. 4 illustrates first engagement arm 102 as having previously-described first pin-receiving hole 108 and second engagement arm 104 as having previously-described second pin-receiving hole 110. In addition, first engagement arm 102 is illustrated has having a third pin-receiving hole 120, while second engagement arm 104 has a fourth pin-receiving hole 122. First and second engagement arms 102, 104 may each have fewer pin-receiving holes (e.g., one) or more pin-receiving holes (e.g., three, four, or more).

In some configurations, the third pin-receiving hole 120 is angled relative to the fourth pin-receiving hole 122 at a non-zero-degree angle in a second plane different than a first plane in which first pin-receiving hole 108 is angled relative to second pin-receiving hole 110. For example, first pin-receiving hole 108 may be angled relative to second pin-receiving hole 110 in the frontal plane and/or sagittal plane. Third pin-receiving hole 120 may be parallel to second pin-receiving hole 110 in the frontal plane but angled relative to the second pin-receiving hole in the sagittal plane. Further, fourth pin-receiving hole 122 may be parallel to first pin-receiving hole 108 in the frontal plane but angled relative to the first pin-receiving hole in the sagittal plane. Third and fourth pin-receiving holes 120, 122 can be angled relative to each other and/or first and second pin-receiving holes 108, 110 at any of the angles discussed above. When configured as illustrated in FIG. 4, a clinician desiring both frontal plane and sagittal plane movement can use the first and second pin holes 108, 110. By contrast, when the clinician desires sagittal plane movement but not frontal plane movement, the clinician can use first and fourth pin-receiving hole 108, 122.

As briefly discussed above, compressor-distractor 100 can open and close to compress and distract the bones to which to the compressor-distractor is secured. To facilitate movement, compressor-distractor 100 is illustrated as having an actuator 106. Actuator 106 is configured to control movement of first engagement arm 102 relative to second engagement arm 104. Actuator 106 may be implemented using any feature that provides controllable relative movement between the two engagement arms, such as rotary movement, sliding movement, or other relative translation. In some configurations, actuator 106 is configured to move first and second engagement arms 102, 104 at least 1 mm away from each other, such as a distance ranging from 1 mm to 45 mm, a distance ranging from 1 mm to 5 mm, or a distance ranging from 1 mm to 2.5 mm during distraction. Actuator 106 may be actuated during compression until the faces of the bones to which compressor-distractor 100 is attached are suitably compressed and/or the sidewall faces of first and second engagement arms 102, 104 contact each other.

In the example of FIG. 4, actuator 106 is illustrated as including a shaft 124 connected to the first engagement arm 102 and the second engagement arm 104. Shaft 124 may be threaded and actuator 106 may further include a knob 126 coupled to the shaft. Rotation of knob 126 in one direction may cause first engagement arm 102 to move closer to second engagement arm 104, while rotation of the knob in the opposite direction can cause the first engagement arm to move away from the second engagement arm.

To secure actuator 106 to compressor-distractor 100, the actuator may be fixedly connected to one of the arms. For example, shaft 124 of actuator 106 may be fixedly attached along its length to first engagement arm 102 and rotatable relative to the arm. As a result, when knob 126 is rotated, second engagement arm 104 may move along the length of shaft 124 towards and/or away from first engagement arm 102. This provides relative movement between the two arms while first engagement arm 102 remains in a fixed position relative to actuator 106.

In FIG. 4, first engagement arm 102 is illustrated as extending from a distal end 128A to a proximal end 128B. Similarly, second engagement arm 104 is illustrated as extending from a distal end 130A to a proximal end 130B. Actuator 106 is positioned adjacent the proximal ends 128B, 130B of the first and second engagement arms 102, 104, respectively, such as the proximal half of the arms in the illustrated configuration. Offsetting actuator 106 from the pin-receiving holes may be useful, for example, to provide clearance for the clinician to manipulate the actuator when compressor-distractor 100 is inserted on pins installed in bones. In the case of a foot surgery, first and second engagement arms 102, 104 may have a length affective to position actuator 106 to be offset medially from the foot being operated on while first pin-receiving hole 108 is engaged with a first pin 112 inserted into a metatarsal and second pin-receiving hole 110 is engaged with a second pin 114 engaged with a cuneiform.

To help stabilize first engagement arm 102 relative to second engagement arm 104 during movement along shaft 124, compressor-distractor 100 may also include one or more unthreaded shafts extending parallel to the threaded shaft. In FIG. 4, for example, actuator 106 has a first unthreaded shaft 132A and a second unthreaded shaft 132B (collectively referred to as "unthreaded shaft 132"). Unthreaded shaft 132 extends parallel to threaded shaft 124 and helps stabilize second engagement arm 104 as it moves along the threaded shaft towards and away from first engagement arm 102. Threaded shaft 124 is illustrated as extending through a threaded aperture in the sidewall of second engagement arm 102, while unthreaded shaft 132 is illustrated as extending through an unthreaded aperture in the sidewall of the engagement arm.

First engagement arm 102 and second engagement arm 104 can have a variety of different sizes and shapes. In general, each engagement arm may define a length offsetting the pin-receiving holes from actuator 106. In some examples, distal end 128A of first engagement arm 102 defines a first pin block 134 and/or distal end 130A of second engagement arm 104 defines a second pin block 136. The pin blocks may be regions of the respective engagement arms defining pin-receiving holes and through which the pin-receiving holes extend. First and second pin blocks 134, 136 may have a thickness greater than a thickness of the remainder of the engagement arms. For example, as shown, pin blocks 134, 136 may extend downwardly (e.g., plantarly) from a remainder of the engagement arms and/or actuator 106.

In FIG. 4, first engagement arm 102 is illustrated as having a same length as second engagement arm 104. As a result, distal end 128A of the first engagement arm is parallel with the distal end 130A of the second engagement arm. In other configurations, one engagement arm may be longer than the other engagement arm to provide an offset. For example, first engagement arm 102 may be longer than second engagement arm 104, e.g., causing the first engagement arm to extend farther laterally when applied to a foot being operated upon than second engagement arm 104. This configuration may be useful during bunion correction procedures to impart transverse plane movement (e.g., rotation) of the metatarsal relative to the cuneiform to close the IM angle.

Compressor-distractor 100 may be fabricated from any suitable material or combination of materials, such as metal (e.g., stainless steel) and/or polymeric materials. In some configurations, compressor-distractor 100 is fabricated from a radiolucent material such that it is relatively penetrable by X-rays and other forms of radiation, such as thermoplastics and carbon-fiber materials. Such materials are useful for not obstructing visualization of bones using an imaging device when the bone positioning guide is positioned on bones.

Figure 7:
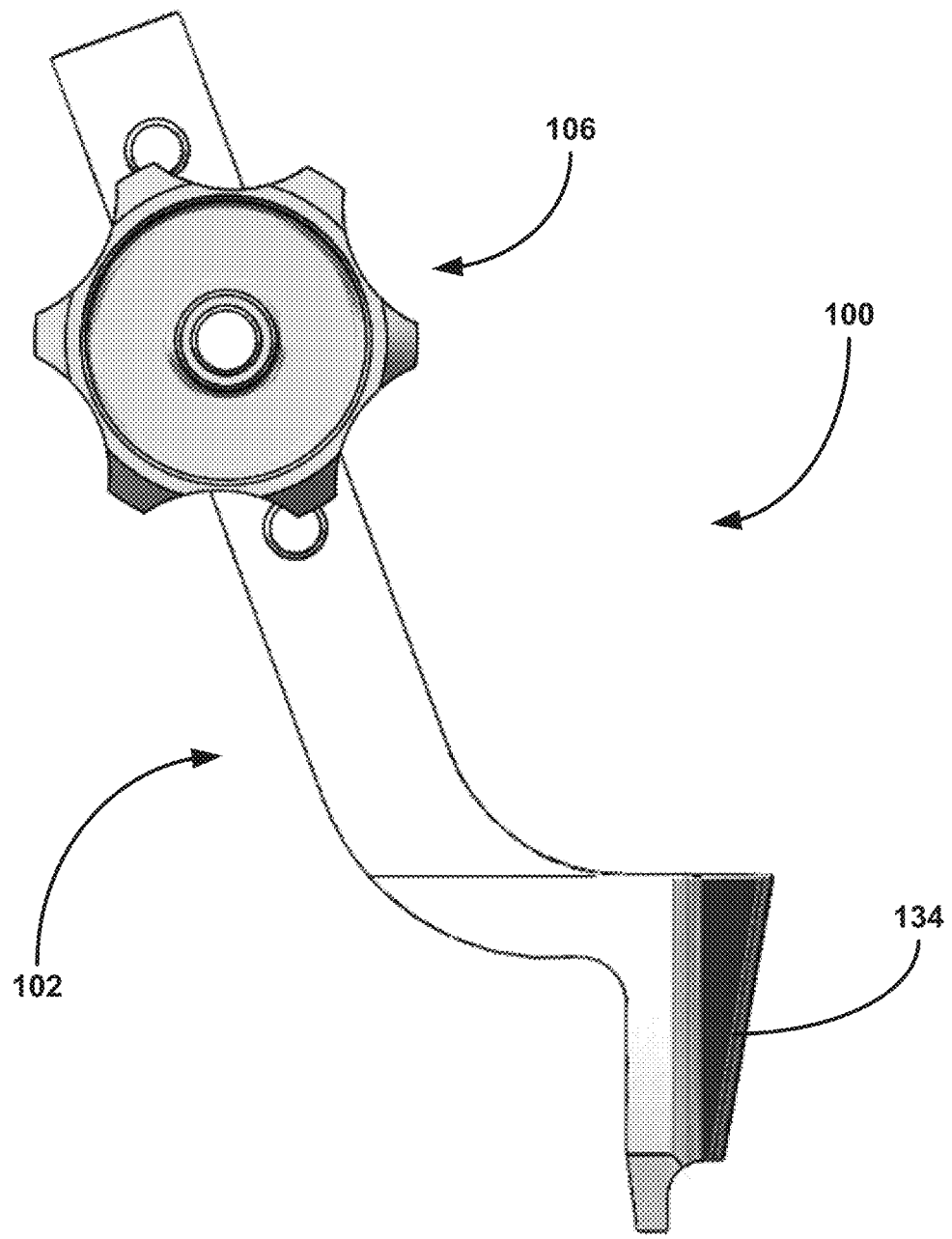
FIG. 7 is a side view of an example configuration of the compressor-distractor of FIG. 4.

Compressor-distractor 100 can have a variety of different configurations, and a compressor-distractor according to the disclosure is not limited to the example configuration illustrated with respect to FIGS. 3-6. For example, FIG. 7 illustrates a side view of an alternative configuration of compressor-distractor 100 in which first engagement arm 102 and second engagement arm 104 are curved upwardly away from first and second pin blocks 134, 136. The curvature of the arms can position actuator 106 out of the surgical site, removing a visual obstruction to help the clinician perform the surgical technique.

As mentioned above, a compressor-distractor according to some implementations of the disclosure may not be configured with angled pin-receiving holes and/or may have parallel pin-receiving holes that are utilized in lieu of angled pin-receiving holes also presented on the compressor-distractor. FIG. 7 is a perspective illustration of another example configuration of compressor-distractor 100 deployed in an example surgical technique attached to foot 200. Like reference numerals in FIG. 7 reference to like elements discussed above with respect to FIGS. 1-6.

Some example systems and techniques according to the present disclosure may utilize an instrument defining a sliding surface, which can be positioned between a bone being moved (e.g., first metatarsal) and an adjacent stationary bone (e.g., second metatarsal). In general, any suitable mechanical instrument that maintains a spacing between adjacent bones and provides a surface along which a bone can translate be used as the instrument defining the sliding surface according to the disclosure.

Figure 8:
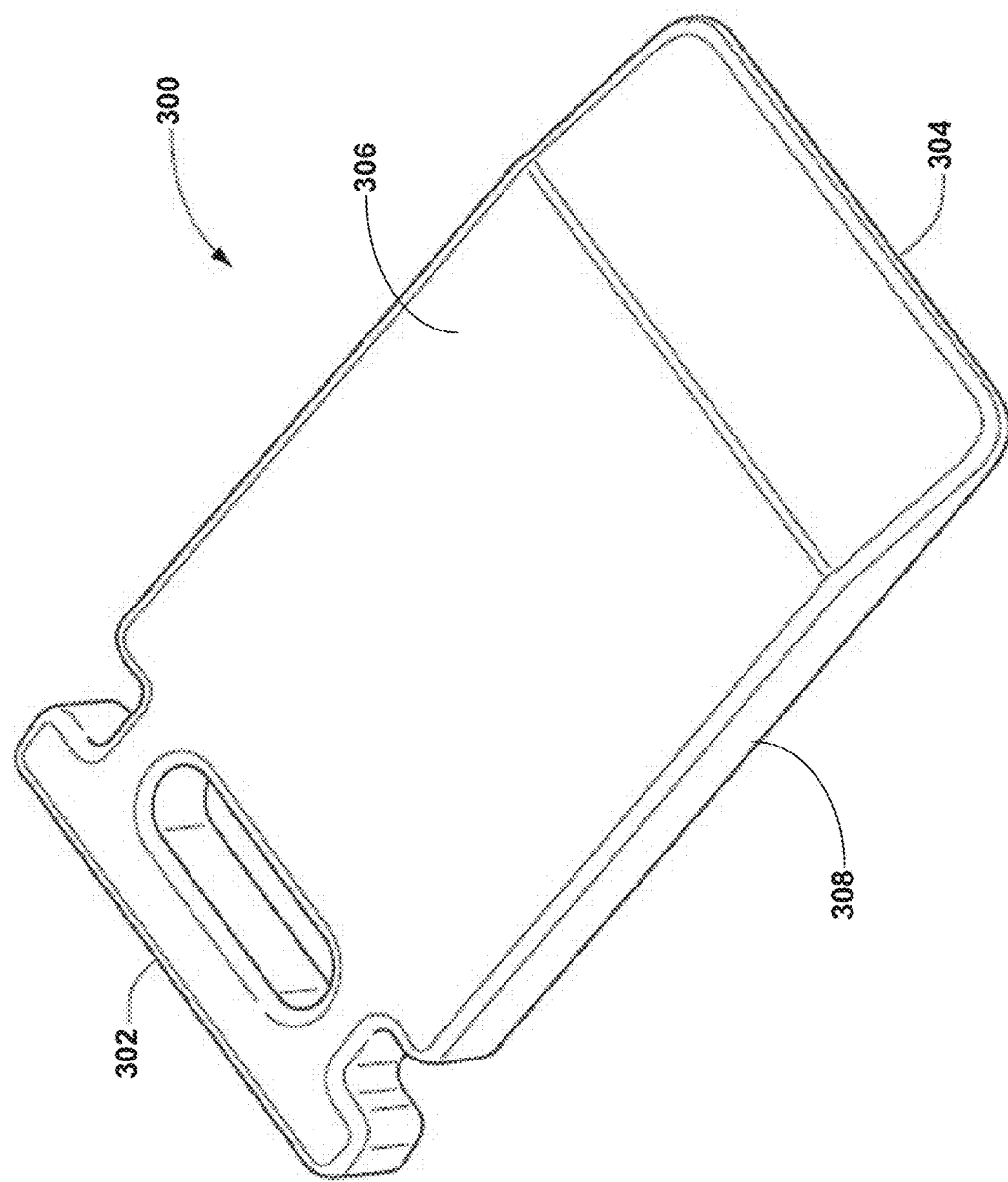
FIG. 8 is a perspective view of one example instrument defining a sliding surface.

FIG. 8 is a perspective view of one example instrument that can be used as an instrument defining a sliding surface. In this instrument, instrument 300 has a generally rectangular shape and tapers in thickness along at least a portion of the length from the trailing end 302 to the leading end 304. Instrument 300 defines a first major face 306 and a second major face 308 opposite the first major face. One or both of first major face 306 and second major face 308 may provide a sliding surface along a bone being moved can slide during performance of a bone realignment procedure.

Figure 9:
FIG. 9 illustrates an example system of different sized instruments defining sliding surfaces.

Instrument 300 may be sized sufficiently small (e.g., in thickness) so that it can be positioned between a bone being moved (e.g., first metatarsal) and an adjacent stationary bone (e.g., second metatarsal). In some implementations, the clinician is provided a system containing multiple different size and/or shape instruments defining sliding surfaces and allowed to choose the specific size and/or shape instrument desired for the specific procedure being performed. FIG. 9 illustrates an example kit or system of different sized instruments defining a sliding surface, labeled with exemplary "width×thickness" sizes, that may be provided to a clinician in such an embodiment. In some examples, the instrument defining the sliding surface has a width ranging from 5 millimeters to 15 millimeters (e.g., about 6 millimeters to about 10 millimeters) and a thickness ranging 1 millimeter to 12 millimeters (e.g., about 2 millimeters to about 3 millimeters), although instruments having different dimensions can be used.

Figure 10A:
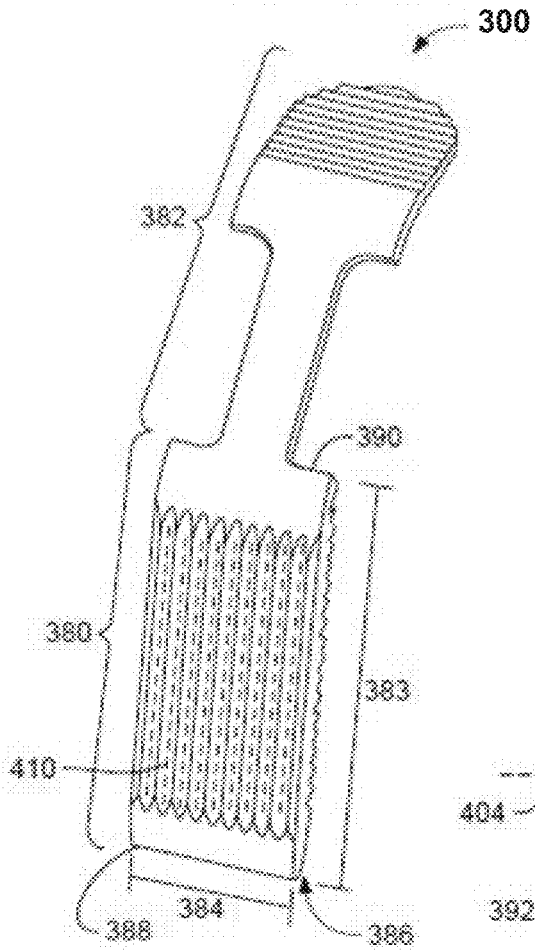
FIGS. 10A and 10B are different perspective views of another example instrument defining a sliding surface that can be used during a bone correction procedure.
Figure 10B:
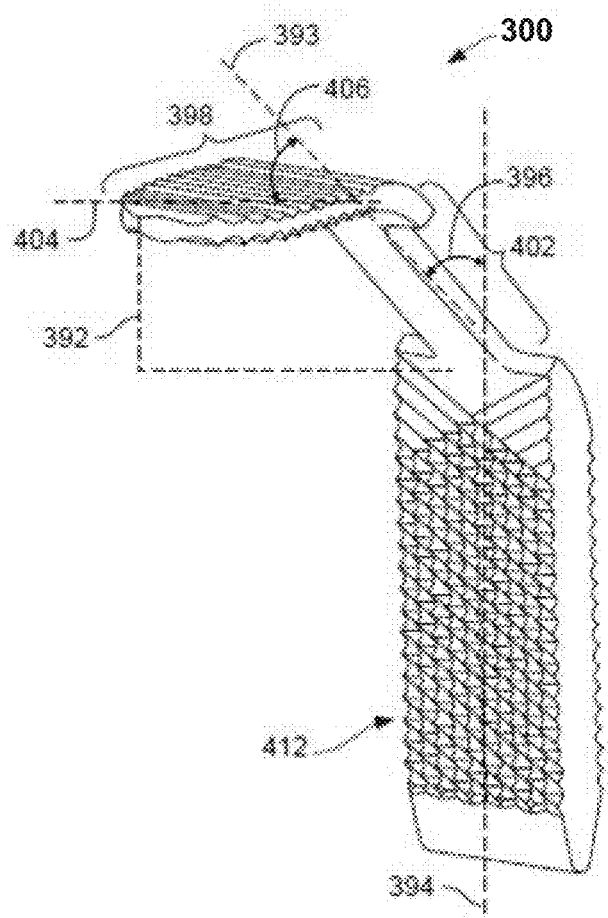

The instrument 300 defining the sliding surface can have a variety of different configurations. FIGS. 10A and 10B illustrate another example configuration of instrument 300 that can be used according to the disclosure. FIG. 10A is a perspective view of one side of instrument 300, while FIG. 10B is a perspective view of the instrument from the opposite side. In the illustrated configuration, instrument 300 includes a body 380 and a handle 382 operatively connected to the body. Typically, body 380 and handle 382 will be formed as a unitary structure, e.g., by milling, casting, or molding the components to be permanently and structurally integrated together. However, body 380 and handle 382 may be fabricated as separate components that are subsequently joined together.

Body 380 can be configured (e.g., sized and shaped) to be inserted into an intermetatarsal space between adjacent metatarsals. For example, body 380 may be configured to be inserted between a first metatarsal and a second metatarsal. Body 380 is illustrated as having a rectangular shape with a length 383 greater than its width 384 and thickness 386. Moreover, in this configuration, body 380 has a constant width 384 across its length but has a thickness 386 that that tapers along at least a portion of the length from the leading end 388 to the trailing end 390. For example, body 380 may have a tapered leading end 388 to facilitate insertion of instrument 300 in a space between adjacent metatarsals. In other configurations, body 380 may have a constant thickness across is length or may define a different generally polygonal shape (e.g., square, hexagonal) and/or generally arcuate shape (e.g., circular, elliptical).

Instrument 300 in FIGS. 10A and 10B includes handle 382. Handle 382 can project angularly away from body 380 to define a tissue retraction space 392. Tissue retraction space 392 may be a region bounded on one side by body 380 and one or more other sides by handle 382. In use, instrument 300 may be inserted into an intermetatarsal space with handle 382 extending out of the surgical incision and over an epidermal layer with tissue captured in tissue retraction space 392. For example, instrument 300 may be inserted into an intermetatarsal space with handle 382 projecting toward the lateral side of the foot being operated upon. Tissue retraction space 392 may help retract tissue and push the tissue laterally away from a first metatarsal and/or medial cuneiform being operated upon.

In the illustrated example, handle 382 is illustrated as projecting laterally at a non-zero-degree angle away from body 380. The specific angular orientation of the handle 382 relative to the body 380 may vary. However, in some examples, handle 382 is oriented relative to the body 380 so a handle axis 393 intersects an axis 394 extending along the length of the body at an acute angle 396 ranging from 20 degrees to 75 degrees, such as 35 degrees to 55 degrees. Moreover, handle 382 may be composed of a single linear portion that intersects body 380 at a specific angular orientation or may be composed of multiple linear portions oriented at different angles relative to each other.

In the illustrated example, handle 382 includes a grip portion 398 and a handle body 402. The grip portion 398 can provide a surface that a clinician physically grips to insert instrument 300 into an intermetatarsal space. For example, grip portion 398 may contain knurling or other anti-friction surfacing texturing to allow the clinician to help grip the fulcrum. Handle body 402 may be positioned between the body 380 of instrument 300 and grip portion 398. Handle body 402 may or may not have a reduced cross-sectional width compared to body 380 and/or grip portion 398, as illustrated.

When configured with grip portion 398, the grip portion can be co-linear with handle body 402 or may be offset relative to the handle body. When grip portion 398 is offset from handle body 402, a grip axis 404 extending along the length of the grip portion may intersect the handle axis 393 at an acute ranging from 20 degrees to 75 degrees, such as 35 degrees to 55 degrees, although other angular arrangements can also be used. In the illustrated configuration, grip axis 404 is perpendicular to the axis 394 defined by body 380. Accordingly, when inserted into an intermetatarsal space, retracted tissue may be bounded by a laterally-facing side of body 380, by the lower surface of grip portion 398, and in the dorsal-lateral direction by handle portion 392.

In some examples, the bone-contacting faces of body 380 are configured to inhibit and/or facilitate relative motion between a bone and the respective bone-contacting face. With reference to FIG. 10A, body 380 of instrument 300 has a first face 410, which may be positioned in contact with a first metatarsal. First face 410 may provide a sliding surface against which the metatarsal can contact and slide against during translation. Accordingly, first face 410 may have surface features which allow the contacting metatarsal (e.g., first metatarsal) to translate and slide against during movement from a distal to proximal direction. The surface features may be implemented as directionally-oriented ribs and/or grooves.

Figure 11:
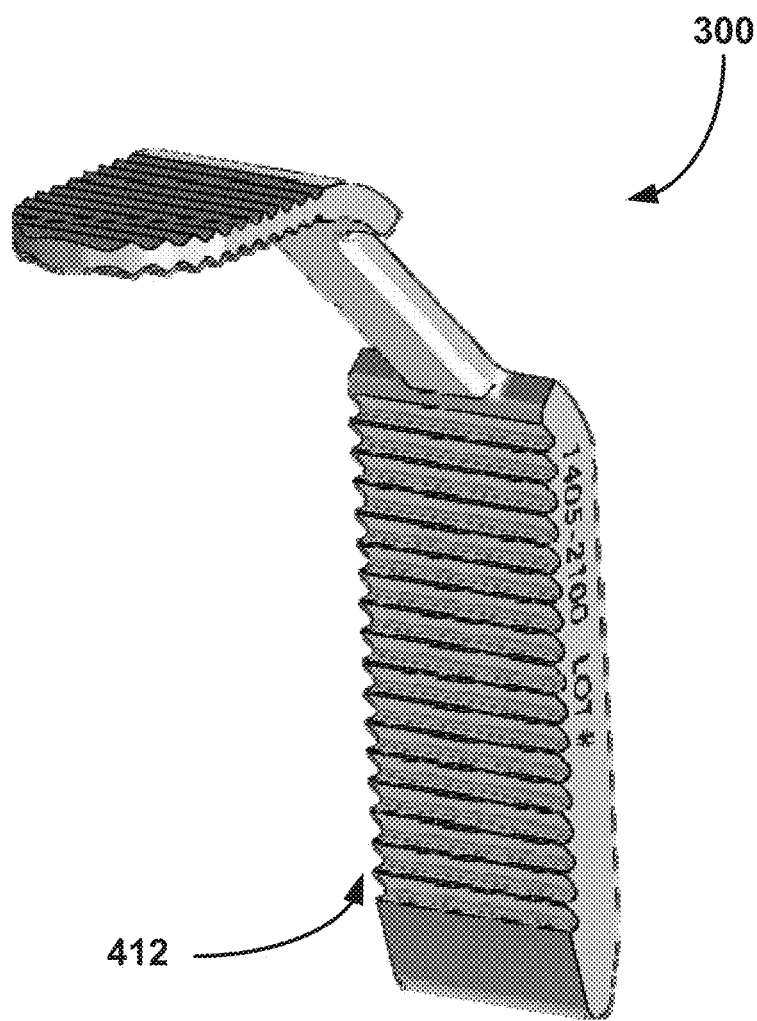
FIG. 11 illustrates an alternative arrangement of surface features that may be used on the example instrument defining a sliding surface of FIGS. 10A and 10B.

For example, FIG. 11 is perspective view of the second face 412 of instrument 300 showing an example arrangement of surface features that may be used to facilitate distal to proximal axial translation of the metatarsal, e.g., while inhibiting plantar or dorsal movement. By orienting the grooves widthwise, the edges of the grooves may have a tendency to engage or bite into the metatarsal if the metatarsal is moved plantarly or dorsally, thereby inhibiting such movement, while allowing the metatarsal to move distally and/or proximally. It should be appreciated, however, that a slide surface of instrument 300 may have a different configuration of surface features (e.g., even ones that generally inhibit movement) or may not have any surface features.

With further reference to FIG. 10B, body 380 may have different surface features on the opposite face from first face 410. For example, body 380 of instrument 300 has a second face 412 that is opposite first face 410. Second face 412 may have surface features that inhibit movement between instrument 300 and the contacting metatarsal (e.g., second metatarsal) in the dorsal-to-plantar direction. The surface features may be implemented as directionally-oriented ribs and/or grooves. For example, in FIG. 10B, second face 412 is illustrated as having knurling, or a series of intersecting and overlapping ridges.

In the configuration of FIGS. 10A and 10B, handle 382 includes grip portion 398 that can provide a surface a clinician physically grips to insert instrument 300. In other configurations, handle 382 may be implemented using a second instrument body that is a different size and/or shape than body 380. This arrangement can provide a clinician with a single instrument having two functional ends, either one of which can be selected and used by the clinician, e.g., depending on the characteristics of the patient undergoing a surgical procedure.

Figure 12A:
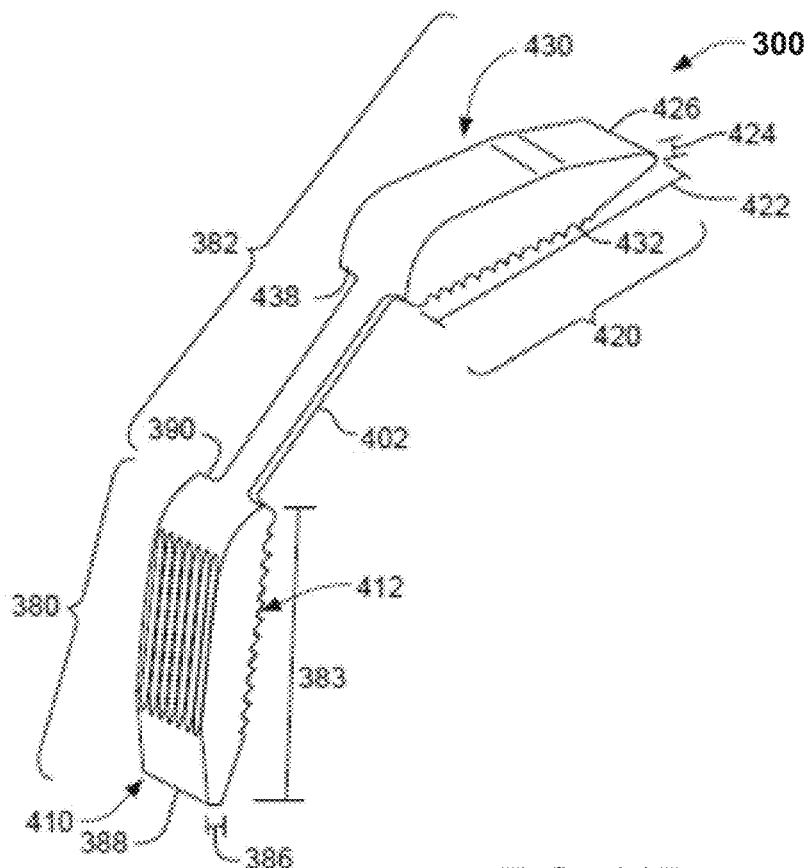
FIGS. 12A and 12B are perspective and side views, respectively, of an example instrument defining a sliding surface having two sliding surface bodies.
Figure 12B:
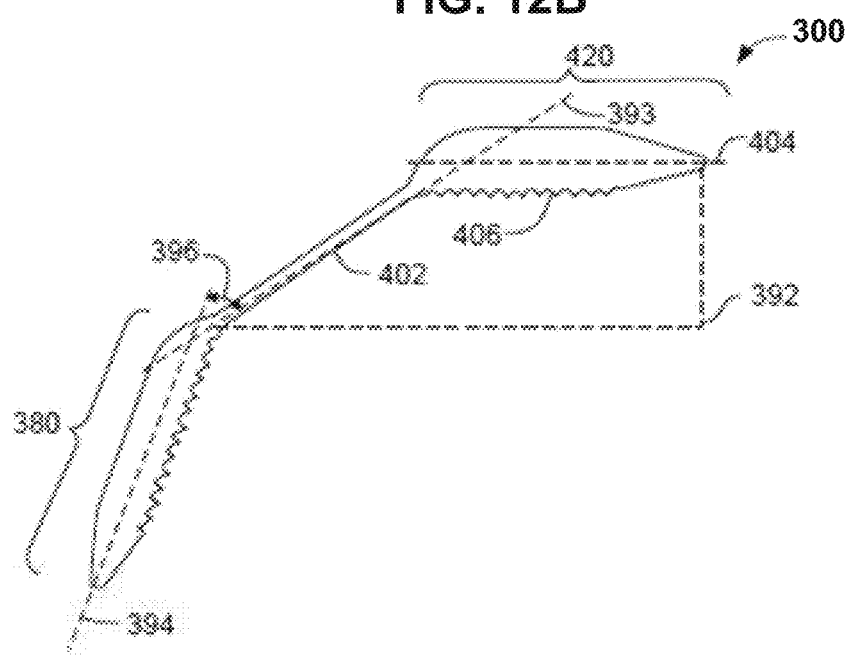

FIGS. 12A and 12B are perspective and side views, respectively, of such an example instrument 300 having two bodies defining sliding surfaces. As shown in this example, instrument 300 includes the body 380 and the handle 382 projecting at a non-zero-degree angle away from the body. The body 380 provides a first body defining a sliding surface and configured (e.g., sized and/or shaped) to be inserted into an intermetatarsal space. In addition, handle 382 in this example is defined at least in part by a second body 420. The second body 420 defining a sliding surface may also be configured (e.g., sized and/or shaped) to be inserted into an intermetatarsal space. The first body 380 can differ from the second body 420 by having a different size and/or shape.

In FIGS. 12A and 12B, the first body 380 and the second body 420 are shown as having the same shape but different sizes. In particular, first body 380 has a length 383, a thickness 386, and a width orthogonal to the length and thickness. Further, the second body 420 has a length 422, a thickness 424, and a width orthogonal to the length and thickness. The thickness 422 of the second body 420 is illustrated as being greater than the thickness 386 of the first body 380. The length and width of the first and second bodies 380, 420 are illustrated as being the same but may be different in other examples (e.g., different width with same length, different length but same width, or different length and width).

In general, configuring the first body 380 and second body 420 with different thicknesses can be useful to facilitate use in different sized intermetatarsal spaces. For example, the clinician may select one sized body over the other sized body based on the anatomy (e.g., intermetatarsal space sizing) of the patient undergoing a surgical procedure. If the clinician determines upon beginning to insert the selected instrument body that the selected body is inappropriately sized, the clinician may retract the instrument, flip the instrument, and insert the body on the opposite side of the instrument.

While the first body 380 and second body 420 can be configured with a variety of different sizes, in some examples, each body has a thickness ranging from 0.5 millimeters to 12 millimeters, such as from 1 millimeter to 10 millimeters, or from 1 millimeter to 5 millimeters. The thickness 424 of the second body 420 may be at least 0.2 millimeters thicker than the thickness 386 of the first body, such as at least 0.5 millimeters thicker, at least 1 millimeter thicker, or at least 2 millimeters thicker. In some examples, first body 380 and second body 420 each have a width within a range from 5 millimeters to 15 millimeters (e.g., about 6 millimeters to about 10 millimeters) and a length ranging from 10 millimeters to 30 millimeters, although other dimensions can be used.

In the illustrated example of FIGS. 12A and 12B, the first body 380 has a leading end 388 and a trailing end 390 and the second body 420 has a leading end 426 and a trailing end 428. In some examples as shown, the leading end 388 of the first body 380 and/or the leading end 426 of the second body 420 has a thickness that tapers adjacent the leading end. This configuration can be useful to facilitate insertion of an instrument body into an intermetatarsal space. When configured with a tapered leading end, the exemplary thickness ranges discussed above may be measured as the maximum thickness of the body at any location along the length of the body.

In the illustrated example, first body 380 and second body 420 are oriented at a non-zero degree relative to each other and separated by a handle body 402, e.g., of lesser cross-sectional width. For example, as discussed with respect to FIGS. 10A and 10B, handle 382 may be oriented relative to first body 380 such that handle axis 393 intersects an axis 394 extending along the length of the body at an acute angle 396. When handle 382 includes the handle body 402 and the second body 420, the second body can be co-linear with handle body 402 or may be offset relative to the handle body. For example, an axis 404 extending along the length of the second body may intersect the handle axis 393 at an acute angle 406 ranging from 20 degrees to 75 degrees, such as 35 degrees to 55 degrees, as discussed above.

In yet other configurations where instrument 300 is configured with multiple ends of different dimensions, the ends may or may not be separated by a separate handle body 402. For example, first body 380 and second body 420 may be formed as a unitary structure (e.g., as opposed ends of a linear or curved unitary body).

Figure 13A:
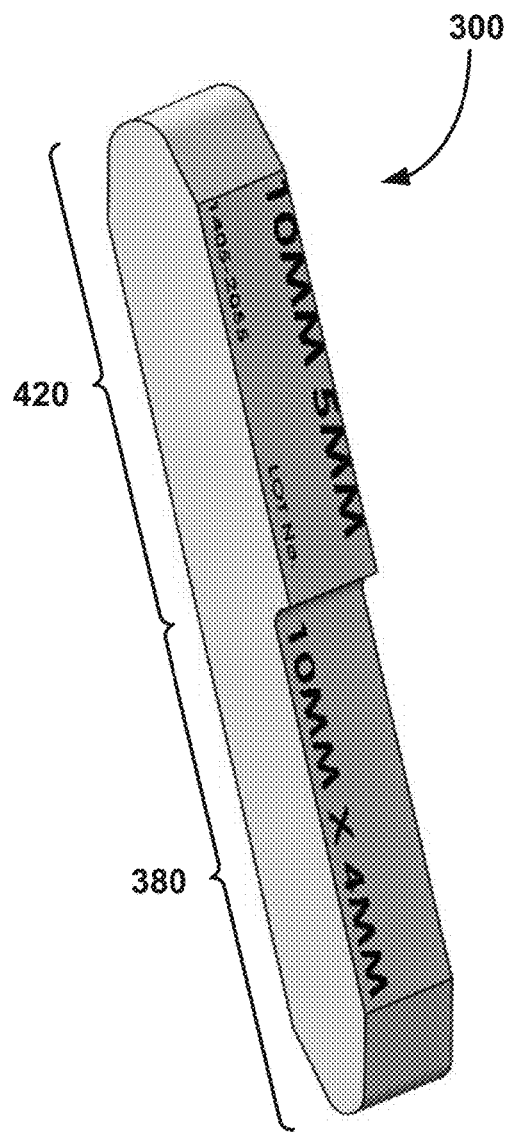
FIGS. 13A and 13B are perspective and side views, respectively, of an example multidimensional instrument defining a sliding surface having ends of different dimensions and a unitary body.
Figure 13B:
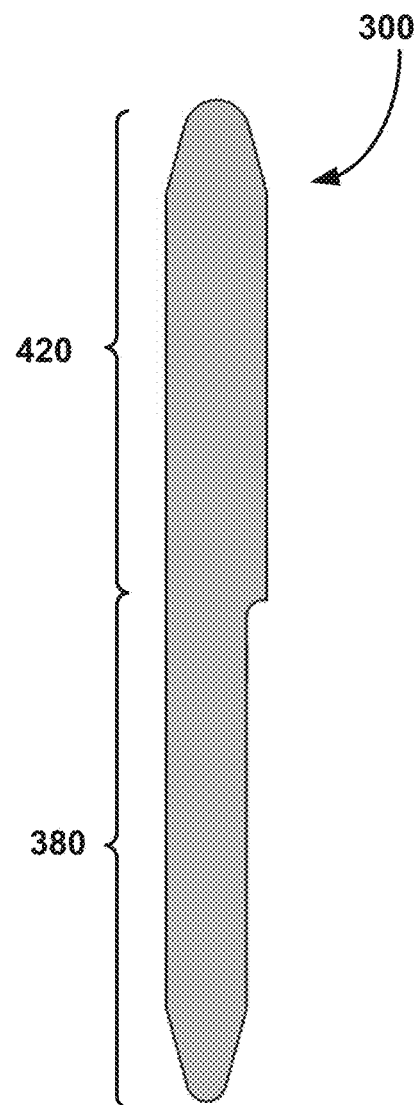

FIGS. 13A and 13B are perspective and side views, respectively, of an example multidimensional instrument defining a sliding surface having ends of different dimensions. As shown, instrument 300 is composed of first body 380 and second body 420 as discussed above with respect to FIGS. 12A and 12B. In the configuration illustrated in FIGS. 13A and 13B, however, the first body 380 and the second body 420 are integrated together to form a unitary instrument having two opposed ends of different dimensions, either of which can be inserted into an intermetatarsal space to provide a sliding surface. As illustrated, the unitary instrument body has a generally rectangular shape such that opposed ends of the instrument are separated by a linear length of the body. However, the body may be curved or non-linear in alternative configurations. As discussed above, the first body 380 and the second body 420 forming the respective portions of the unitary body can have a variety of different dimensions, and may or may not have surface features, to provide a clinician with a variety of sliding surface options in a single instrument.

A system that includes a compressor-distractor and instrument defining a sliding surface according to the disclosure may be used as part of a surgical procedure in which at least two pins are inserted into different bones or different portions of the same bone. The at least two pins may be inserted in generally parallel alignment and/or the pins may be realigned during the surgical procedure so as to be substantially parallel (e.g., prior to installation of compressor-distractor 100). The two pins may be substantially parallel in that the pins are positioned side-by-side and have substantially the same distance continuously between the two pins in each of the three planes (e.g., the distance varies by less than 10%, such as less than 5% across the lengths of the pins in any given plane, with different continuous distances in different planes). Compressor-distractor 100 can be inserted over the parallel pins by threading the parallel pins into the pin-receiving holes of the device. If the pin-receiving holes of compressor-distractor 100 are parallel, the compressor-distractor can be inserted over the pins without changing the position of the pins. By contract, if the pin-receiving holes of compressor-distractor 100 are angled, inserting the compressor-distractor over the pins can cause the pins to move from a substantially parallel alignment to an angled alignment dictated by the angulation of the pin-receiving holes.

In either case, compressor-distractor 100 may then be used to distract the bone portions into which the pins are inserted (e.g., by actuating actuator 106 to draw the bone portions away from each other) and/or compress the bone portions into which the pins are inserted (e.g., by actuating actuator 106 to move the bone portions towards each other). Instrument 300 can be positioned between a bone portion being compressed (e.g., a distracted metatarsal) and an adjacent stationary bone (e.g., a lateral-most metatarsal to the distracted metatarsal). Compressor-distractor 100 can compress two separated bone portions toward and/or against each other, e.g., causing the distracted bone portion to translate against the surface of instrument 300.

In some examples, compressor-distractor 100 and instrument 300 is used as part of a metatarsal realignment procedure in which a metatarsal is realigned relative to an adjacent cuneiform and/or metatarsal in one or more planes, such as two or three planes. Additional details on example bone realignment techniques and devices with which compressor-distractor 100 and instrument 300 may be used are described in U.S. Pat. No. 9,622,805, titled "BONE POSITIONING AND PREPARING GUIDE SYSTEMS AND METHODS," filed on Dec. 28, 2015 and issued Apr. 18, 2017, and U.S. Pat. No. 9,936,994, titled "BONE POSITIONING GUIDE," filed on Jul. 14, 2016 and issued on Apr. 10, 2018, and US Patent Publication No. 2017/0042599 titled "TARSAL-METATARSAL JOINT PROCEDURE UTILIZING FULCRUM," filed on Aug. 14, 2016. The entire contents of each of these documents are hereby incorporated by reference.

The pins over which compressor-distractor 100 is installed may be used to pin and/or guide another medical instrument used during the surgical technique. For example first and second pins 112, 114 may be used to pin a first medical instrument to the bones or bone portions being operated upon. The medical instrument can be removed over the parallel pins, leaving the pins inserted into the bone or bone portions, and compressor-distractor 100 subsequently placed over the pins.

For example, in the case of a metatarsal realignment procedure, first and second pins 112, 114 may be used to pin a bone preparation guide to a foot being operated upon. The bone preparation guide can be used to prepare an end face of a metatarsal and an adjacent end face of a corresponding cuneiform. The bone preparation guide can be taken off the first and second pins and compressor-distractor 100 installed on the pins. Compressor-distractor 100 can be manipulated to open the joint space between the metatarsal and cuneiform, e.g., to facilitate joint cleanup, and/or manipulated to compress the two bones together for fixation.

Figure 14:
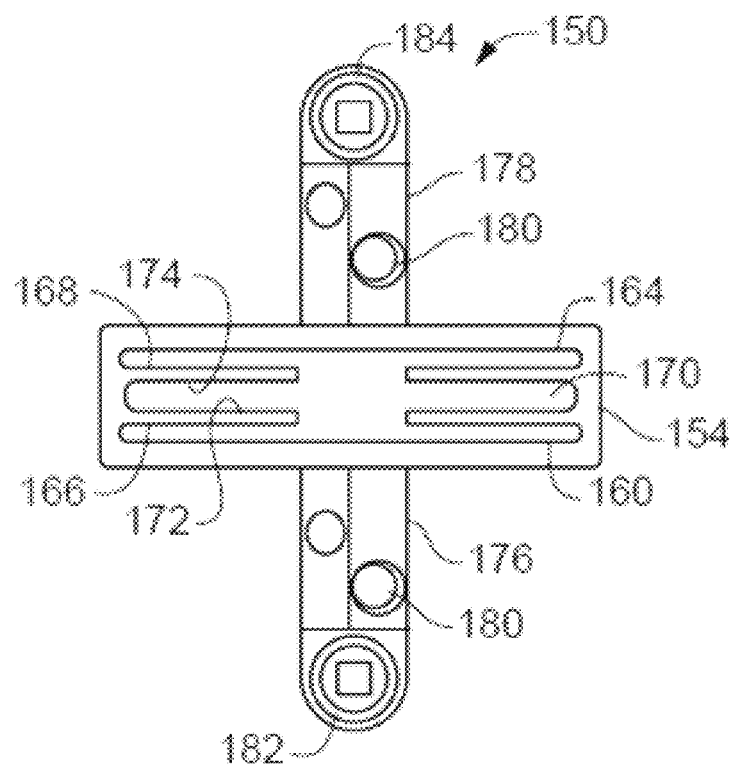
FIG. 14 is a top plan view of an example bone preparation guide that can be used with a compressor-distractor and instrument defining a sliding surface.

FIG. 14 illustrates an example bone preparation guide 150 that may be used as part of a surgical procedure involving compressor-distractor 100 and instrument 300. In some examples, bone preparation guide 150 includes a body 154 defining a first guide surface 160 to define a first preparing plane and a second guide surface 164 to define a second preparing plane. A tissue removing instrument (e.g., a saw, rotary bur, osteotome, etc., not shown) can be aligned with the surfaces to remove tissue (e.g., remove cartilage or bone and/or make cuts to bone). The first and second guide surfaces 160, 164 can be spaced from each other by a distance, (e.g., between about 2 millimeters and about 10 millimeters, such as between about 4 and about 7 millimeters). In the embodiment shown, the first and second guide surfaces are parallel, such that cuts to adjacent bones using the guide surfaces will be generally parallel.

In some configurations, as shown in FIG. 14, a first facing surface 166 is positioned adjacent the first guide surface 160 and/or a second facing surface 168 is positioned adjacent the second guide surface 164. In such configurations, the distance between the first guide surface and the first facing surface defines a first guide slot, and the distance between the second guide surface and the second facing surface defines a second guide slot. Each slot can be sized to receive a tissue removing instrument to prepare the bone ends. The first and second slots may be parallel or skewed. In the illustrated example, the facing surfaces each contain a gap, such that the surface is not a single, continuous surface. In other embodiments, the facing surfaces can be a single, continuous surface lacking any such gap.

An opening 170 can be defined by the body 154 between the first and second guide surfaces. The opening can be an area between the guide surfaces useful for allowing a practitioner to have a visual path to bones during bone preparation and/or to receive instruments. In the configuration shown, the opening extends across the body and a distance from a surface 172 opposite of the first facing surface 166 to a surface 174 opposite of the second facing surface 168.

The illustrated bone preparation guide also includes a first end 176 extending from the body 154 in a first direction and a second end 178 extending from the body in a second direction. The second direction can be different than the first direction (e.g., an opposite direction). As shown, each of the first end and the second end can include at least one fixation aperture 180 configured to receive a fixation pin to secure the bone preparation guide to an underlying bone. For example, first end 176 of bone preparation guide 150 may define a first fixation aperture through which first pin 112 (FIG. 4) is inserted and the second and 178 of bone preparation guide 150 may define a second fixation aperture through which second pin 114 (FIG. 4) is inserted. These two fixation apertures may be parallel aligned, such that first and second pins 112, 114 extend through the holes parallel to each other. The first end 176 and/or the second end 178 of bone preparation guide 150 may also defined one or more additional fixation apertures that are angled (at a non-zero-degree angle) or otherwise skewed relative to the two parallel fixation apertures.

In use, a clinician may insert the two parallel pins through fixation apertures 180 and may optionally insert one or more angled pins through the one or more angled fixation apertures. This combination of parallel and angled pins may prevent bone preparation guide 150 from being removed from the underlying bones being worked upon. When the clinician has completed using the bone preparation guide, the angled pin or pins may be removed leaving the two parallel pins inserted into the underlying bones. Bone preparation guide 150 can be slid or otherwise moved up and off the parallel pins and compressor-distractor 100 thereafter inserted down over the pins.

In some examples as shown in FIG. 14, bone preparation guide 150 can also include a first adjustable stabilization member 182 engaged with the first end 176 and/or a second adjustable stabilization member 184 engaged with the second end 178. Each of the members can be threaded and engage a threaded aperture defined by the ends. The elevation of each end can be adjusted with respect to a bone by adjusting the stabilization member. In some embodiments, as shown, the stabilization members are cannulated such that they can receive a fixation pin.

Figure 15:
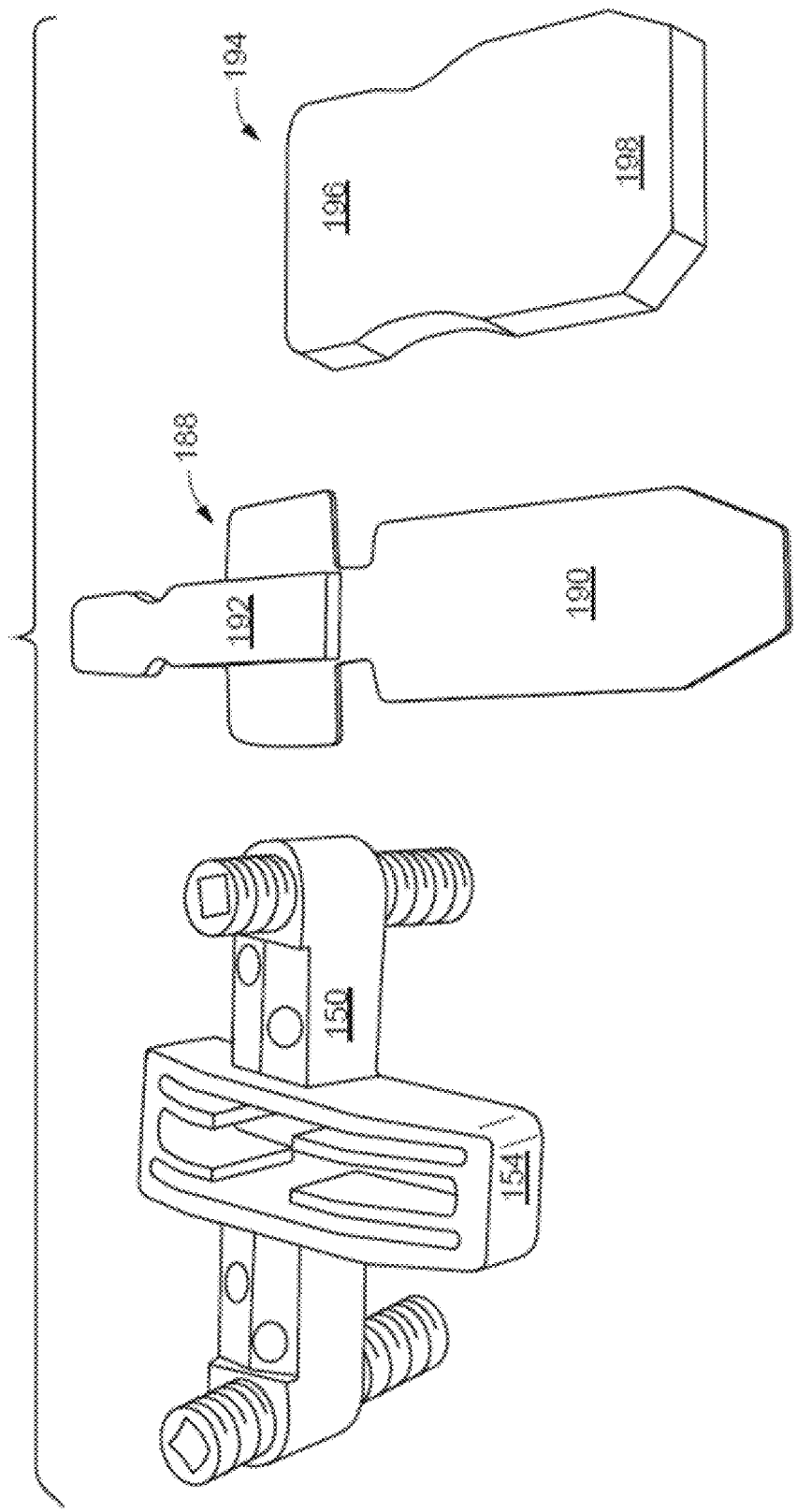
FIG. 15 is a perspective view of an example bone preparing guide, spacer, and tissue removing instrument check member that can be used with a compressor-distractor and instrument defining a sliding surface.

With reference to FIG. 15, bone preparation guide 150 may include or be used with a spacer 188 that extends downward from the body 154. Spacer 188 may be configured to be placed into a joint (e.g., within the TMT joint). In some embodiments, the spacer 188 is selectively engageable with the body of the bone preparation guide and removable therefrom. The spacer can have a first portion 190 configured to extend into a joint space and a second portion 192 engageable with the body 154. In the embodiment shown, the spacer can be received within opening 170, such that the spacer extends from the body in between the first and second guide surfaces. Such a spacer can be useful for positioning the body at a desired position with respect to a joint and for properly positioning the guide with respect to bones to be cut in more than one plane (e.g., three planes selected from more than one of a frontal plane, a transverse plane, and a sagittal plane). The distance between the spacer and the first guide surface can define a length of tissue removal (e.g., bone or cartilage to be cut) from a first bone, and the distance between the spacer and the second guide surface can define a length of tissue removal (e.g., bone or cartilage to be cut) from a second bone.

As also shown in FIG. 15, bone preparation guide 150 may include or be used with a tissue removal location check member 194. Tissue removal check member 194 may be engageable with the body 154 and configured to extend to a first bone and a second bone. The tissue removal location check member can have a first portion 196 configured to extend into contact with first and second bones and a second portion 198 engageable with the body. In the embodiment shown, the tissue removal check member 194 is configured to extend in the body 154 at both the first and second guiding surfaces. The tissue removal location check member 194 may be useful for allowing a practitioner to see where a tissue removing instrument guided by the surfaces will contact the bone to be prepared.

Bone preparation facilitated by bone preparation guide 150 can be useful, for instance, to facilitate contact between leading edges of adjacent bones, separated by a joint, or different portions of a single bone, separated by a fracture, such as in a bone alignment and/or fusion procedure. A bone may be prepared using one or more bone preparation techniques. In some applications, a bone is prepared by cutting the bone. The bone may be cut transversely to establish a new bone end facing an opposing bone portion. Additionally or alternatively, the bone may be prepared by morselizing an end of the bone. The bone end can be morselized using any suitable tool, such as a rotary bur, osteotome, or drill. The bone end may be morselized by masticating, fenestrating, crushing, pulping, and/or breaking the bone end into smaller bits to facilitate deformable contact with an opposing bone portion.

During a surgical technique utilizing compressor-distractor 100 and instrument 300, a bone may be moved from an anatomically misaligned position to an anatomically aligned position with respect to another bone. Further, both the end of the moved bone and the facing end of an adjacent end may be prepared for fixation. In some applications, the end of at least one of the moved bone and/or the other bone is prepared after moving the bone into the aligned position. In other applications, the end of at least one of the moved bone and/or the other bone is prepared before moving the bone into the aligned position.

Movement of one bone relative to another bone can be accomplished using one or more instruments and/or techniques. In some examples, bone movement is accomplished using a bone positioning device that applies a force to one bone at a single location, such that the bone both translates and rotates in response to the force. This may be accomplished, for example, using a bone positioning guide that includes a bone engagement member, a tip, a mechanism to urge the bone engagement member and the tip towards each other, and an actuator to actuate the mechanism. Additionally or alternatively, bone movement may be accomplished using compressor-distractor 100 by imparting movement to one bone relative to another bone as the compressor-distractor is positioned on substantially parallel pins, causing the pins to move out of their substantially parallel alignment and resulting in movement of the underlying bones in one plane (e.g., frontal plane, sagittal plane, transverse plane), two or more planes, or all three planes. As yet a further addition or alternative, a clinician may facilitate movement by physically grasping a bone, either through direct contact with the bone or indirectly (e.g., by inserting a K-wire, grasping with a tenaculum, or the like), and moving his hand to move the bone.

Regardless of the how movement is accomplished, a surgical technique may or may not utilize a fulcrum. A fulcrum may provide a structure about which rotation and/or pivoting of one bone relative to another bone occurs. The fulcrum can establish and/or maintain space between adjacent bones being moved, preventing lateral translation or base shift of the bones during rotation and/or pivoting. For example, to help avoid the proximal-most base of the first metatarsal 210 from shifting toward the proximal-most base of the second metatarsal 212, a clinician can insert the fulcrum in the notch between first metatarsal 210 and second metatarsal 212 at the base of the metatarsals (e.g., adjacent respective cuneiform) before moving the first metatarsal. The fulcrum can provide a point about which first metatarsal 210 can rotate and/or pivot while helping minimize or avoid base compression between the first metatarsal and the second metatarsal. In addition, use of the fulcrum may cause first metatarsal 210 and medial cuneiform 222 to be better angled relative to guide slots positioned over the end faces of the bones, providing a better cut angle through the guide slots than without use of the fulcrum. This can help reduce or eliminate unwanted spring-back, or return positioning, of first metatarsal 210 after initial realignment of the metatarsal.

When the surgical technique is implemented using a fulcrum, the fulcrum may be the same instrument or a different instrument than instrument 300 defining a sliding surface. For example, in some implementations, instrument 300 is utilized as a fulcrum about which a proximal portion of one bone portion (e.g., first metatarsal) is rotated to close an angle with an adjacent bone portion (e.g., an IMA with a second metatarsal). The same instrument 300 can further be utilized in the same procedure to provide a sliding surface against which the one bone portion (e.g., first metatarsal) is moved relative to another bone portion (e.g., medial cuneiform), such as by translating the bone portion generally axially in a distal to proximal direction within the sagittal plane.

When used, the clinician can insert the fulcrum between first metatarsal 210 and second metatarsal 212 (or other adjacent bones, when not performing a metatarsal realignment) at any time prior to moving the first metatarsal (e.g., by actuating a bone positioning guide or otherwise manipulating the bone). In different embodiments, the fulcrum can be inserted between first metatarsal 210 and second metatarsal 212 before or after inserting joint spacer 188 and/or placing bone preparation guide 150 over the joint being operated upon. In one embodiment, the clinician prepares the joint being operated upon to release soft tissues and/or excise the plantar flare from the base of the first metatarsal 210. Either before or after installing an optional bone positioning guide over adjacent bones, the clinician inserts the fulcrum at the joint between the first metatarsal and the second metatarsal. The clinician can subsequently actuate bone positioning guide 10 (e.g., when used). As distal portion of first metatarsal can move toward the second metatarsal in the transverse plane to close the IMA, thereby pivoting a proximal portion of the first metatarsal about the fulcrum and reducing the IMA between the first metatarsal and the second metatarsal. While use of a fulcrum can minimize or eliminate base compression between adjacent bones being operated upon, in other embodiments, the described systems and techniques can be implemented without using a fulcrum.

An example method for preforming a bone alignment procedure utilizing a compressor-distractor and instrument defining a sliding surface according to the disclosure will now be described with respect to FIGS. 16-25 depicting a foot 200 having a first metatarsal 210, a medial cuneiform 222, and a second metatarsal 212. Unless otherwise indicated, the example steps described can be carried out in any order and need not be performed in the order described.

Figure 16:
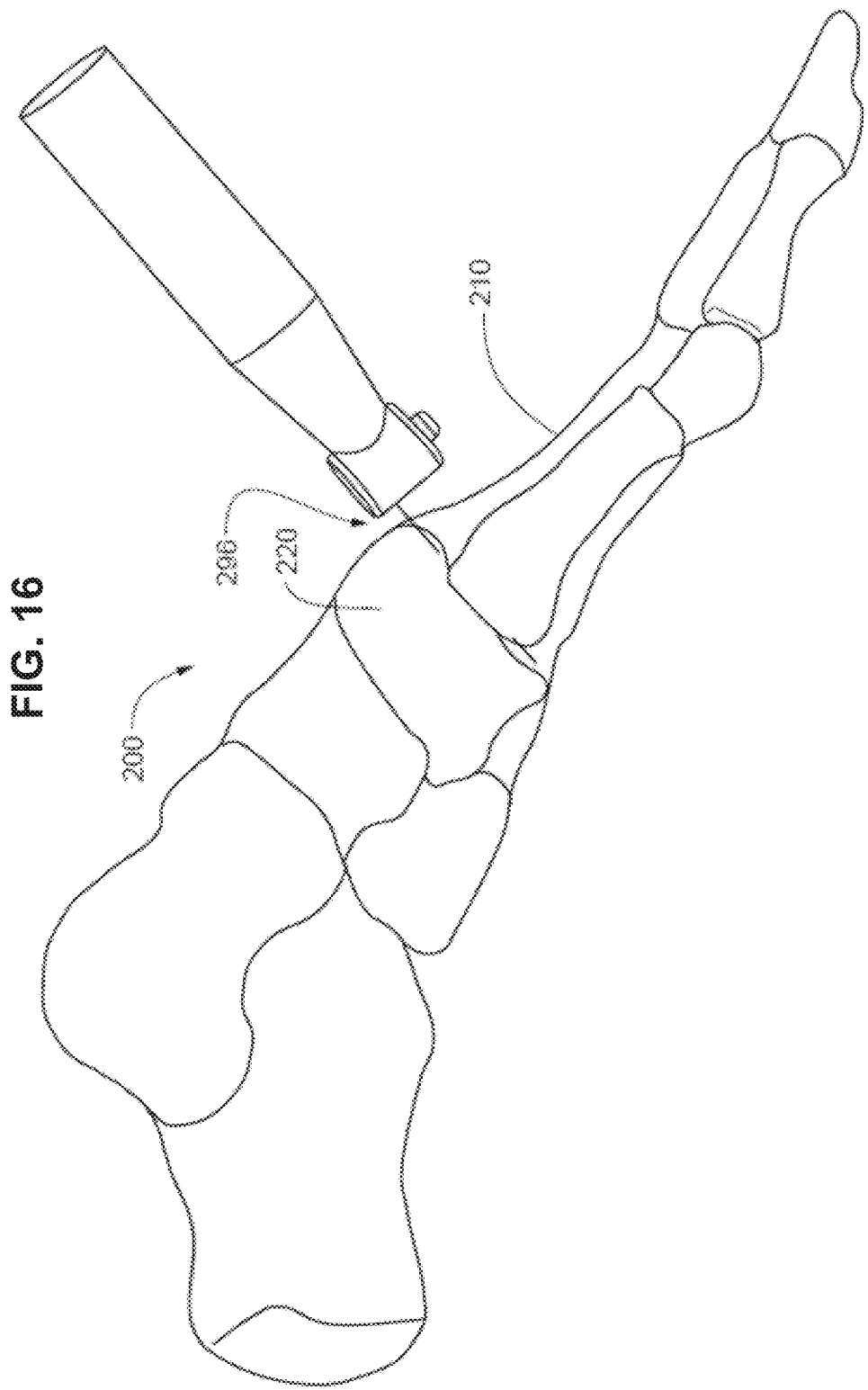
FIG. 16 is a side perspective view of a foot depicting a bone preparation instrument inserted into a joint.

After customary surgical preparation and access, a bone preparation instrument 296 can be inserted into the joint (e.g., first tarsal-metatarsal joint) to release soft tissues and/or excise the plantar flare from the base of the first metatarsal 210, as shown in FIG. 16. Excising the plantar flare may involve cutting plantar flare off the first metatarsal 210 so the face of the first metatarsal is generally planar. This step helps to mobilize the joint to facilitate a deformity correction. In some embodiments, the dorsal-lateral flare of the first metatarsal may also be excised to create space for the deformity correction (e.g., with respect to rotation of the first metatarsal). In certain embodiments, a portion of the metatarsal base facing the medial cuneiform can be removed during this mobilizing step.

Figure 17:
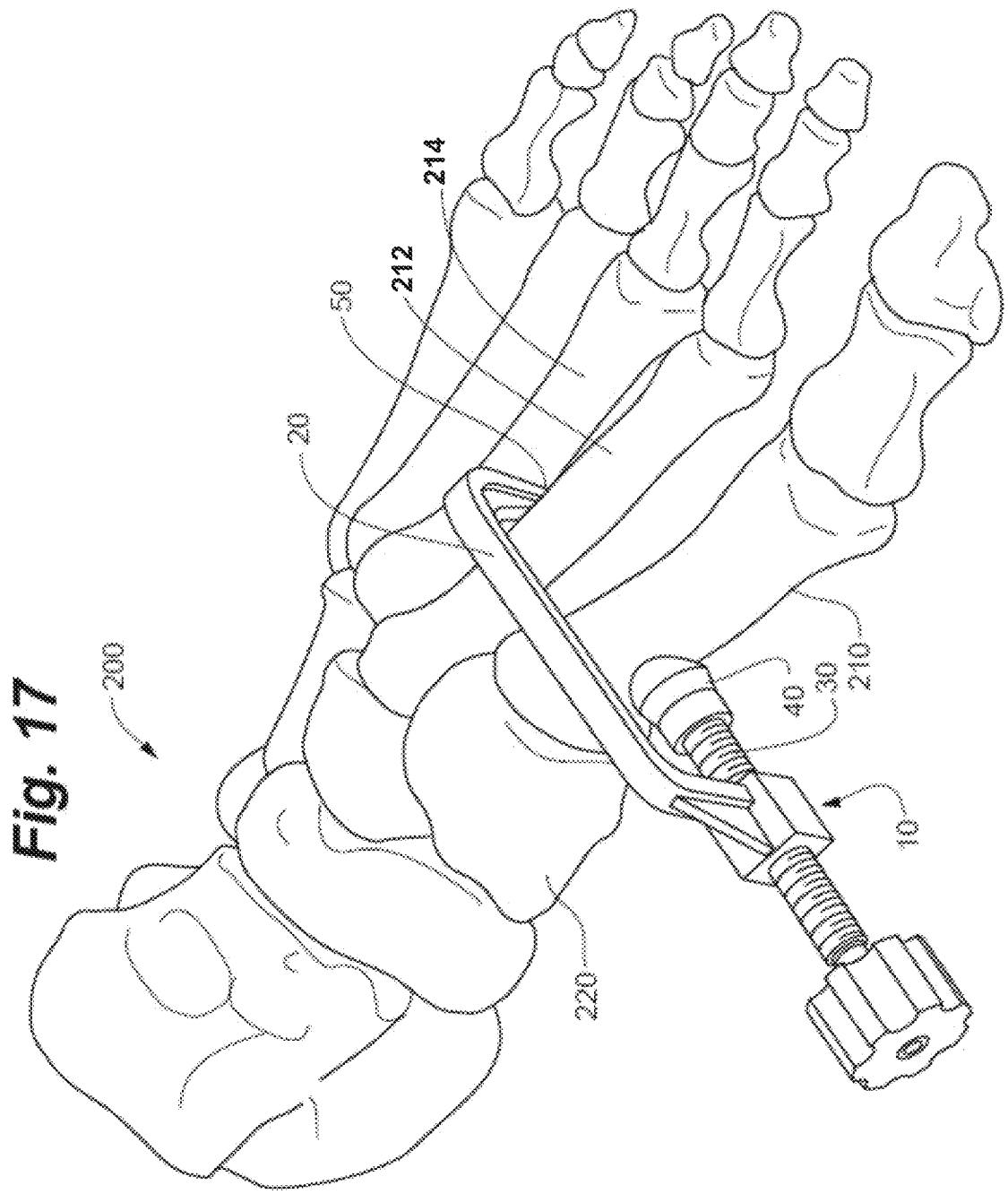
FIG. 17 is a perspective view of a foot depicting a bone positioning guide on the foot prior to an alignment of a first metatarsal.

An incision can be made and, if a bone positioning instrument is going to be used, a tip 50 of a bone positioning guide 10 inserted on the lateral side of a metatarsal other than the first metatarsal 210, such as the second metatarsal 212. As shown in FIG. 17, the tip can be positioned proximally at a base of the second metatarsal 212 and a third metatarsal 294 interface. A surface of a bone engagement member 40 can be placed on the proximal portion of the first metatarsal 210. In some embodiments, the bone engagement member engages a medial ridge of the first metatarsal 210. As shown, the body 20 of the positioning guide can be generally perpendicular to the long axis of the second metatarsal 212.

To help avoid a base shift, a clinician can insert a fulcrum in the notch between first metatarsal 210 and second metatarsal 212 at the base of the metatarsals (e.g., adjacent respective cuneiform) before actuating bone positioning guide 10 or otherwise moving the first metatarsal relative to the medial cuneiform. The fulcrum can provide a point about which first metatarsal 210 can rotate and/or pivot while helping minimize or avoid base compression between the first metatarsal and the second metatarsal. Instrument 300 can be used as the fulcrum or another instrument providing fulcrum functionality can be used.

In applications utilizing bone positioning guide 10, the actuator on the bone positioning guide can be actuated to reduce the angle (transverse plane angle between the first metatarsal and the second metatarsal) and rotate the first metatarsal about its axis (frontal plane axial rotation). The first metatarsal 210 can be properly positioned with respect to the medial cuneiform 222 by moving the bone engagement member 40 bone positioning guide with respect to the tip 50 of the bone positioning guide. In some embodiments, such movement simultaneously pivots the first metatarsal with respect to the cuneiform and rotates the first metatarsal about its longitudinal axis into an anatomically correct position to correct a transverse plane deformity and a frontal plane deformity. Other instrumented and/or non-instrumented approaches can be used to adjustment position of first metatarsal 210 relative to medial cuneiform 222. Thus, other applications utilizing compressor-distractor 100 and instrument 300 may be performed without utilizing bone positioning guide 10.

Figure 18:
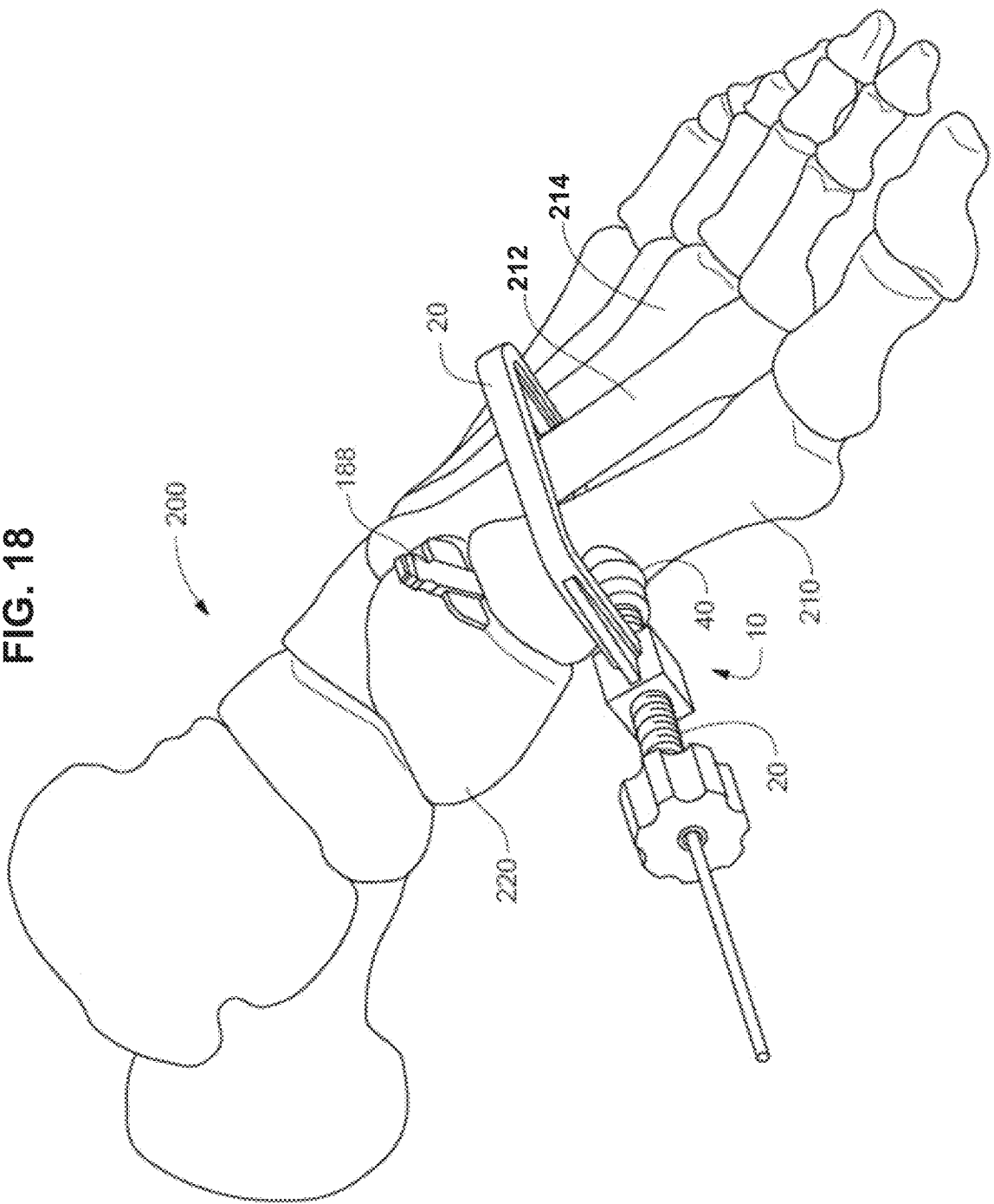
FIG. 18 is a perspective view of a foot depicting a bone positioning guide on the foot after an alignment of a first metatarsal and with a spacer inserted into a joint space.
Figure 19:
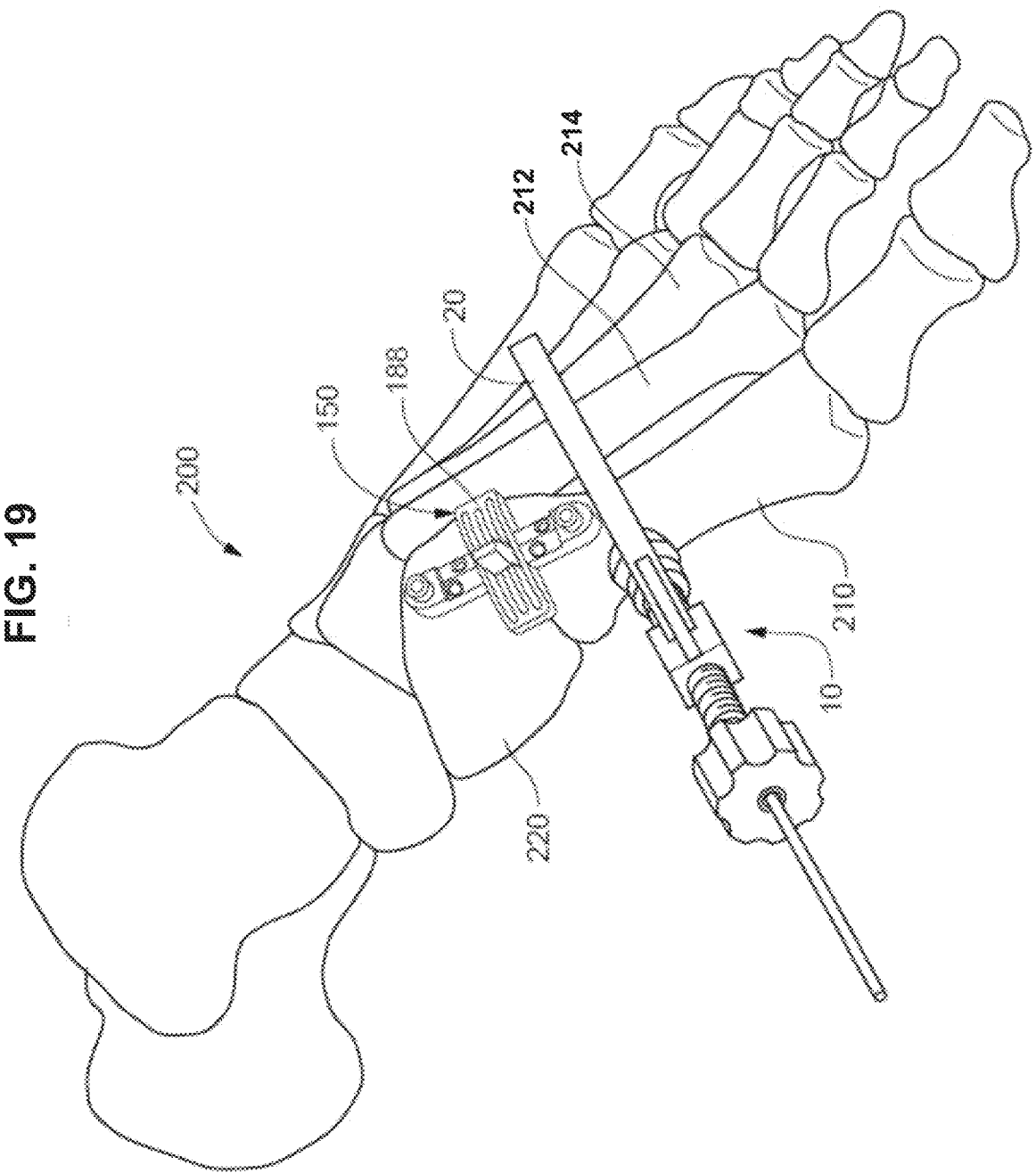
FIG. 19 is a perspective view of a foot depicting a bone preparation guide positioned on the foot.

Independent of whether bone positioning guide 10 is used, an example technique may include positioning joint spacer 188 within the joint between first metatarsal 210 and medial cuneiform 222, as illustrated in FIG. 18. Bone preparation guide 150 can be placed over the joint spacer 188 as shown in FIG. 19 and engaged with the joint spacer to set a position and orientation of the bone preparation guide relative to the joint. In other embodiments, bone preparation guide 150 is placed on the bones without using joint spacer 188 to aid with positioning.

Figure 20:
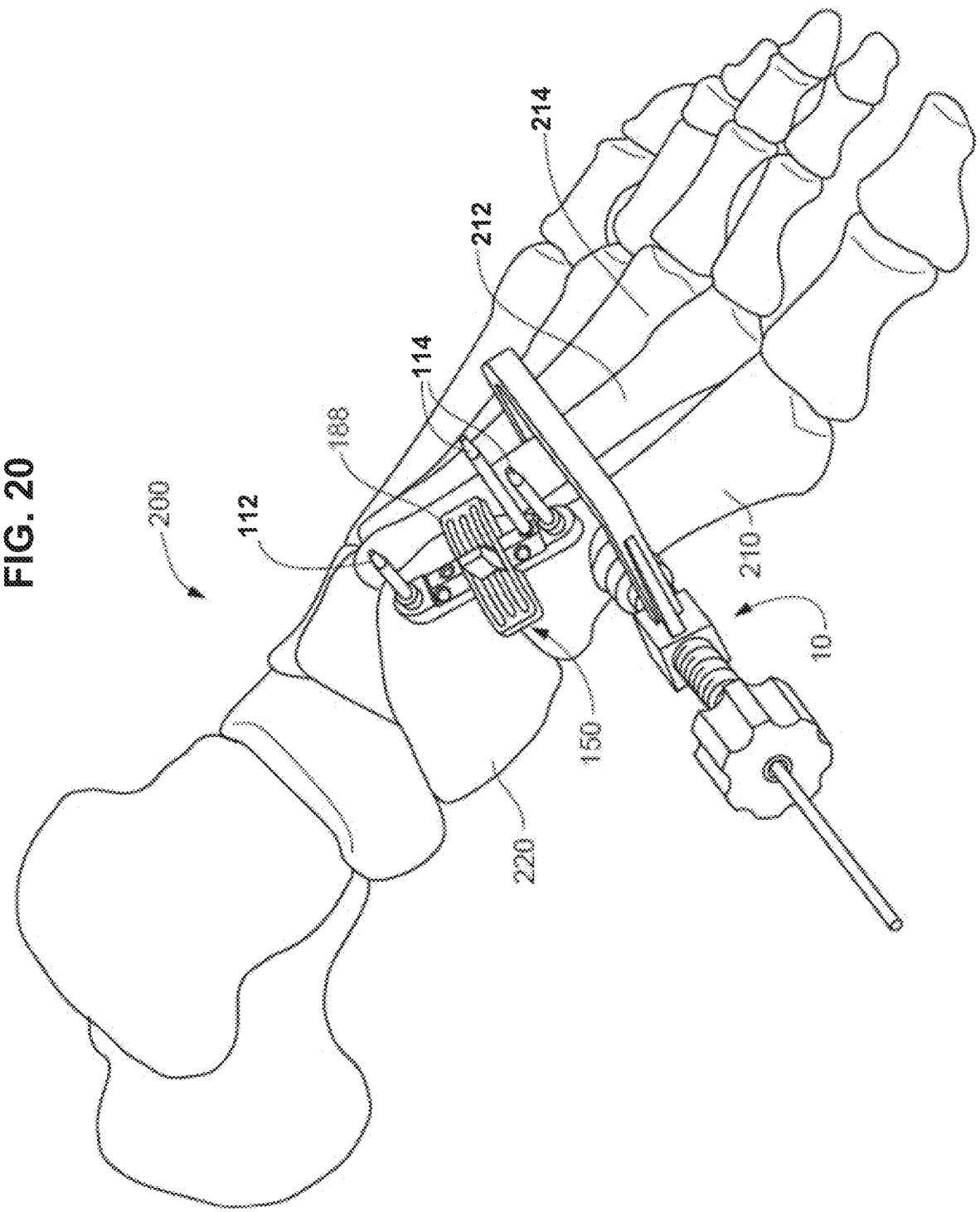
FIG. 20 is a perspective view of a foot depicting a bone preparation guide on the foot with pins inserted through the bone preparation guide.

As depicted in FIG. 20, one or more fixation pins can be inserted into apertures of the bone preparation guide 150 to secure the guide to the first metatarsal 210 and the medial cuneiform 222. The fixation pins inserted into the apertures of bone preparation guide 150 includes a first fixation pin 112 and second fixation pin 114. The first and second fixation pins 112, 114 may be inserted in substantially parallel alignment. The first and second fixation pins 112, 114 may project at least 25 mm above the surface of the bones into which the pins are inserted, such as at least 50 mm, or at least 75 mm. One or more additional pins can be inserted at an angle or in a converging orientation to help prevent movement of the bone preparation guide 150 during a tissue removing step. After insertion of the pins, the spacer 188 (if used) can optionally be removed in embodiments having a selectively engageable spacer.

In some applications, the end of the first metatarsal 210 facing the medial cuneiform 222 can be prepared with a tissue removing instrument 296 guided by a guide surface of bone preparation guide 150 (e.g., inserted through a slot defined by a first guide surface and a first facing surface). In some embodiments, the first metatarsal 210 end preparation is done after at least partially aligning the bones, e.g., by actuating bone positioning guide 10 or otherwise moving the first metatarsal but after preparing the end of first metatarsal 210. In other embodiments, the first metatarsal 210 end preparation is done before the alignment of the bones, e.g., by preparing the end of the first metatarsal 210 before installing compressor-distractor 100 and instrument 300.

In addition to preparing the end of first metatarsal 210, the end of the medial cuneiform 222 facing the first metatarsal 210 can be prepared with the tissue removing instrument 296 guided by a guide surface of bone preparation guide 150 (e.g., inserted through a slot defined by a second guide surface and a second facing surface). In some embodiments, the medial cuneiform 222 end preparation is done after the alignment of the bones. In yet other embodiments, the medial cuneiform 222 end preparation is done before the alignment of the bones. In embodiments that include cutting bone or cartilage, the cuneiform cut and the metatarsal cut can be parallel, conforming cuts. In some examples, a saw blade can be inserted through a first slot to cut a portion of the medial cuneiform and the saw blade can be inserted through a second slot to cut a portion of the first metatarsal.

Figure 21:
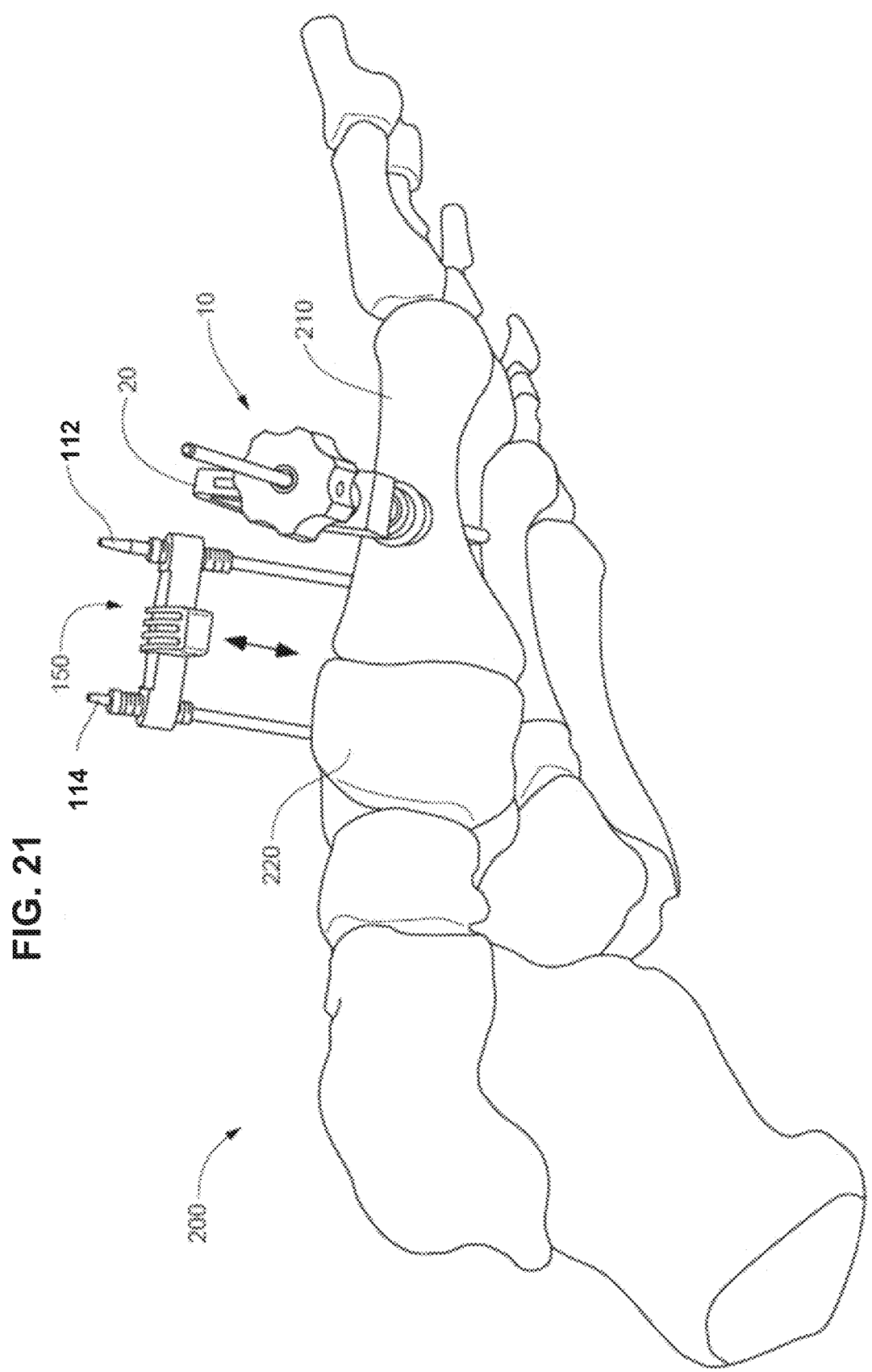
FIG. 21 is a perspective view of a foot depicting a removal of a bone preparation guide.

Any angled/converging pins can be removed and the bone preparation guide 150 can be lifted off the substantially parallel first and second pins 112, 114, as shown in FIG. 21. These substantially parallel pins can receive compressor-distractor 100. For example, the clinician can position compressor-distractor 100 so the bottom side of first pin-receiving hole 108 is positioned over first pin 112 and the bottom side of second pin-receiving hole 110 is positioned over second pin 114. The clinician can then slide compressor-distractor 100 down over the pins toward the underlying bones, e.g., until the bottom side of the compressor-distractor is adjacent to or in contact with the underlying bones. The clinician may adjust the spacing between first engagement arm 102 and second engagement arm 104 by actuating actuator 106 until the separation distance corresponds to the spacing between first and second pins 112, 114, before installing the compressor-distractor down over the pins. If first pin-receiving hole 108 is angled relative to second pin-receiving hole 110, the process of inserting compressor-distractor 100 on the pins can cause first and second pins 112, 114 to shift from their substantially parallel alignment to a nonparallel alignment corresponding to the angular position of the pin-receiving holes. By contrast, when first pin-receiving hole 108 is parallel to second pin-receiving hole 110, the process of inserting compressor-distractor 100 on the pins may not cause first and second pins 112, 114 to shift substantially from their parallel alignment.

In applications where bone positioning guide 10 is utilized, the bone positioning guide may be removed before or after bone preparation guide 150 is removed and compressor-distractor 100 is installed. In either case, in some examples, a temporary fixation device such as an olive pin, k-wire, or other fixation structure may be used to maintain the position of the underlying bones (e.g., first metatarsal 210 relative to medial cuneiform 222) while bone preparation guide 150 is removed and compressor-distractor 100 is installed.

With compressor-distractor 100 pinned to underlying bones (e.g., first metatarsal 210 and medial cuneiform 222), actuator 106 may be actuated to distract the underlying bones. For example, the clinician may turn knob 126 to cause second engagement arm 104 to move away from first engagement arm 102, opening or enlarging a gap between the underlying bones. When pin to first metatarsal 210 and medial cuneiform 222, the clinician can actuate actuator 106 to open the TMT joint. While in this example application compressor-distractor 100 is described as being attached to first metatarsal 210 and medial cuneiform 222 to distract the two bones (e.g., followed by subsequent compression), alternative implementations may involve manual distraction of the bones. In these alternatives, the clinician may attach compressor-distractor 100 to first metatarsal 210 and medial cuneiform 222 after distracting the two bone portions, e.g., and only utilize the compression feature of compressor-distractor 100 without utilizing the distraction feature.

Figure 22:
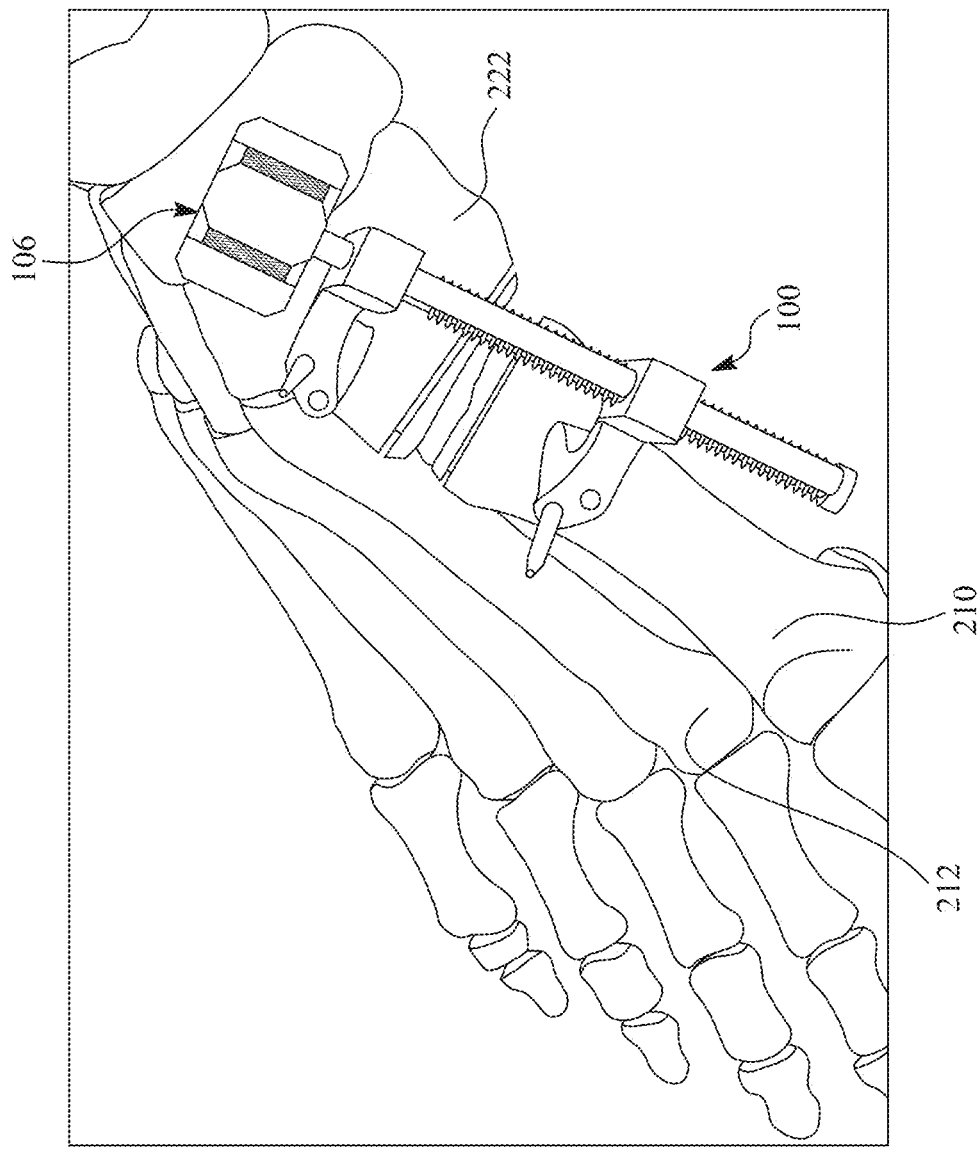
FIG. 22 is a perspective view of a foot showing an example distracted position of a compressor-distractor in which a first metatarsal is spaced from a medial cuneiform.

In either case, with the underlying bones distracted, the clinician may clean or otherwise prepare the space between the bones and/or the end face of one or both bones. The clinician may clean the space by removing excess cartilage, bone, and/or other cellular debris that may natively exist or may have been created during the bone preparation step that may inhibit infusion. FIG. 22 is a perspective view of a foot showing an example distracted position of compressor-distractor 100 in which first metatarsal 210 is spaced from medial cuneiform 222. In this example, bone debris from the prepared end of first metatarsal 210 and the prepared end of medial cuneiform 222 is illustrated as being positioned in the tarsal-metatarsal space. The clinician can remove this debris or perform other desired clean-up with the two bones distracted from each other.

Figure 23:
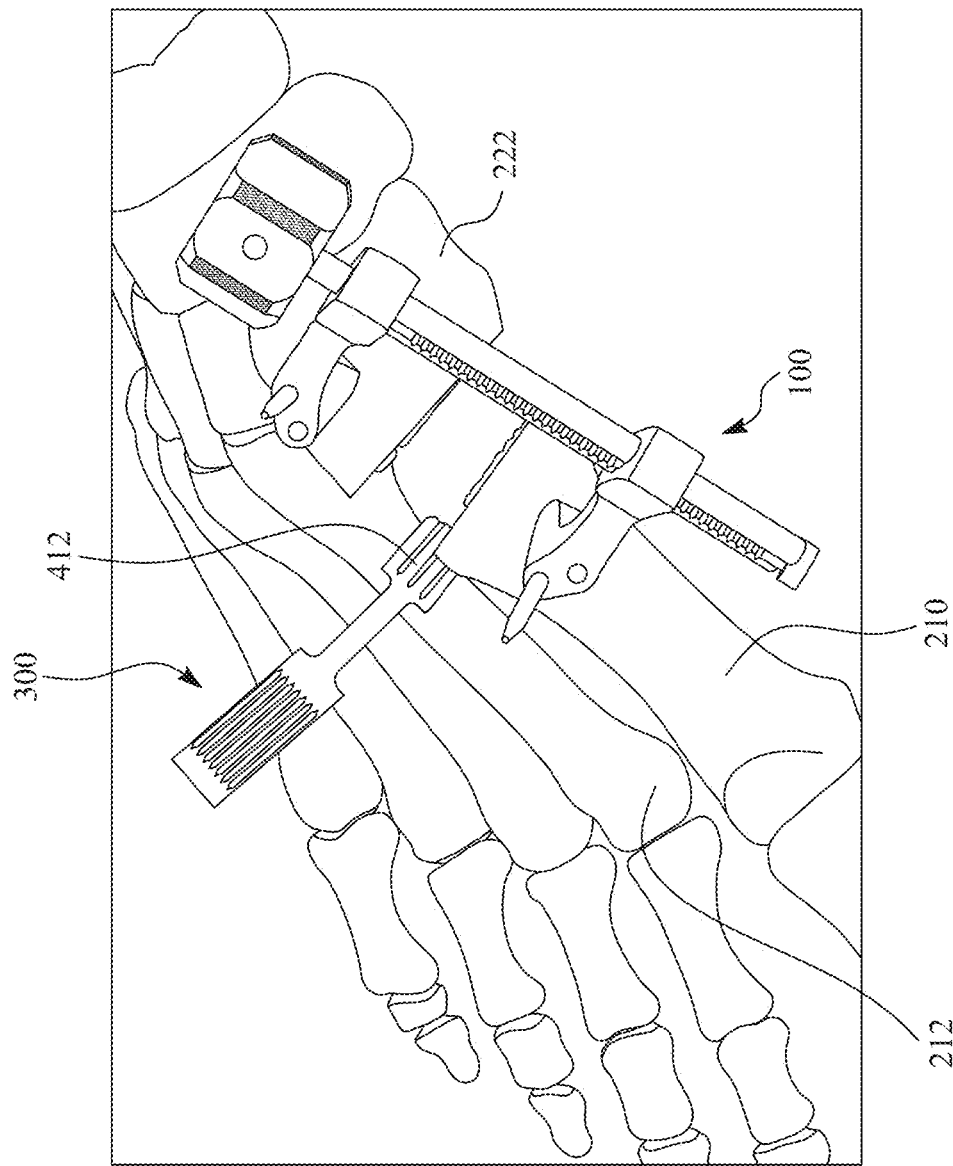
FIG. 23 is a perspective view of a foot showing an example positioning of an instrument defining a sliding surface relative to a first metatarsal.

Independent of whether the clinician utilizes compressor-distractor 100 to distract the underlying bones for cleaning, the clinician can insert instrument 300 defining a sliding surface between first metatarsal 210 and second metatarsal 294. FIG. 23 is a perspective view of a foot showing an example positioning of instrument 300 relative to first metatarsal 210. In this example, instrument 300 defines a sliding surface 412, which is positioned between first metatarsal 210 and second metatarsal 212. Sliding surface 412 can be positioned at any desired location (e.g., in the distal to proximal direction) along the lengths of the first and second metatarsals.

In some implementations, such as that illustrated in FIG. 23, instrument 300 is positioned between the prepared end or base of first metatarsal 210 and second metatarsal 212. For example, instrument 300 may be positioned between a lateral side of the prepared end of first metatarsal 210 and a medial side of second metatarsal 212. The edge of the prepared end of first metatarsal 210 may be positioned in the plane of sliding surface 412 or, in other applications, may be positioned proximally or distally of sliding surface 412. Instrument 300 may or may not contact the medial side of second metatarsal 212 in addition to contacting the lateral side of first metatarsal 210.

In any application, instrument 300 and sliding surface 412 may help medialize first metatarsal 210 as compressor-distractor 100 is actuated to compress first metatarsal 210 toward medial cuneiform 222. As compressor-distractor 100 is actuated to move first metatarsal 210 generally axially (e.g., in the proximal direction) toward medial cuneiform 222, the prepared end of the metatarsal and/or a lateral portion of the first metatarsal may translate in contact with and/or across sliding surface 412. The presence of sliding surface 412 between first metatarsal 210 and second metatarsal 212 can help prevent or limit the extent to which the first metatarsal (e.g. prepared end of the metatarsal) catches on tissue, boney substrate (e.g., the surface of second metatarsal 212), or other obstructing matter.

In some examples, instrument 300 defining sliding surface 412 may be positioned substantially stationary (non-moving) between first metatarsal 210 and second metatarsal 212 as first metatarsal 210 is moved generally axially toward medial cuneiform 222. In other implementations, instrument 300 defining sliding surface 412 may be moved as first metatarsal 210 is moved toward medial cuneiform 22. For example, the clinician may grasp or otherwise hold instrument 300 and move the position of the instrument as first metatarsal 210 is compressed toward and/or against the medial cuneiform 222.

Instrument 300 defining sliding surface 412 can be inserted between first metatarsal 210 and second metatarsal 212 as any desired time during the surgical procedure. In the illustrated arrangement, instrument 300 is depicted as being inserted between the two bone portions after removal of bone preparation guide 150 and distraction of first metatarsal 210 from medial cuneiform 222 but prior to compression of the first metatarsal to the medial cuneiform. As another example, the clinician may distract the first metatarsal 210 from medial cuneiform 222, preform any desired clean-up, and begin compressing the first metatarsal toward the medial cuneiform. The clinician may observe where first metatarsal 210 is frictionally interfering with obstructing matter (e.g., second metatarsal 212) during the initial compression and insert instrument 300 to inhibit further interference. As yet a further example, the clinician may utilize instrument 300 as both a fulcrum and an instrument defining a sliding surface, as discussed above. In these applications, the clinician may insert instrument 300 to function as a fulcrum during earlier bone realignment and leave the instrument in the intermetatarsal space, e.g., for the duration of the surgical procedure. Thus, instrument 300 may be present in the intermetatarsal space during distraction and compression, although the clinician may realign the instrument within the intermetatarsal, e.g., immediately prior to or during the compression phase.

Figure 24:
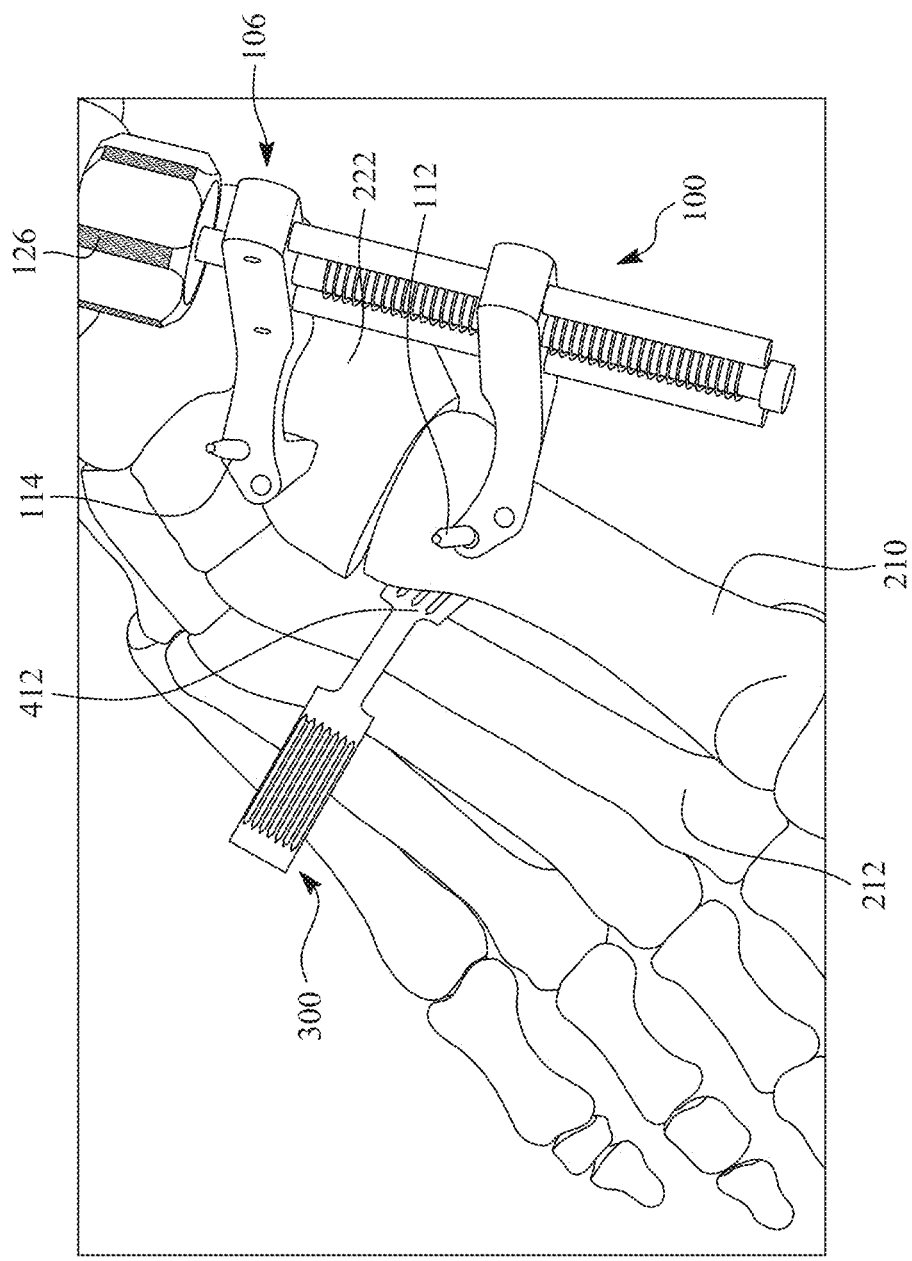
FIG. 24 is a perspective view of a foot showing an example positioning of an instrument defining a sliding surface relative to a first metatarsal following compression using a compressor-distractor.

Independent of when the clinician inserts instrument 300, the clinician may actuate actuator 106 to compress the bones together for permanent fixation infusion. The clinician may turn knob 126 to cause second engagement arm 104 to move toward first engagement arm 102, for example until the end faces of the underlying bones contact each other and/or a compressive force is applied through pins 112, 114 to the end faces, as illustrated in FIG. 24. While in this example application compressor-distractor 100 is described as being used to compress the two bones, alternative implementations may involve manual compression of the bones or compression using a different instrument. In these alternatives, the clinician may attach compressor-distractor 100 to first metatarsal 210 and medial cuneiform 222 to distract the two bone portions, e.g., and only utilize the distraction feature of compressor-distractor 100 without utilizing the compression feature.

Figure 25:
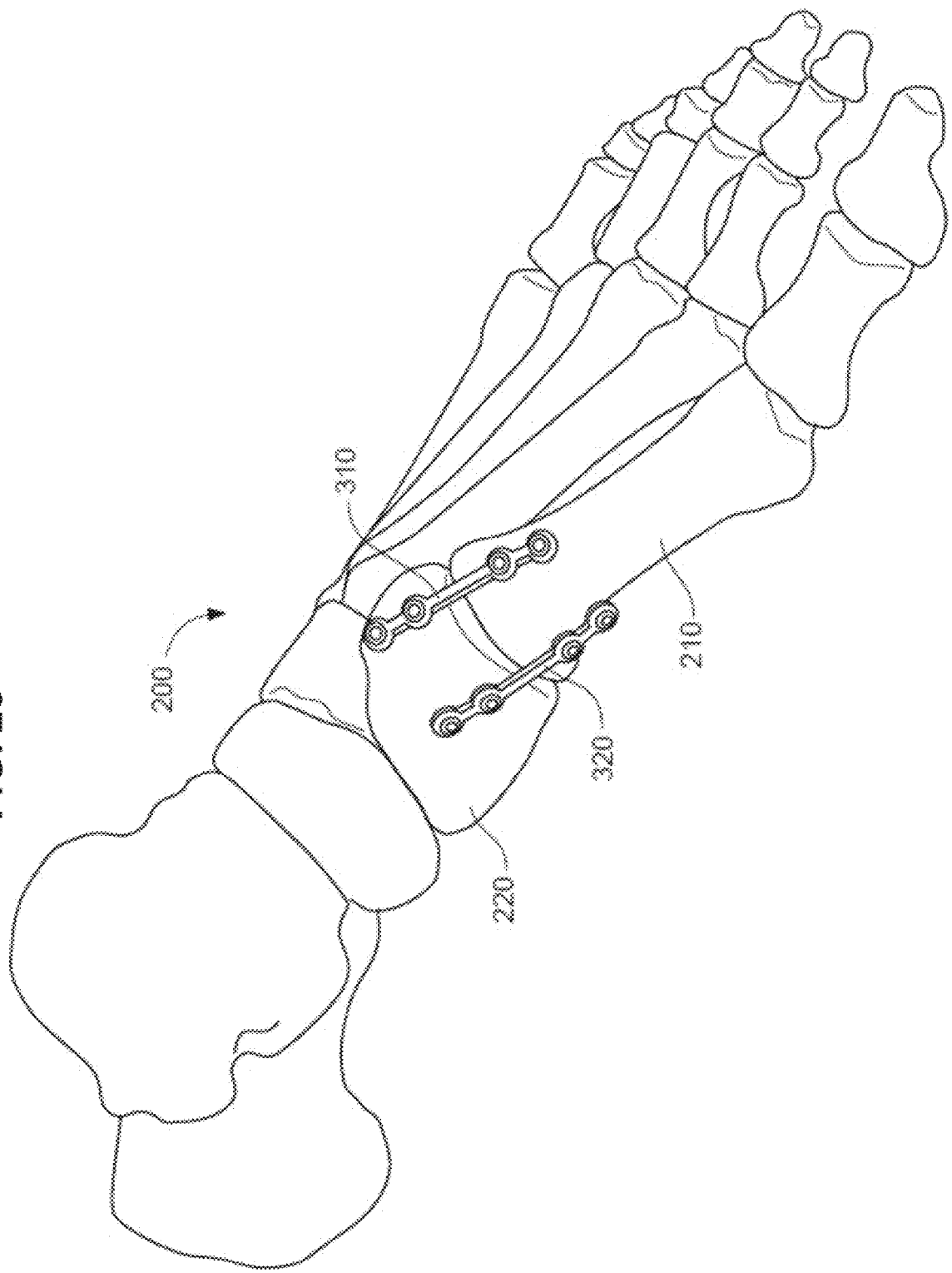
FIG. 25 is a side perspective view of a foot depicting bone plates across a joint between first and second bones.

With the end faces pressed together via compressor-distractor 100, the clinician may provisionally or permanently fixate the bones or bones portions together. For example, one or more bone fixation devices can be applied across the joint and to the two bones to stabilize the joint for fusion, such as two bone plates positioned in different planes. FIG. 25 illustrates an example fixation device arrangement that includes a first bone plate 310 positioned on a dorsal-medial side of the first metatarsal and medial cuneiform and a second bone plate 320 positioned on a medial-plantar side of the first metatarsal and the medial cuneiform. In other embodiments, second bone plate 320 can be a helical bone plate positioned from a medial side of the cuneiform to a plantar side of the first metatarsal across the joint space. The plates can be applied with the insertion of bone screws. Example bone plates that can be used as first bone plate 310 and/or second bone plate 320 are described in US Patent Publication No. US2016/0192970, titled "Bone Plating System and Method" and filed Jan. 7, 2016, which is incorporated herein by reference. Other types in configurations of bone fixation devices can be used, and the disclosure is not limited in this respect.

Compressor-distractor devices and instruments providing sliding surfaces, along with associated techniques and systems, have been described. In some examples, a compressor-distractor and instrument defining a sliding surface according to the disclosure is included in a disposable, sterile kit that includes associated surgical instrumentation, such as bone positioning guide and/or a preparation guide described herein. Other components that may be included within the sterile kit include bone fixation devices, bone fixation screws, pins for insertion into pin-receiving holes, and the like.

Various examples have been described. These and other examples are within the scope of the following claims.

The invention claimed is:

1. A method comprising:
preparing an end of a metatarsal;
preparing an end of a cuneiform separated from the metatarsal by a tarsometatarsal joint;
inserting an instrument defining a sliding surface between the metatarsal and a laterally-adjacent metatarsal; and
compressing a prepared end of the metatarsal and a prepared end of the cuneiform together, wherein compressing the prepared end of the metatarsal and the prepared end of the cuneiform together comprises moving the metatarsal across the sliding surface of the instrument toward the cuneiform.

2. The method of claim 1, wherein inserting the instrument defining the sliding surface between the metatarsal and the laterally-adjacent metatarsal comprises inserting the instrument defining the sliding surface between a proximal lateral end of the metatarsal and a medial side of the laterally-adjacent metatarsal.

3. The method of claim 1, wherein compressing the prepared end of the metatarsal and the prepared end of the cuneiform together comprises maintaining the instrument defining the sliding surface substantially stationary as the metatarsal is moved toward the cuneiform.

4. The method of claim 1, wherein compressing the prepared end of the metatarsal and the prepared end of the cuneiform together comprises moving the instrument defining the sliding surface with the metatarsal as the metatarsal is moved toward the cuneiform.

5. The method of claim 1, further comprising distracting the metatarsal from the cuneiform, wherein inserting the instrument defining the sliding surface between the metatarsal and the laterally-adjacent metatarsal comprises inserting the instrument defining the sliding surface between the metatarsal and the laterally-adjacent metatarsal while the metatarsal is distracted from the cuneiform.

6. The method of claim 5, further comprising cleaning a distracted space between the metatarsal and the cuneiform prior to inserting the instrument defining the sliding surface between the metatarsal and the laterally-adjacent metatarsal.

7. The method of claim 1, wherein:
preparing the end of the metatarsal comprises one or both of cutting and fenestrating the end of the metatarsal; and
preparing the end of the cuneiform comprises one or both of cutting and fenestrating the end of the cuneiform.

8. The method of claim 1, wherein:
preparing the end of the metatarsal comprises cutting the end of the metatarsal; and
preparing the end of the cuneiform comprises cutting the end of the cuneiform.

9. The method of claim 8, wherein:
cutting the end of the metatarsal comprises cutting the end of the metatarsal using a bone preparation guide to guide a cutting instrument to cut the end of the metatarsal; and
cutting the end of the cuneiform comprises using the bone preparation guide to guide the cutting instrument to cut the end of the cuneiform.

10. The method of claim 1, wherein inserting the instrument defining the sliding surface between the metatarsal and the laterally-adjacent metatarsal comprises inserting the instrument after preparing the end of the metatarsal and after preparing the end of the cuneiform.

11. The method of claim 1, further comprising:
moving the metatarsal in one or both of a transverse plane and a frontal plane to correct a bunion; and
fixating a moved position of the metatarsal relative to the cuneiform by inserting at least one fixation device across the tarsometatarsal joint.

12. The method of claim 11, wherein moving the metatarsal in one or both of the transverse plane and the frontal plane comprises moving the metatarsal in the transverse plane to close an intermetatarsal angle between the metatarsal and the laterally-adjacent metatarsal.

13. The method of claim 1, further comprising attaching a compressor-distractor to the metatarsal and the cuneiform, wherein compressing the prepared end of the metatarsal and the prepared end of the cuneiform together comprises actuating the compressor-distractor.

14. The method of claim 1, wherein:
the instrument has a length extending from a leading end to a trailing end and tapers in thickness along at least a portion of the length from the trailing end to the leading end; and
the instrument has a generally rectangular cross-sectional shape.

15. The method of claim 1, wherein:
the metatarsal is a first metatarsal;
the cuneiform is a medial cuneiform; and
the laterally-adjacent metatarsal is a second metatarsal.

16. A method comprising:
distracting a metatarsal from an opposed cuneiform to open a space between the metatarsal and the opposed cuneiform;
inserting an instrument defining a sliding surface between the metatarsal and a laterally-adjacent metatarsal; and
moving the metatarsal across the sliding surface of the instrument toward the opposed cuneiform to close the space between the metatarsal and the opposed cuneiform.

17. The method of claim 16, wherein inserting the instrument defining the sliding surface between the metatarsal and the laterally-adjacent metatarsal comprises inserting the instrument defining the sliding surface between a proximal lateral end of the metatarsal and a medial side of the laterally-adjacent metatarsal.

18. The method of claim 16, wherein moving the metatarsal across the sliding surface of the instrument toward the opposed cuneiform comprises maintaining the instrument defining the sliding surface substantially stationary as the metatarsal is moved toward the opposed cuneiform.

19. The method of claim 16, wherein moving the metatarsal across the sliding surface of the instrument toward the opposed cuneiform comprises moving the instrument defining the sliding surface with the metatarsal as the metatarsal is moved toward the opposed cuneiform.

20. The method of claim 16, further comprising, prior to moving the metatarsal across the sliding surface of the instrument toward the opposed cuneiform:
preparing an end of the metatarsal; and
preparing an end of the opposed cuneiform.

21. The method of claim 20, further comprising:
moving the metatarsal in one or both of a transverse plane and a frontal plane to correct a bunion; and
fixating a moved position of the metatarsal relative to the opposed cuneiform by inserting at least one fixation device across a tarsometatarsal joint separating the metatarsal from the opposed cuneiform.

22. The method of claim 16, further comprising attaching a compressor-distractor to the metatarsal and the opposed cuneiform, wherein moving the metatarsal across the sliding surface of the instrument toward the opposed cuneiform comprises actuating the compressor-distractor.

23. The method of claim 16, wherein moving the metatarsal across the sliding surface of the instrument toward the opposed cuneiform comprises moving the metatarsal axially toward the opposed cuneiform.

24. The method of claim 23, wherein inserting the instrument defining the sliding surface between the metatarsal and the laterally-adjacent metatarsal comprises inserting the instrument between the metatarsal and obstructing matter frictionally interfering with axial movement of the metatarsal toward the opposed cuneiform.

25. The method of claim 16, wherein:
the metatarsal is a first metatarsal;
the opposed cuneiform is a medial cuneiform; and
the laterally-adjacent metatarsal is a second metatarsal.

* * * * *